(12) United States Patent
Parenicova et al.

(10) Patent No.: US 9,307,776 B2
(45) Date of Patent: Apr. 12, 2016

(54) PREGASTRIC ESTERASE AND DERIVATIVES THEREOF

(71) Applicant: DSM IP ASSETS B.V., Te Heerlen (NL)

(72) Inventors: Lucie Parenicova, Echt (NL); Ronald Busink, Echt (NL); Jan Metske Van Der Laan, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/168,593

(22) Filed: Jan. 30, 2014

(65) Prior Publication Data

US 2014/0186494 A1      Jul. 3, 2014

Related U.S. Application Data

(62) Division of application No. 13/203,086, filed as application No. PCT/EP2010/052903 on Mar. 8, 2010, now Pat. No. 8,703,463.

(30) Foreign Application Priority Data

Mar. 10, 2009   (EP) ..................................... 09154780

(51) Int. Cl.
| | |
|---|---|
| *C12N 9/20* | (2006.01) |
| *A23C 19/06* | (2006.01) |
| *A23C 19/032* | (2006.01) |
| *A23C 19/072* | (2006.01) |
| *A23C 19/082* | (2006.01) |

(52) U.S. Cl.
CPC ........... *A23C 19/063* (2013.01); *A23C 19/0328* (2013.01); *A23C 19/072* (2013.01); *A23C 19/082* (2013.01); *C12N 9/20* (2013.01)

(58) Field of Classification Search
None
See application file for complete search history.

(56) References Cited

U.S. PATENT DOCUMENTS

| | | | |
|---|---|---|---|
| 4,119,732 | A | 10/1978 | Kratochvil |
| 5,801,034 | A | 9/1998 | Lawlis et al. |
| 7,226,771 | B2 | 6/2007 | Gramatikova et al. |
| 2004/0001819 | A1 | 1/2004 | Bolen et al. |

FOREIGN PATENT DOCUMENTS

WO      2008076966      6/2008

OTHER PUBLICATIONS

Giu et al. (4/3/13) database UNiProt, Accession No. L811S2.*
DiPalma et al. (2/22/12) Database UniProt, Accession No. H0WU60.*
Timmermans M Y J et al. "The cDNA Sequence Encoding Bovine Preasric Esterase", Gene, Elsevier, Amsterdam, NL, vol. 147, No. 2 (1994) pp. 259-262, XP023540953.
Klein R. et al. "Altered Acyl Chain Length Specificity of Rhizopus Delemar Lipase Through Mutagenesis and Molecular Modeling", Lipids, Champaign, IL, US. vol. 32, No. 2 (1997) pp. 123-130, XP009088258.
Wicker-Planquart C et al. "Site-Directed Removal of N-Glycosylation Sites in Human Gastric Lipase", European Journal of Biochemistry/FEBS (1999) vol. 262, No. 3, pp. 644-651, XP002562540.
Mahadik Nutan D et al. "Production of Acidic Lipase by Aspergillus Niger in Solid State Fermentation", Process Biochemistry, vol. 38, No. 5(2002), pp. 715-721, XP002594610.
Horikoshi Koki "Alkalaphiles: From an Industrial Point of View", FEMS Microbiology Reviews, Elsevier, Amsterdam, NL, vol. 18, No. 2-3 (1996), pp. 259-270, XP002377542.
Dension S H "pH Regulation of Gene Expression in Fungi", Fungal Genetics and Biology ;FG & B Mar. 2000 LNKD-PUBMED, vol. 29, No. 2, pp. 61-71, XP002594611.
Sharma E Al. "Production, Purification, Characterization, and Applications of Lipases", Biotechnology Advances, Elsevier Publishing, Barking, GB LNKD-D01:10.1016/S0734-9750(01) 00086-6, vol. 19, No. 8 (2001), pp. 627-662, XP004343846.
International Search Report of PCT/EP2010/052903 mailed Aug. 8, 2010.

* cited by examiner

*Primary Examiner* — Nashaat Nashed
(74) *Attorney, Agent, or Firm* — McBee Moore Woodward & Vanik IP, LLC

(57) ABSTRACT

The present invention relates to novel lipase polynucleotide sequences, their corresponding proteins as well as ways of manufacturing said sequences and said proteins and use of the proteins in the preparation of food compositions. The invention further relates to methods for releasing proteins from the exterior of a host cell as well as to a method for killing micro-organisms.

13 Claims, 10 Drawing Sheets

```
WT    1    FLGKIAKNPEASMNVSQMISYWGYPSEMHKVITADGYILQVYRIPHGKNN    50
           |||||||||||||||||||||||||||.|||.|.|||||:|.||||||.|
MUT3  1    FLGKIAKNPEASMNVSQMISYWGYPSEEHKVTTEDGYILEVNRIPHGKKN    50

WT    51   ANHLGQRPVVFLQHGLLGSATNWISNLPKNSLGFLLADAGYDVWLGNSRG   100
           :.:.||||||||||||||||||||||||||||||||||||||||||||||
MUT3  51   SENTGQRPVVFLQHGLLGSATNWISNLPKNSLGFLLADAGYDVWLGNSRG   100

WT    101  NTWAQEHLYYSPDSPEFWAFSFDEMAEYDLPSTIDFILRRTGQKKLHYVG   150
           ||||::||||||||.|||||||||||:|||||||||||||||||||||||
MUT3  101  NTWARKHLYYSPDSKEFWAFSFDEMAKYDLPSTIDFILRRTGQKKLHYVG   150

WT    151  HSQGTTIGFIAFSTSPTLAEKIKVFYALAPVATVKYTKSLFNKLALIPHF   200
           ||||||||||||||||.||||||.||||||||||||||||||||||||||
MUT3  151  HSQGTTIGFIAFSTSPELAEKIKTFYALAPVATVKYTKSLFNKLALIPHF   200

WT    201  LFKIIFGDKMFYPHTFLEQFLGVEMCSRETLDVLCKNALFAITGVDNKNF   250
           ||||||||||||||||||||||||||||||||||||||||||||||||||
MUT3  201  LFKIIFGDKMFYPHTFLEQFLGVEMCSRETLDVLCKNALFAITGVDNKNF   250

WT    251  NMSRLDVYIAHNPAGTSVQNTLHWRQAVKSGKFQAFDWGAPYQNLMHYHQ   300
           ||||||||||||||||||||||||||||||||||||:|||:|.||-||||
MUT3  251  NMSRLDVYIAHNPAGTSVQNTLHWRQAVKSGKFQAYDWGSPDQNRMHYHQ   300

WT    301  PTPPIYNLTAMNVPIAVWSADNDLLADPQDVDFLLSKLSNLIYHKEIPNY   350
           .|||||||||||.|||||||||||||||||..||||||||||||||||||
MUT3  301  STPPIYNLTAMNVPTAVWSADNDLLADPQDVKNLLSKLSNLIYHKEIPNY   350

WT    351  NHLDFIWAMDAPQEVYNEIVSLMAEDKK   378
           |||||||..|||||||||||||.||||
MUT3  351  NHLDFIWGEDAPQEVYNEIVSLMKEDKK   378
```

Fig. 2

```
WT      1    FLGKIAKNPEASMNVSQMISYWGYPSEMHKVITADGYILQVYRIPHGKNN    50
             ||||||||||||||||::||||||||.|:|.|.||||:|.||||||.|
MUT4    1    FLGKIAKNPEASMNVSEIISYWGYPSEEHEVTTEDGYILEVNRIPHGKKN    50

WT      51   ANHLGQRPVVFLQHGLLGSATNWISNLPKNSLGFLLADAGYDVWLGNSRG    100
             :.|.|:||||||||||||||||||||||||||||||||||||||||||||
MUT4    51   SEHTGKRPVVFLQHGLLGSATNWISNLPKNSLGFLLADAGYDVWLGNSRG    100

WT      101  NTWAQEHLYYSPDSPEFWAFSFDEMAEYDLPSTIDFILRRTGQKKLHYVG    150
             |||:::|...||||.|||||||||||:||||||||||::|||||||||
MUT4    101  NTWSRKHKTLSPDSKEFWAFSFDEMAKYDLPSTIDFILKKTGQKKLHYVG    150

WT      151  HSQGTTIGFIAFSTSPTLAEKIKVFYALAPVATVKYTKSLFNKLALIPHF    200
             ||||||||||||||.||:|||.|||||||||||||||||||||.:|.|
MUT4    151  HSQGTTIGFIAFSTSPELAKKIKTFYALAPVATVKYTKSLFNKLAHLPEF    200

WT      201  LFKIIFGDKMFYPHTFLEQFLGVEMCSRETLDVLCKNALFAITGVDNKNF    250
             |||.:||||.|||||||||||||||||||||||||||||||||||||||
MUT4    201  LFKDLFGDKEFYPHTFLEQFLGVEMCSRETLDVLCKNALFAITGVDNKNF    250

WT      251  NMSRLDVYIAHNPAGTSVQNTLHWRQAVKSGKFQAFDWGAPYQNLMHYHQ    300
             |||||||||||||||||||||||||||||||||||||||:|.||:.||||
MUT4    251  NMSRLDVYIAHNPAGTSVQNTLHWRQAVKSGKFQAFDWGSPDQNMKHYHQ    300

WT      301  PTPPIYNLTAMNVPIAVWSADNDLLADPQDVDFLLSKLSNLIYHKEIPNY    350
             .|||.||:|.|.||.||||||||||||||||||||||||||||||||:|
MUT4    301  STPPEYNVTDMKVPTAVWSADNDLLADPQDVDFLLSKLSNLIYHKEIPHY    350

WT      351  NHLDFIWAMDAPQEVYNEIVSLMAEDKK   378
             ||||||||..|||||||||||:.||.||||
MUT4    351  NHLDFIWGEDAPQEVYNEIIRLMKEDKK   378
```

Fig. 3

PREGASTRIC ESTERASE AND DERIVATIVES THEREOF

CROSS REFERENCE TO RELATED APPLICATIONS

This application is a divisional of pending U.S. application Ser. No. 13/203,086 filed Aug. 24, 2011 and which is a §371 National Stage Application of PCT/EP2010/052903 filed Mar. 8, 2010, which claims priority to European Application Nos. 09154780.2 filed Mar. 10, 2009.

FIELD OF THE INVENTION

The present invention relates to novel lipase polynucleotide sequences, their corresponding proteins as well as ways of manufacturing said sequences and said proteins and use of the proteins in the preparation of food compositions. The invention further relates to methods for releasing proteins from the exterior of a host cell as well as to a method for killing micro-organisms.

BACKGROUND OF THE INVENTION

Lipases are enzymes that catalyse the hydrolysis of ester bonds in lipid substrates, leading to the release of fatty acids. Lipases are used in the dairy applications for flavour generation, most importantly in cheese. Traditionally, ruminant lipase preparations are used, derived from goat, kid goat, calf or lamb. These are derived from pregastric tissues from these ruminants and these lipase preparations are also referred to as pregastric esterases. Commercial preparations are in the market, such as the Piccantase® C, L, KG and K (DSM Food Specialties, The Netherlands). These lipases are used in the preparation of a variety of Italian, Spanish, Greek and French cheeses. The development of a specific flavour profile in these types of cheeses during ripening is largely due to the action of lipases on milk fat. Lipases catalyse hydrolysis of milk fat with generation of free fatty acids. Said fatty acids may have short chains (C4-C6 fatty acids, such as containing 4 or 6 carbon atoms, i.e. butyric, caproic acid) and medium to long chain (C12-C18 fatty acids). Subsequently free fatty acids can take part in chemical reactions, e.g. the formation of flavour compounds such as acetoacetate, beta-keto acids, methyl ketons, esters and lactones. Conversion of fatty acids in flavor components can be catalysed by the enzymes originating from the microbial population in cheese.

It is known that the type of free fatty acids released by lipases in cheese can be influenced by the type of lipases used. For example lipases that primarily release short chain fatty acids (e.g. C4 and C6 containing fatty acids) lead to the development of a piquant, sharp, spicy, tangy flavour, while release of medium to long chain fatty acids can lead to a soapy taste. Lipases find increasing use in other dairy applications than cheese, such as Enzyme Modified Cheese (EMC; Wilkinson et al in Encyclopedia of Dairy Sciences, (2003; Fox et all eds, Academic Press) pp. 434-438) or the hydrolysis of butter fat and cream and their applications (Kilara in Enzyclopedia of Dairy Sciences, (2003; Fox et all eds, Academic Press) pp. 914-918).

Ruminant lipases are preferred over microbial lipases because of their specificity to release short chain fatty acids (C4-, C6-fatty acids) from milk fat. These compounds are either flavour compounds themselves or are converted into volatile esters with a particular flavour impact (Liu et al, Int. Dairy J. 2004, 14, 923-945). An interesting issue is the composition of ruminant lipases, which is the topic of several papers (e.g. Addis et al Int. dairy J. (2005) 15, 1271-1278; Richardson et al, J. Dairy Sci. (1967) 50, 1061-1065; Addid et al Int. Dairy J. (2005) 15, 563-569; Hamosh Nutrition (1990) 6, 421-428; Calvo et al (2004) J. Dairy Sci. 87, 1132-1142). The data presented lead to the conclusion that most ruminant enzymes are probably mixtures of 2 or more lipases, and that variations in composition occur leading to changes in performance in cheese flavour formation. This variation is a driver for the industry to look for alternative enzyme sources with improved consistence. The occurrence of animal diseases like scrapie and mad cows disease is another driver for industry to look for alternatives. Further support comes from the desire to have easy access to Kosher and Halal quality products. There is therefore a strong industrial desire for alternatives for animal derived lipases.

Patent application US2004/0001819 described the cloning and expression of kid pregastric esterase in the yeast *Pichia pastoris*. Although potentially interesting, the enzyme is poorly produced and in addition the free fatty acid release profile shifted to longer chain fatty acids, as compared to the original kid goat esterase. These two aspects made this enzyme unattractive because of poor economics and lack of performance in application. A preferred alternative would be microbial lipases or (microbial) lipases recombinantly produced by micro-organisms. Several microbial lipases are in the market (for examples see e.g. Bjurlin et al, JAOCS (2001) 78, 153-160). The most important characteristic of microbial lipases for cheese application is their fatty acid release profile from milk fat, which should mimic as close as possible the animal derived lipases. Microbial lipases are, however, poor performers in this respect since they have a preference for the release of long chain (C12-C18) fatty acids relative to short chain fatty acids (C4, C6). This often leads to the formation of a soapy taste and not to the desired piquant flavour. Therefore, despite the fact that there is a considerable number of commercial microbial lipase preparations in the market there is still an industrial need for a non-animal derived lipase that can replace the animal derived lipases such as ruminant pregastric lipases.

An interesting issue is the composition of the ruminant lipases, also referred to as pregastric esterases. This item is addressed in several papers, and the data that are presented lead to the conclusion that the ruminant enzyme preparations most probably contain a mixture of two or more lipases/esterases. The composition of the ruminant preparations is important for their performance in cheese flavor formation. The mode of action, specificity and flavor effects of various ruminant preparations has been described in various papers.

Several pregastric esterases have been purified and/or cloned, e.g. from kid, goat, calf and lamb. They are similar with respect to physical properties and substrate preference. In general they are glycosylated proteins with a molecular weight between 40-60 kD. The pH optima are in the neutral to slightly acidic region, which is well compatible with the pH found in cheese and EMC. All have a preference for the short chain fatty acids. From some species like lamb, different enzymes are isolated with slight differences in substrate preferences. This supports the view that pregastric esterase preparations may contain multiple lipases. The esterases preferentially release fatty acids from the sn1 or sn3 position from triacyl-glycerides. They are much less active on mono- and di-acylglycerides and phospholipids. This in contrast to many microbial lipases that are well able to degrade di- and monoglycerides and often show activity on phospholipids as well.

The kid goat pregastric esterase has been cloned and heterogeneously expressed in the yeast *Pichia pastoris*. The expression levels are unclear, but the fatty acid release profile was reported. The recombinant enzyme shows a profile that deviates from the kid-derived preparation. The main difference is a lower release of short chain fatty acids for the recombinant enzyme. This finding could point to the multienzyme composition of the pregastric kid lipase. The calf pregastric lipase has been cloned and sequenced (Timmermans M Y, Teuchy H, Kupers L P. *The cDNA sequence of bovine pregastric esterase*. Gene (1994) 147, 259-262), but the efficient, commercial interesting, over-expression of the enzyme has not been described. The lamb pregastric lipase has not been cloned and sequenced.

Several other non-microbial lipases have been cloned, sequenced and characterized. These include several human lipases, rat lipases, pig hepatic lipase, and lipases from cat, dog, guinea pig, mouse, rabbit and tortoise. These have, however, generally not been tested in cheese applications, nor has their substrate specificity been tested towards milk fat. The pregastric esterases are expected to be similar to those of the ruminants. The other, non-pregastric, lipases range in specificity from long chain fatty acids in lipids to true esterases, like the pig liver esterase.

OBJECT OF THE INVENTION

It is the object of the present invention to provide novel lipolytic enzymes which are suitable to be used in, for example, the dairy industry, more particularly in the manufacture of cheese or cheese-like products, in the lipolysis of butter fat or cream or in the production of enzyme-modified cheese. Furthermore, it is an object of the invention to provide novel polynucleotides encoding the novel lipolytic enzymes. A further object is to provide recombinantly produced lipolytic enzymes as well as recombinant strains producing these. Also fusion polypeptides are part of the invention as well as methods of making and using the polynucleotides and polypeptides according to the invention. Yet another object is to provide a method for releasing a produced protein of interest from the exterior (for example the cell wall or cell membrane) of a host cell. A further object is to provide a method for killing host cells.

The DNA EcoRI/SnaBI fragments were made synthetically and included the 3' end of the glaA promoter, the signal sequence or the carrier protein sequence and the PGE-encoding gene. They were inserted in an *A. niger* expression vector digested with EcoRI and SnaBI.

FIG. 2 Amino acid sequence alignment of mature PGE wt (WT) vs. PGE mutant 3 (MUT 3).

The alignment was done using NEEDLE program with EBLOSUM62 substitution matrix with the following settings: a gap-open penalty of 10 and a gap extension penalty of 0.5.

FIG. 3 Amino acid sequence alignment of mature PGE wt (WT) vs. PGE mutant 4 (MUT 4).

The alignment was done using NEEDLE program with EBLOSUM62 substitution matrix with the following settings: a gap-open penalty of 10 and a gap extension penalty of 0.5.

Figure 4:
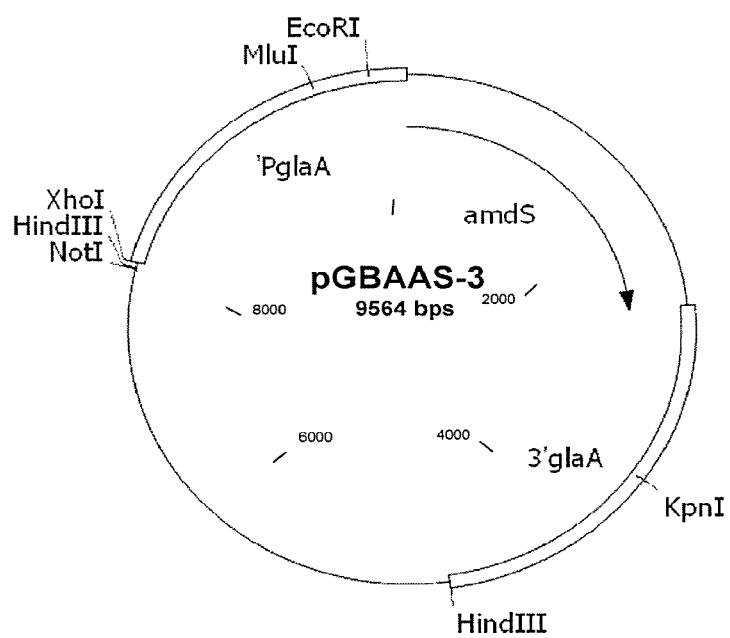

FIG. 4 *A. niger* amdS containing plasmid.

Plasmid for co-transformation of *A. niger* containing the *A. nidulans* selection marker—amdS.

Figure 5:
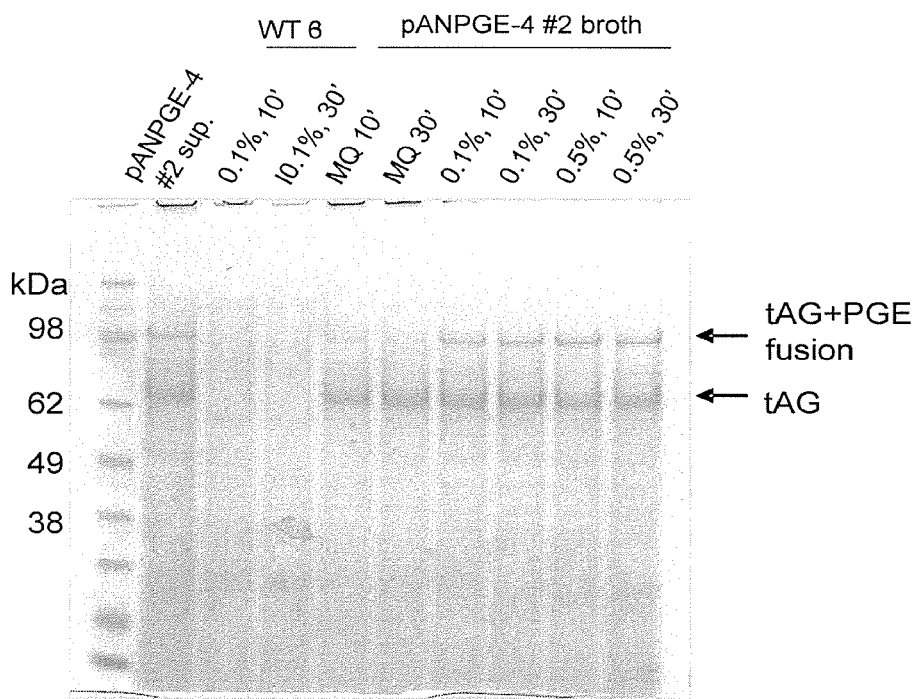

FIG. 5. SDS-PAGE gel of PGE overexpressing transformant pANPGE-4 #2.

The arrow indicates the fusion protein tAG-PGE and the processed tAG. % indicate amount of TritonX-100 (v/v) used to treat the *A. niger* broth (time was 10 or 30 minutes). Second column from left shows the protein in supernatant of the transformant. On the left hand site are the Mw marker sizes in kDa.

Figure 6:
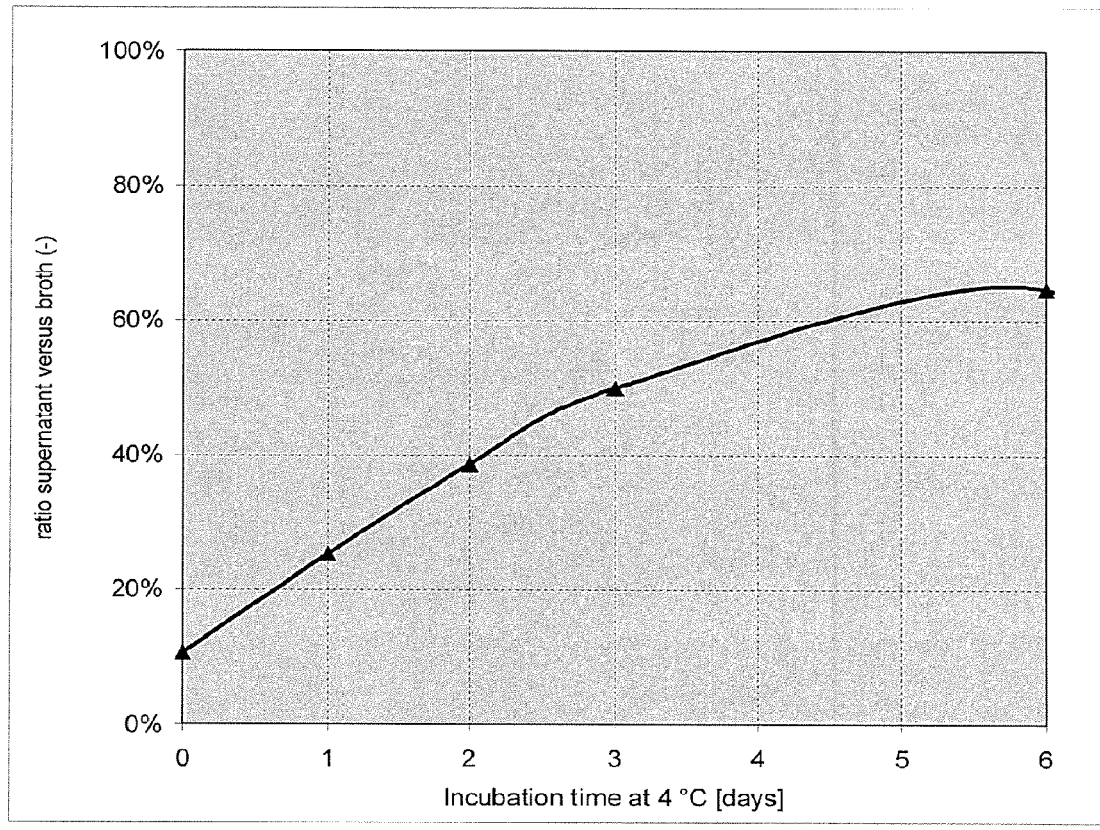

FIG. 6 Release of lipase from host cells.

*K. lactis* broth was at the end of fermentation adjusted to pH 10 during. The activity was measured in supernatant for several days and the ratio of activity in supernatant and broth was calculated.

Figure 7:
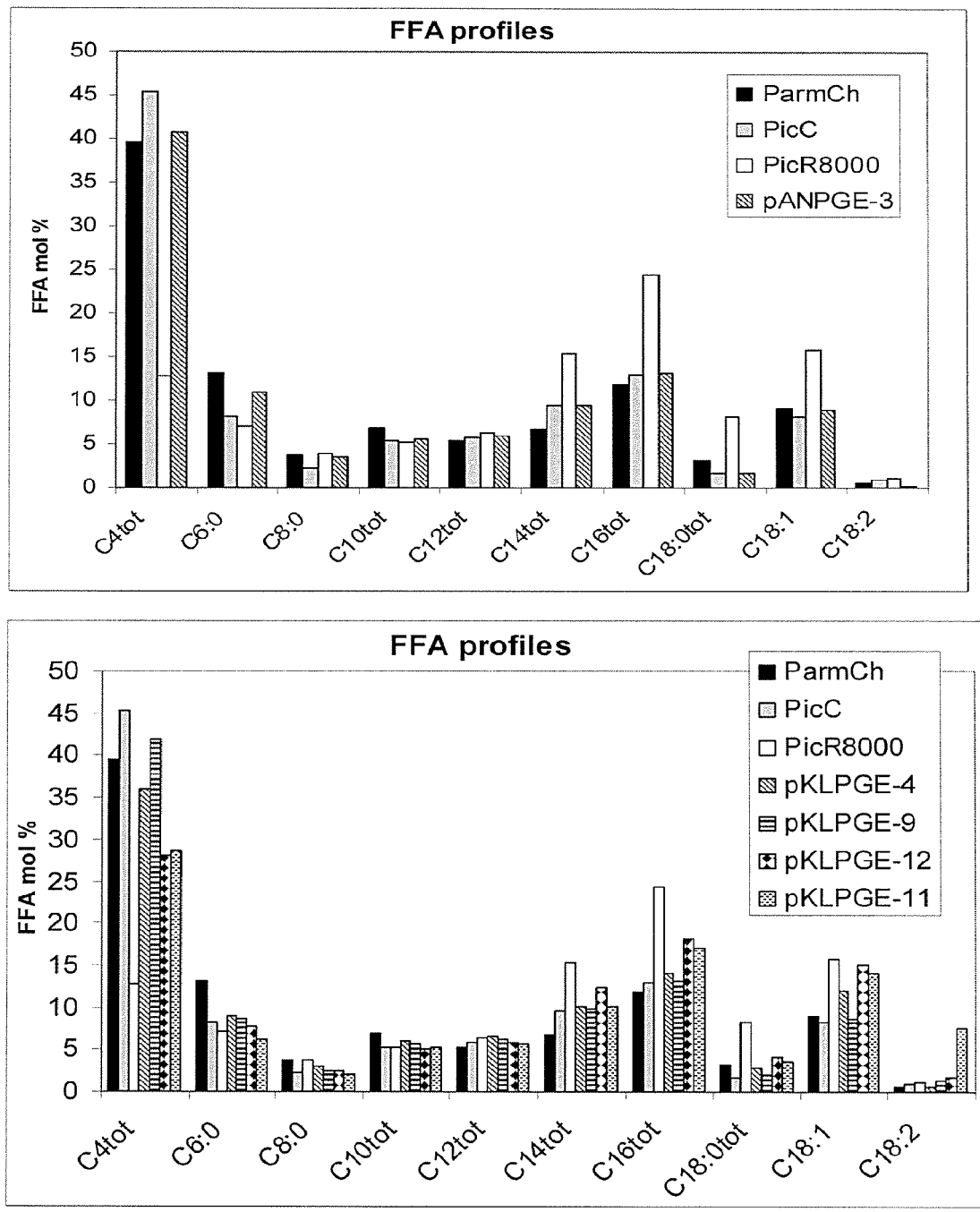

FIG. 7 FFA profiles

Figure 8:
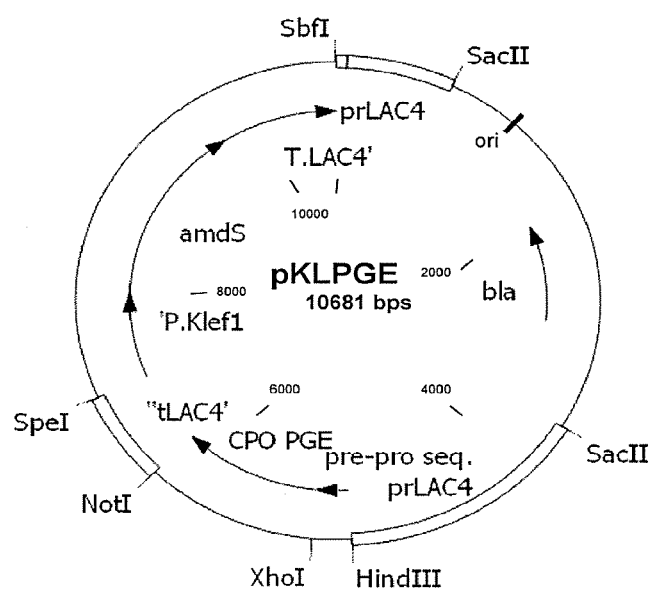

FIG. 8 pKLPGE *K. lactis* expression vector.

The backbone of the vector is formed by the pTZ19R plasmid. The amdS marker is *A. nidulans* amdS cDNA clone. Promoter of the *K. lactis* LAC4 gene (pLAC4) and the LAC4 terminator (tLAC4) are isolated from *K. lactis*. The CPO-PGE gene represents a variant of PGE codon pair optimized gene that is fused to the *K. lactis* pre-pro α-mating factor sequence. To remove the *E. coli* containing part the vector was cut with SacII.

Figure 9:
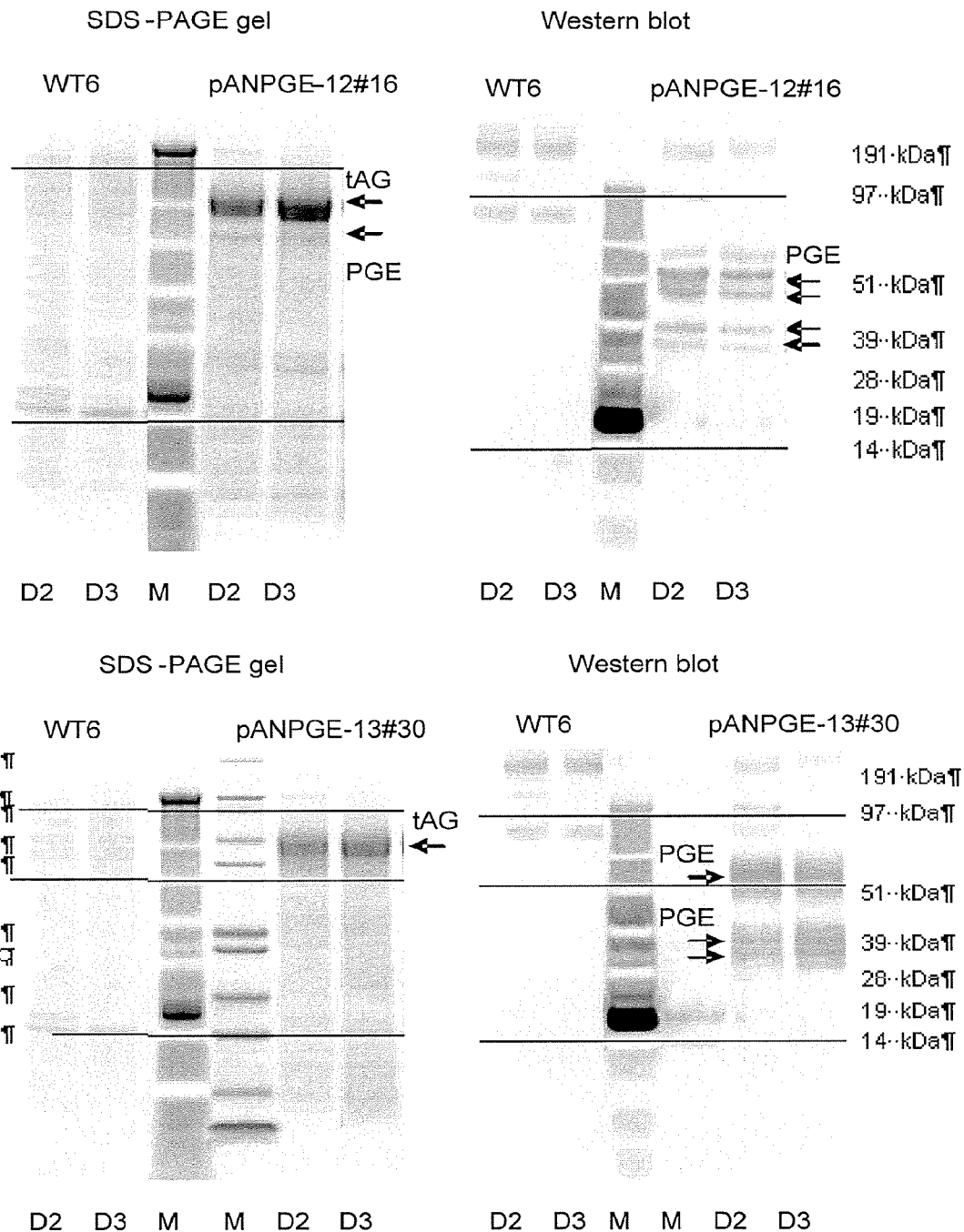

FIG. 9 SDS-PAGE and western blot analysis of *A. niger* WT6 and the PGE mutant transformants pANPGE12#16 and pANPGE13#30.

Supernatant of day 2 (D2) and day 3 (D3) of the cultures was analyzed. The horizontal lines that are at the 14 kDa and 97 kDa are for alignment of the SDS-PAGE and western blot. The marker size on the left-hand side corresponds to the SDS-PAGE stained marker and the marker on the right-hand side corresponds to the western blot marker.

Figure 10:
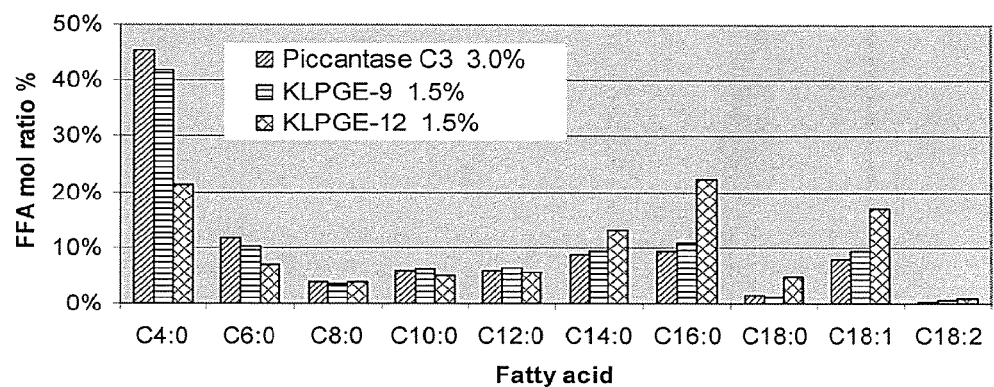

FIG. 10 Free fatty acid (mol %) profile of enzyme treated EMC preparations

Figure 11:
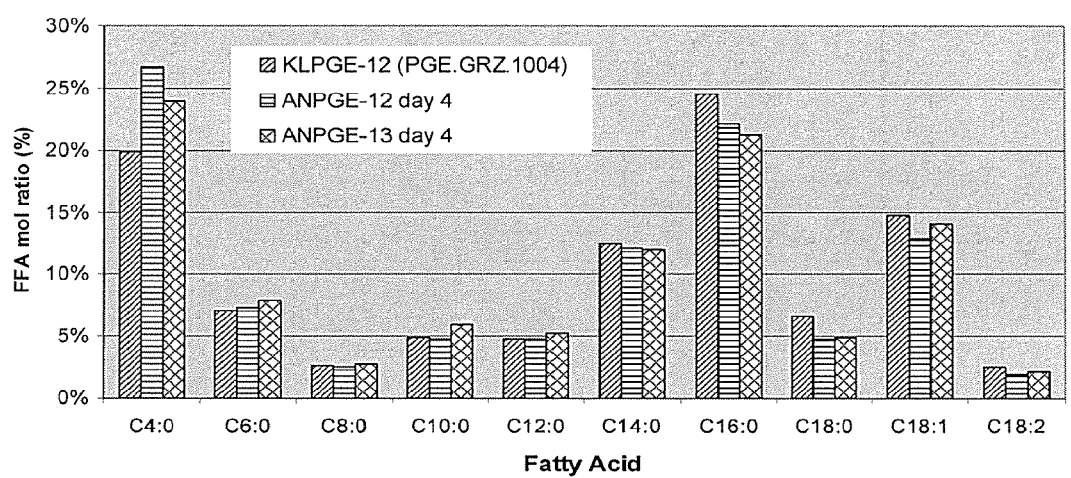

FIG. 11 Free fatty acid (mol %) profile of enzyme treated EMC preparations

DESCRIPTION OF SEQ ID NUMBERS

SEQ ID NO: 1: cDNA codon-pair optimized (CPO) pregastric esterase (PGE) for *K. lactis*; processed, i.e. without signal sequence coding part SEQ ID NO: 2: protein PGE wt with the signal sequence as well as the protein encoded by CPO PGE; the amino acids 1-19 represent the signal sequence and the amino acids 20-397 represent mature PGE SEQ ID NO: 3: bovine/calf cDNA wildtype PGE (excluding signal sequence)

SEQ ID NO: 4: CPO cDNA mutant 1 for expression in *K. lactis* (excluding signal sequence).

SEQ ID NO: 5: protein mutant 1 (lacking signal sequence); also named KLPGE-8 (*K. lactis*)

SEQ ID NO: 6: CPO cDNA mutant 2 for expression in *K. lactis* (excluding signal sequence).

SEQ ID NO: 7: protein mutant 2 (lacking signal sequence); also named KLPGE-9 (*K. lactis*)

SEQ ID NO: 8: CPO cDNA mutant 3 for expression in *K. lactis* (excluding signal sequence).

SEQ ID NO: 9: protein mutant 3 (lacking signal sequence); also named KLPGE-11 (*K. lactis*)

SEQ ID NO: 10: CPO cDNA mutant 4 for expression in *K. lactis* (excluding signal sequence).

SEQ ID NO: 11: protein mutant 4 (lacking signal sequence); also named KLPGE-12 (*K. lactis*)

SEQ ID NO: 12: CPO cDNA mutant 5 for expression in *K. lactis* (excluding signal sequence).

SEQ ID NO: 13: protein mutant 5 (lacking signal sequence); also named KLPGE-10 (*K. lactis*)

SEQ ID NO: 14: DNA CPO signal sequence PGE

SEQ ID NO: 15: CPO PGE for expression in *A. niger* (excluding signal sequence).
SEQ ID NO: 16: CPO cDNA mutant 1 for expression in *A. niger* (excluding signal sequence). The protein encoded by SEQ ID NO. 16 (lacking signal sequence) is also named ANPGE-10 (*A. niger*). The protein is identical to KLPGE-9, SEQ ID NO. 7.
SEQ ID NO: 17: CPO cDNA mutant 2 for expression in *A. niger* (excluding signal sequence).
SEQ ID NO: 18: protein of SEQ ID NO:17 (lacking signal sequence), also named ANPGE-16 (*A. niger*). This protein is in one amino acid different from KLPGE-12, SEQ. ID. NO. 11
SEQ ID NO: 19: CPO cDNA mutant 3 for expression in *A. niger* (excluding signal sequence).
SEQ ID NO: 20: protein of SEQ ID NO. 19 (lacking signal sequence), also named ANPGE-12 (*A. niger*).
SEQ ID NO: 21: CPO cDNA mutant 4 for expression in *A. niger* (excluding signal sequence).
SEQ ID NO: 22: protein of SEQ ID NO. 21 (lacking signal sequence), also named ANPGE-13 (*A. niger*).

SUMMARY OF THE INVENTION

The present invention provides multiple novel lipolytic enzymes which are suitable to be used in, for example, the dairy industry. Surprisingly, the novel lipolytic enzymes are extremely suitable for use in flavour production by enzymatic modification of lipid-containing food ingredients, preferably cheese. The novel lipolytic enzymes can be advantageously used also in cheese ripening, in the manufacture of cheese-like products, in cream or butter fat modification. The enzymes can for example be used to modify butter-fat and use this modified butter-fat to impart flavour to a wide range of processed foods like bakery and confectionery products. Furthermore the enzymes can be suitably used also in other food applications, such as in the manufacture of bakery products. The enzymes of the invention can also be used in the manufacture of a medicament in the treatment of pancreatic insufficiency.

The invention furthermore provides novel polynucleotides encoding novel lipolytic enzymes.

DETAILED DESCRIPTION OF THE INVENTION

Polynucleotides *K. lactis*

The present invention provides in a first aspect an isolated polynucleotide which comprises a nucleotide sequence selected from:
(a) the nucleotide sequence as set out in SEQ ID NO: 1 or a functional equivalent thereof having at least 80% homology to the nucleotide sequence of SEQ ID NO: 1;
(b) a nucleotide sequence which hybridizes with a polynucleotide being the complement of SEQ ID NO: 1 and wherein said nucleotide sequence is at least 80% homologous to the nucleotide sequence of SEQ ID NO: 1;
(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2; or
(d) a nucleotide sequence which is the complement of a nucleotide sequence as defined in (a), (b) or (c),
with the proviso that the isolated polynucleotide is not a wildtype lipase polynucleotide.
SEQ ID NO: 1 shows the nucleotide sequence of a processed (i.e. without a signal sequence), *K. lactis* codon pair optimised, calf pregastric esterase. A calf pregastric esterase was cloned and subsequently subjected to codon pair optimization. The obtained polynucleotide was optimized in its codon use, according to the methods described in WO2006/077258 and/or WO2008/000632. WO2008/000632 addresses codon-pair optimization. Codon-pair optimisation is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence. An alignment of wt and CPO processed PGE cDNA (*K. lactis*) resulted in 78% homology. The corresponding amino acid sequences are 100% identical. An alignment between SEQ ID NO: 1 and unprocessed (i.e. with signal sequence) calf PGE resulted in 74.3% identity.

The functional equivalents of the codon pair optimized pregastric esterase (SEQ ID NO: 1) have at least 80% homology (or identity; the term are used interchangeably herein) to SEQ ID NO: 1. The original, i.e. wildtype, pregastric esterase (PGE) nucleotide sequences, such as SEQ ID NO: 3, are explicitly disclaimed. The functional equivalents are different from the original, wildtype PGE nucleotide sequences. More in specific the functional equivalents are different from (or alternatively, are not identical to) the wildtype PGE cDNA.

The term "having at least xx % (for example 80%) homology" refers to homology of the encoded processed protein, i.e. said % homology is determined on the % homology within mature protein. Or alternatively, upstream and downstream sequences (such as polynucleotides encoding a signal sequence, promoter sequences or terminator sequence) are excluded in this term. For example, if one would like to determine whether a sequence A which sequence A comprises promoter, signal sequence, mature protein and terminator parts is at least 80% homologous to SEQ ID NO: 1 only the polynucleotides encoding the mature protein of sequence A must be compared to SEQ ID NO:1. In a preferred embodiment, the invention provides an isolated polynucleotide which comprises a nucleotide sequence selected from:
(a) the nucleotide sequence as set out in SEQ ID NO: 1 or a functional equivalent thereof having at least 80% homology to the nucleotide sequence of SEQ ID NO: 1;
(b) a nucleotide sequence which hybridizes with a polynucleotide being the complement of SEQ ID NO: 1 and wherein said nucleotide sequence is at least 80% homologous to the nucleotide sequence of SEQ ID NO: 1;
(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2; or
(d) a nucleotide sequence which is the complement of a nucleotide sequence as defined in (a), (b) or (c),
with the proviso that the isolated polynucleotide is not a wildtype lipase polynucleotide and
wherein said percentage homology is determined by exclusively comparing mature protein encoding nucleotides or by comparing mature protein sequences.

In respect of SEQ ID NO: 1 this means that additional sequences located upstream of downstream of 1 to 1137 are not relevant for determining the percentage of homology. In respect of SEQ ID NO: 2 this means that additional sequences at the N-terminus or C-terminus are not relevant for determining percentage of identity.

Moreover, polynucleotide sequences resulting in an amino acid sequence having at least 85% homology to the polypeptide of SEQ ID NO: 2 and comprising mutation:

SerxxxAsn which Ser in SEQ ID NO: 2 is located at position 184 (i.e. xxx=184; Ser184Asn with respect to SEQ ID NO: 2) or comprising mutation:

PheyyyLeu which Phe in SEQ ID NO: 2 is located at position 352 (i.e. yyy=352; Phe352Leu with respect to SEQ ID NO: 2) are explicitly excluded.

Furthermore, polynucleotides sequences resulting in an amino acid sequence having at least 85% homology to the polypeptide in SEQ ID NO:2 and comprising only 2 mutations at the amino acid sequence level which 2 amino acid sequence mutations are:

SerxxxAsn which Ser in SEQ ID NO: 2 is located at position 184 (i.e. xxx=184; Ser184Asn with respect to SEQ ID NO: 2) and:

PheyyyLeu which Phe in SEQ ID NO: 2 is located at position 352 (i.e. yyy=352; Phe352Leu with respect to SEQ ID NO: 2) are explicitly excluded.

In another embodiment, the present invention provides polynucleotides encoding lipolytic enzymes, having an amino acid sequence corresponding to the mature polypeptide in the amino acid sequence according to SEQ ID NO: 2 or functional equivalents having at least 85% homology to the amino acid sequence corresponding to the mature polypeptide in the amino acid sequence according to SEQ ID NO: 2.

In the context of the present invention "mature polypeptide" is defined herein as a polypeptide having lipolytic activity that is in its final form following translation and any post-translational modifications, such as N-terminal processing, C-terminal truncation, glycosylation, phosphorylation, etc. The process of maturation may depend on the particular expression vector used, the expression host and the production process. Preferably, the mature polypeptide is represented by amino acids 20 to 379 in the amino acid sequence according to SEQ ID NO: 2. A "nucleotide sequence encoding the mature polypeptide" is defined herein as the polynucleotide sequence which codes for the mature polypeptide. Preferably the nucleotide sequence encoding the mature polypeptide is represented by nucleotides 1 to 1137 in SEQ ID NO: 1.

The invention provides polynucleotide sequences comprising the gene encoding the lipolytic enzyme. Accordingly, the invention relates to an isolated polynucleotide comprising the nucleotide sequence according to SEQ ID NO: 1 or to variants such as functional equivalents thereof having at least 80% homology to SEQ ID NO: 1.

In particular, the invention relates to an isolated polynucleotide comprising a nucleotide sequence which hybridises, preferably under stringent conditions, more preferably under highly stringent conditions, to the complement of a polynucleotide according to SEQ ID NO: 1 and wherein preferably said sequence is at least 80% homologous to the nucleotide sequence of SEQ ID NO: 1.

More specifically, the invention relates to an isolated polynucleotide comprising or consisting essentially of a nucleotide sequence according to SEQ ID NO: 1, 4, 6, 8, 10 or 12.

Such isolated polynucleotide may be obtained by synthesis with methods known to the person skilled in the art.

As used herein, the terms "gene" and "recombinant gene" refer to nucleic acid molecules which may be isolated from chromosomal DNA, which include an open reading frame encoding a protein, e.g. a lipolytic enzyme. A gene may include coding sequences, non-coding sequences, introns and regulatory sequences. Moreover, a gene refers to an isolated nucleic acid molecule or polynucleotide as defined herein.

A nucleic acid molecule of the present invention, such as a nucleic acid molecule having the nucleotide sequence of SEQ ID NO: 1 or a functional equivalent thereof, can be obtained by performing codon pair optimization on the wildtype PGE cDNA and further by using standard cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to the complement of the nucleotide sequences according to the invention can be prepared by standard synthetic techniques, e.g., using an automated DNA synthesizer. The invention therefore also provides an isolated polynucleotide which comprises a nucleotide sequence selected from:

(a) the nucleotide sequence as set out in SEQ ID NO: 1 or a functional equivalent thereof having at least 80% homology to the nucleotide sequence of SEQ ID NO: 1;

(b) a nucleotide sequence which hybridizes with a polynucleotide being the complement of SEQ ID NO: 1 and wherein said nucleotide sequence is at least 80% homologous to the nucleotide sequence of SEQ ID NO: 1;

(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2;

(d) a nucleotide sequence which is the complement of a nucleotide sequence as defined in (a), (b) or (c), wherein said polynucleotide is produced synthetically, with the proviso that the isolated polynucleotide is not a wildtype lipase polynucleotide, such as for example SEQ ID NO:3.

In a preferred embodiment, an isolated nucleic acid molecule of the invention comprises the nucleotide sequence according to SEQ ID NO: 1. The sequence of SEQ ID NO: 1 encodes the polypeptide according to amino acids 20-397 of SEQ ID NO: 2 and the lypolitic enzyme according to the mature polypeptide in SEQ ID NO: 2. Therefore the invention provides a polynucleotide as described above which encodes for a lipolytic enzyme.

In another preferred embodiment, an isolated nucleic acid molecule of the invention comprises a nucleic acid molecule which is a complement of the nucleotide sequence shown in SEQ ID NO: 1 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a variant, such as a functional equivalent thereof, for example a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a nucleic acid molecule according to the invention, e.g., the coding strand of a nucleic acid molecule according to the invention.

Also included within the scope of the invention are the complement strands of the polynucleotides according to the invention.

In yet another aspect the invention provides an isolated polynucleotide which comprises a nucleotide sequence selected from:
(a) the nucleotide sequence as set out in SEQ ID NO: 1 or a functional equivalent thereof having at least 80% homology to the nucleotide sequence of SEQ ID NO: 1;
(b) a nucleotide sequence which hybridizes with a polynucleotide being the complement of SEQ ID NO: 1 and wherein said nucleotide sequence is at least 80% homologous to the nucleotide sequence of SEQ ID NO: 1;
(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2;
(d) a nucleotide sequence which is the complement of a nucleotide sequence as defined in (a), (b) or (c),
wherein said polyncucleotide further comprising a nucleotide sequence encoding a lipase signal sequence
with the proviso that the isolated polynucleotide is not a wildtype lipase polynucleotide.

Preferably said nucleotide sequence encoding a lipase signal sequence comprises SEQ ID NO: 14.

Polynucleotides *A. niger*

The present invention provides in another aspect an isolated polynucleotide which comprises a nucleotide sequence selected from:
(a) the nucleotide sequence as set out in SEQ ID NO: 15 or a functional equivalent thereof having at least 80% homology to the nucleotide sequence of SEQ ID NO: 15;
(b) a nucleotide sequence which hybridizes with a polynucleotide being the complement of SEQ ID NO: 15 and wherein said nucleotide sequence is at least 80% homologous to the nucleotide sequence of SEQ ID NO: 15;
(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2; or
(d) a nucleotide sequence which is the complement of a nucleotide sequence as defined in (a), (b) or (c),
with the proviso that the isolated polynucleotide is not a wildtype lipase polynucleotide.

SEQ ID NO: 15 shows the nucleotide sequence of a processed (i.e. without a signal sequence), *A. niger* codon pair optimised, calf pregastric esterase. A calf pregastric esterase was cloned and subsequently subjected to codon pair optimization. The obtained polynucleotide was optimized in its codon use as described above in the section polynucleotides *K. lactis*. An alignment of wt and CPO processed PGE cDNA for *A. niger* resulted in 78.6% homology. The corresponding amino acid sequences are 100% identical. An alignment between SEQ ID NO: 15 and unprocessed (i.e. with signal sequence) calf PGE (wild type) resulted in 74.8% identity.

The functional equivalents of the codon pair optimized pregastric esterase (SEQ ID NO: 15) have at least 80% homology (or identity; the term are used interchangeably herein) to SEQ ID NO: 15. The original, i.e. wildtype, pregastric esterase (PGE) nucleotide sequences, such as SEQ ID NO: 3, are explicitly disclaimed. The functional equivalents are different from the original, wildtype PGE nucleotide sequences. More in specific the functional equivalents are different from (or alternatively, are not identical to) the wildtype PGE cDNA.

The term "having at least xx % (for example 80%) homology" refers to homology of the encoded processed protein, i.e. said % homology is determined on the % homology within mature protein. Or alternatively, upstream and downstream sequences (such as polynucleotides encoding a signal sequence, promoter sequences or terminator sequence) are excluded in this term. For example, if one would like to determine whether a sequence A, which sequence A comprises promoter, signal sequence, mature protein and terminator parts, is at least 80% homologous to SEQ ID NO: 15 only the polynucleotides encoding the mature protein of sequence A must be compared to SEQ ID NO:15. In a preferred embodiment, the invention provides an isolated polynucleotide which comprises a nucleotide sequence selected from:
(a) the nucleotide sequence as set out in SEQ ID NO: 15 or a functional equivalent thereof having at least 80% homology to the nucleotide sequence of SEQ ID NO: 15;
(b) a nucleotide sequence which hybridizes with a polynucleotide being the complement of SEQ ID NO: 15 and wherein said nucleotide sequence is at least 80% homologous to the nucleotide sequence of SEQ ID NO: 15;
(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2; or
(d) a nucleotide sequence which is the complement of a nucleotide sequence as defined in (a), (b) or (c),
with the proviso that the isolated polynucleotide is not a wildtype lipase polynucleotide and
wherein said percentage homology is determined by exclusively comparing mature protein encoding nucleotides or by comparing mature protein sequences.

In respect of SEQ ID NO: 15 this means that additional sequences located upstream of downstream of 1 to 1137 are not relevant for determining the percentage of homology. In respect of SEQ ID NO: 2 this means that additional sequences at the N-terminus or C-terminus are not relevant for determining percentage of identity.

Moreover, polynucleotide sequences resulting in an amino acid sequence having at least 80% homology to the polypeptide of SEQ ID NO: 2 and comprising mutation:

SerxxxAsn which Ser in SEQ ID NO: 2 is located at position 184 (i.e. xxx=184; Ser184Asn with respect to SEQ ID NO: 2) or comprising mutation:

PheyyyLeu which Phe in SEQ ID NO: 2 is located at position 352 (i.e. yyy=352; Phe352Leu with respect to SEQ ID NO: 2) are explicitly excluded.

Furthermore, polynucleotides sequences resulting in an amino acid sequence having at least 80% homology to the polypeptide in SEQ ID NO:2 and comprising only 2 mutations at the amino acid sequence level which 2 amino acid sequence mutations are:

SerxxxAsn which Ser in SEQ ID NO: 2 is located at position 184 (i.e. xxx=184; Ser184Asn with respect to SEQ ID NO: 2) and:

PheyyyLeu which Phe in SEQ ID NO: 2 is located at position 352 (i.e. yyy=352; Phe352Leu with respect to SEQ ID NO: 2) are explicitly excluded.

In another embodiment, the present invention provides polynucleotides encoding lipolytic enzymes, having an amino acid sequence corresponding to the mature polypeptide in the amino acid sequence according to SEQ ID NO: 2 or functional equivalents having at least 80% homology to the amino acid sequence corresponding to the mature polypeptide in the amino acid sequence according to SEQ ID NO: 2.

In the context of the present invention "mature polypeptide" is defined herein as a polypeptide having lipolytic activity that is in its final form following translation and any post-translational modifications, such as N-terminal processing, C-terminal truncation, glycosylation, phosphorylation, etc. The process of maturation may depend on the particular expression vector used, the expression host and the production process. Preferably, the mature polypeptide is represented by amino acids 20 to 379 in the amino acid sequence according to SEQ ID NO: 2. A "nucleotide sequence encoding the mature polypeptide" is defined herein as the polynucleotide sequence which codes for the mature polypeptide. Preferably the nucleotide sequence encoding the mature polypeptide is represented by nucleotides 1 to 1137 in SEQ ID NO: 15.

The invention provides polynucleotide sequences comprising the gene encoding the lipolytic enzyme. Accordingly, the invention relates to an isolated polynucleotide comprising the nucleotide sequence according to SEQ ID NO: 15 or to variants such as functional equivalents thereof having at least 80% homology to SEQ ID NO: 15.

In particular, the invention relates to an isolated polynucleotide comprising a nucleotide sequence which hybridises, preferably under stringent conditions, more preferably under highly stringent conditions, to the complement of a polynucleotide according to SEQ ID NO: 15 and wherein preferably said sequence is at least 80% homologous to the nucleotide sequence of SEQ ID NO: 15.

More specifically, the invention relates to an isolated polynucleotide comprising or consisting essentially of a nucleotide sequence according to SEQ ID NO: 16, 17, 19 or 21.

Such isolated polynucleotide may be obtained by synthesis with methods known to the person skilled in the art.

The terms "gene" and "recombinant gene" are explained in the above section (polynucleotides *K. lactis*) and apply also to the *A. niger* section.

A nucleic acid molecule of the present invention, such as a nucleic acid molecule having the nucleotide sequence of SEQ ID NO: 15 or a functional equivalent thereof, can be obtained by performing codon pair optimization on the wildtype PGE cDNA and further by using standard cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Furthermore, oligonucleotides corresponding to or hybridisable to the complement of the nucleotide sequences according to the invention can be prepared by standard synthetic techniques, e.g., using an automated DNA synthesizer. The invention therefore also provides an isolated polynucleotide which comprises a nucleotide sequence selected from:
(a) the nucleotide sequence as set out in SEQ ID NO: 15 or a functional equivalent thereof having at least 80% homology to the nucleotide sequence of SEQ ID NO: 15;
(b) a nucleotide sequence which hybridizes with a polynucleotide being the complement of SEQ ID NO: 15 and wherein said nucleotide sequence is at least 80% homologous to the nucleotide sequence of SEQ ID NO: 15;
(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2;
(d) a nucleotide sequence which is the complement of a nucleotide sequence as defined in (a), (b) or (c),
wherein said polynucleotide is produced synthetically,
with the proviso that the isolated polynucleotide is not a wildtype lipase polynucleotide, such as for example SEQ ID NO:3.

In a preferred embodiment, an isolated nucleic acid molecule of the invention comprises the nucleotide sequence according to SEQ ID NO: 15. The sequence of SEQ ID NO: 15 encodes the polypeptide according to amino acids 20-397 of SEQ ID NO: 2 and the lypolitic enzyme according to the mature polypeptide in SEQ ID NO: 2. Therefore the invention provides a polynucleotide as described above which encodes for a lipolytic enzyme.

In another preferred embodiment, an isolated nucleic acid molecule of the invention comprises a nucleic acid molecule which is a complement of the nucleotide sequence shown in SEQ ID NO: 15 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a variant, such as a functional equivalent thereof, for example a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

The terms "isolated polynucleotide" or "isolated nucleic acid" are explained ion the above section (polynucleotides *K. lactis* and also apply to the *A. niger* section.

The terms "polynucleotide" or "nucleic acid molecule" are explained in the above section (polynucleotides *K. lactis* and also apply to the *A. niger* section.

Another embodiment of the invention provides an isolated nucleic acid molecule which is antisense to a nucleic acid molecule according to the invention, e.g., the coding strand of a nucleic acid molecule according to the invention.

Also included within the scope of the invention are the complement strands of the polynucleotides according to the invention.

In yet another aspect the invention provides an isolated polynucleotide which comprises a nucleotide sequence selected from:
(a) the nucleotide sequence as set out in SEQ ID NO: 15 or a functional equivalent thereof having at least 80% homology to the nucleotide sequence of SEQ ID NO: 15;
(b) a nucleotide sequence which hybridizes with a polynucleotide being the complement of SEQ ID NO: 15 and wherein said nucleotide sequence is at least 80% homologous to the nucleotide sequence of SEQ ID NO: 15;
(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2;
(d) a nucleotide sequence which is the complement of a nucleotide sequence as defined in (a), (b) or (c),
wherein said polynucleotide further comprising a nucleotide sequence encoding a lipase signal sequence
with the proviso that the isolated polynucleotide is not a wildtype lipase polynucleotide.

Preferably said nucleotide sequence encoding a lipase signal sequence comprises SEQ ID NO: 14.

Nucleic Acid Fragments, Probes and Primers

A nucleic acid molecule according to the invention may comprise only a portion or a fragment of the nucleic acid sequence according to SEQ ID NO: 1, 4, 6, 8, 10, 15, 16, 17, 19 or 21 for example a fragment which can be used as a probe or primer or a fragment encoding a portion of the protein according to the invention. The nucleotide sequence according to the invention allows for the generation of probes and primers designed for use in identifying and/or cloning functional equivalents of the protein according to the invention having at least 80 or 85% homology to the protein according to SEQ ID NO: 2. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence according to the invention.

Probes based on the nucleotide sequences according to the invention, more preferably based on SEQ ID NO: 1, 4, 6, 8, 10, 15, 16, 17, 19 or 21 can be used to detect transcripts or genomic sequences encoding the same or homologous proteins for instance in organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express a protein according to the invention.

Identity & Homology

The terms "homology" or "percent identity" are used interchangeably herein. For the purpose of this invention, it is defined here that in order to determine the percent homology of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277. For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms. After alignment by the program NEEDLE as described above the percentage of identity between a query sequence and a sequence of the invention is calculated as follows: Number of corresponding positions in the alignment showing an identical amino acid or identical nucleotide in both sequences divided by the total length of the alignment after substraction of the total number of gaps in the alignment. The identity defined as herein can be obtained from NEEDLE by using the NOBRIEF option and is labelled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

As an example, the following tables provide an overview of the homology and identity percentages (%) at the polynucleotide (Table 1), signal sequences (Table 2) and amino acid (Table 3) level between *K. lactis* codon pair optimised (CPO) processed PGE and 5 different mutants (calculated via NEEDLE with parameter settings as described above). The different mutants will be discussed in more detail later on.

TABLE 1

| cDNA (processed) | CPO PGE |
| --- | --- |
| CPO PGE (SEQ ID NO: 1) | 100% |
| Mutant 1 (SEQ ID NO: 4) | 91.4% |
| Mutant 2 (SEQ ID NO: 6) | 90.7% |
| Mutant 3 (SEQ ID NO: 8) | 87.5% |
| Mutant 4 (SEQ ID NO: 10) | 84.1% |
| Mutant 5 (SEQ ID NO: 12) | 91.7% |

TABLE 2

| Signal sequence DNA | PGE wt |
| --- | --- |
| PGE wt (SEQ ID NO: 23) | 100% |
| Mutant 5 (SEQ ID NO: 14) | 78.9% |

TABLE 3

| Protein (processed) | CPO PGE |
| --- | --- |
| CPO PGE (SEQ ID NO: 2) | 100% |
| Mutant 1 (SEQ ID NO: 5) | 99.7% |
| Mutant 2 (SEQ ID NO: 7) | 98.1% |
| Mutant 3 (SEQ ID NO: 9) | 92.9% |
| Mutant 4 (SEQ ID NO: 11) | 87.3% |
| Mutant 5 (SEQ ID NO: 13) | 100% |

An alignment of PGE CPO cDNA for *A. niger* versus PGE CPO cDNA for *K. lactis* resulted in a 78.9% match (Needle program, Gap_penalty: 10.0 and extend_penalty: 0.5). The invention therefore also provides an isolated polynucleotide which comprises:
(a) the nucleotide sequence as set out in SEQ ID NO: 1 or a functional equivalent thereof having at least 75% homology to the nucleotide sequence of SEQ ID NO: 1;
(b) a nucleotide sequence which hybridizes with a polynucleotide being the complement of SEQ ID NO: 1 and wherein said nucleotide sequence is at least 80% homologous to the nucleotide sequence of SEQ ID NO: 1;
(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2;
(d) a nucleotide sequence which is the complement of a nucleotide sequence as defined in (a), (b) or (c),
with the proviso that the isolated polynucleotide is not a wildtype lipase polynucleotide.

In an even more preferred embodiment, said functional equivalent is expressed in an *Aspergillus* host cell (for example *A. niger*). In one of its aspect the percentage homology is between 75 and 80% or more preferred between 76 and 80% or between 77 and 80% or between 78 and 80% or between 78 and 79%. Preferably said functional equivalent comprises SEQ ID NO: 15.

Alternatively, the invention provides an isolated polynucleotide which comprises:
(a) the nucleotide sequence as set out in SEQ ID NO: 15 or a functional equivalent thereof having at least 80% homology to the nucleotide sequence of SEQ ID NO: 15;
(b) a nucleotide sequence which hybridizes with a polynucleotide being the complement of SEQ ID NO: 15 and wherein said nucleotide sequence is at least 80% homologous to the nucleotide sequence of SEQ ID NO: 15;
(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2;
(d) a nucleotide sequence which is the complement of a nucleotide sequence as defined in (a), (b) or (c),
with the proviso that the isolated polynucleotide is not a wildtype lipase polynucleotide.

As another example, the following tables provide an overview of the homology and identity percentages (%) at the polynucleotide (Table 4) and amino acid (Table 5) level between *A. niger* codon pair optimised (CPO) processed PGE and 4 different mutants (calculated via NEEDLE with parameter settings as described above). The different mutants are briefly described and will be discussed in more detail later on.

PGE mutants for expression in *A. niger*
Mutant 1=overglycosylation variant (ANPGE-10=KLPGE-9 (SEQ ID NO:7))
Mutant 2=hydrophobicity variant (ANPGE-16 (SEQ ID NO:18); 1 amino acid difference compared to KLPGE-12 (SEQ ID NO:11))
Mutant 3=pI mutant (ANPGE-12 (SEQ ID NO:20))
Mutant 4=pI mutant (ANPGE-13 (SEQ ID NO:22))

TABLE 4

| cDNA (processed) | CPO PGE |
| --- | --- |
| CPO PGE (SEQ ID NO: 15) | 100% |
| Mutant 1 (SEQ ID NO: 16) | 91.3% |
| Mutant 2 (SEQ ID NO: 17) | 85.4% |
| Mutant 3 (SEQ ID NO: 19) | 86.3% |
| Mutant 4 (SEQ ID NO: 21) | 84% |

TABLE 5

| Protein (processed) | CPO PGE |
| --- | --- |
| CPO PGE (SEQ ID NO: 2) | 100% |
| Mutant 1 (SEQ ID NO: 7) | 98.1% |
| Mutant 2 (SEQ ID NO: 18) | 87% |
| Mutant 3 (SEQ ID NO: 20) | 87.8% |
| Mutant 4 (SEQ ID NO: 22) | 83.1% |

Hybridisation

As used herein, the term "hybridizing" is intended to describe conditions for hybridization and washing under which nucleotide sequences at least about 60%, 65%, 80%, 85%, 90%, preferably at least 93%, more preferably at least 95% and most preferably at least 98% homologous to each other typically remain hybridized to the complement of each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-standed cDNA clone).

In one of its embodiments, the invention provides a polynucleotide as described herein, which hybridises under high stringency conditions with a nucleotide sequence being the complement of SEQ ID NO: 1 or SEQ ID NO:15.

Production of a Polynucleotide as Described Herein

In yet another embodiment, the invention provides a method for manufacturing a polynucleotide as described herein or a vector as described herein comprising the steps of culturing a host cell transformed with said polynucleotide or said vector and isolating said polynucleotide or said vector from said host cell. Such a polynucleotide or vector is useful in performing cloning steps and/or analysis. Such a method is for example useful for obtaining large amounts of polynucleotides or vector and can alternatively be phrased as a method for multiplying a polynucleotide or a vector as described herein.

Obtaining Full Length DNA from Other Organisms

In a typical approach, cDNA libraries constructed from other organisms, e.g. a mammal can be screened. For example, mammals can be screened for homologous polynucleotides with respect to SEQ ID NO: 1 or SEQ ID NO: 15, by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a polynucleotide according to the invention. Examples of suitable mammals are goat, kid goat, calf and lamb.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new nucleic acid sequence according to the invention, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Full-length cDNA can also be obtained synthetically based on publicly available sequences and optionally CPO amended with respect to the used host cell.

Vectors

Another aspect of the invention pertains to vectors, including cloning and expression vectors, comprising a polynucleotide sequence according to the invention encoding a polypeptide having lipolytic activity or a functional equivalent thereof according to the invention. The invention also pertains to methods of growing, transforming or transfecting such vectors in a suitable host cell, for example under conditions in which expression of a polypeptide of the invention occurs. As used herein, the term "vector" refers to a nucleic acid molecule capable of transporting another nucleic acid to which it has been linked.

The invention thus also provides a vector comprising a polynucleotide sequence as described herein, i.e. an isolated polynucleotide which comprises a nucleotide sequence selected from:

(a) the nucleotide sequence as set out in SEQ ID NO: 1 or a functional equivalent thereof having at least 75 or preferably at least 80% homology to the nucleotide sequence of SEQ ID NO: 1;

(b) a nucleotide sequence which hybridizes with a polynucleotide being the complement of SEQ ID NO: 1 and wherein said nucleotide sequence is at least 75% or preferably at least 80% homologous to the nucleotide sequence of SEQ ID NO: 1;

(c) a nucleotide sequence encoding the polypeptide comprising the amino acid sequence according to SEQ ID NO: 2 or a functional equivalent thereof having at least 85% homology to the polypeptide in the amino acid sequence of SEQ ID NO: 2;

(d) a nucleotide sequence which is the complement of a nucleotide sequence as defined in (a), (b) or (c), with the proviso that the isolated polynucleotide is not a wildtype lipase polynucleotide.

The invention further provides a vector comprising a polynucleotide sequence as described herein, i.e. an isolated polynucleotide which comprises a nucleotide sequence selected from:

(a) the nucleotide sequence as set out in SEQ ID NO: 15 or a functional equivalent thereof having at least 80% homology to the nucleotide sequence of SEQ ID NO: 15;

(b) a nucleotide sequence which hybridizes with a polynucleotide being the complement of SEQ ID NO: 15 and wherein said nucleotide sequence is at least 80% homologous to the nucleotide sequence of SEQ ID NO: 15;

(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2;
(d) a nucleotide sequence which is the complement of a nucleotide sequence as defined in (a), (b) or (c),
with the proviso that the isolated polynucleotide is not a wildtype lipase polynucleotide.

Polynucleotides of the invention can be incorporated into a recombinant replicable vector, for example a cloning or expression vector. The vector may be used to replicate the nucleic acid in a compatible host cell. Thus in a further embodiment, the invention provides a method of making polynucleotides of the invention by introducing a polynucleotide of the invention into a replicable vector, introducing the vector into a compatible host cell, and growing the host cell under conditions which bring about replication of the vector. The vector may be recovered from the host cell. Suitable host cells are described below.

The vector into which the expression cassette or polynucleotide of the invention is inserted may be any vector which may conveniently be subjected to recombinant DNA procedures, and the choice of the vector will often depend on the host cell into which it is to be introduced.

A vector according to the invention may be an autonomously replicating vector, i. e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated.

One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as cosmid, viral vectors (e.g., replication defective retroviruses, adenoviruses and adeno-associated viruses) and phage vectors which serve equivalent functions.

Vectors according to the invention may be used in vitro, for example for the production of RNA or used to transfect or transform a host cell.

A vector of the invention may comprise two or more, for example three, four or five, polynucleotides of the invention, for example for overexpression.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operably linked to the nucleic acid sequence to be expressed.

The invention further provides a vector which is an expression vector wherein the polynucleotide sequence as described herein is operably linked with at least one, optionally additional, regulatory sequence allowing for expression of the polynucleotide sequence in a suitable host cell.

Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell), i.e. the term "operably linked" refers to a juxtaposition wherein the components described are in a relationship permitting them to function in their intended manner. A regulatory sequence such as a promoter, enhancer or other expression regulation signal "operably linked" to a coding sequence is positioned in such a way that expression of the coding sequence is achieved under condition compatible with the control sequences or the sequences are arranged so that they function in concert for their intended purpose, for example transcription initiates at a promoter and proceeds through the DNA sequence encoding the polypeptide.

The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990).

The term regulatory sequences includes those sequences which direct constitutive expression of a nucleotide sequence in many types of host cells and those which direct expression of the nucleotide sequence only in a certain host cell (e.g. tissue-specific regulatory sequences).

A vector or expression construct for a given host cell may thus comprise the following elements operably linked to each other in a consecutive order from the 5'-end to 3'-end relative to the coding strand of the sequence encoding the polypeptide of the first invention: (1) a promoter sequence capable of directing transcription of the nucleotide sequence encoding the polypeptide in the given host cell; (2) optionally, a signal sequence capable of directing secretion of the polypeptide from the given host cell into a culture medium or a carrier protein such as truncated glucoamylase; (3) a DNA sequence of the invention encoding a mature and preferably active form of a polypeptide having lipolytic activity according to the invention; and preferably also (4) a transcription termination region (terminator) capable of terminating transcription downstream of the nucleotide sequence encoding the polypeptide.

Downstream of the nucleotide sequence according to the invention there may be a 3' untranslated region containing one or more transcription termination sites (e.g. a terminator). The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). In the transcribed region, a ribosome binding site for translation may be present. The coding portion of the mature transcripts expressed by the constructs will include a translation initiating AUG at the beginning and a termination codon appropriately positioned at the end of the polypeptide to be translated.

Enhanced expression of the polynucleotide of the invention may also be achieved by the selection of heterologous regulatory regions, e.g. promoter, secretion leader and/or terminator regions, which may serve to increase expression and, if desired, secretion levels of the protein of interest from the expression host and/or to provide for the inducible control of the expression of a polypeptide of the invention.

It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. the polypeptide having lipolytic activity according to the invention, mutant forms the polypeptide, fragments, variants or functional equivalents thereof, fusion proteins, etc.).

The recombinant expression vectors of the invention can be designed for expression of the polypeptides according to the invention in prokaryotic or eukaryotic cells. For example, the polypeptides according to the invention can be produced in bacterial cells such as *E. coli* and *Bacilli*, insect cells (using baculovirus expression vectors), fungal cells, yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

In a preferred embodiment, a filamentous fungus or yeast is used as a host. For most filamentous fungi and yeast, the vector or expression construct is preferably integrated in the genome of the host cell in order to obtain stable transformants. However, for certain yeasts also suitable episomal vectors are available into which the expression construct can be incorporated for stable and high level expression, examples thereof include vectors derived from the 2μ and pKD1 plasmids of *Saccharomyces* and *Kluyveromyces*, respectively, or vectors containing an AMA sequence (e.g. AMA1 from *Aspergillus*). In case the expression constructs are integrated in the host cells genome, the constructs are either integrated at random loci in the genome, or at predetermined target loci using homologous recombination, in which case the target loci preferably comprise a highly expressed gene.

Accordingly, expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The nucleotide insert should be operatively linked to an appropriate promoter. Aside from the promoter native to the gene encoding the polypeptide of the invention, other promoters may be used to direct expression of the polypeptide of the invention. The promoter may be selected for its efficiency in directing the expression of the polypeptide of the invention in the desired expression host. Examples of promoters which may be useful in the invention include the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of the polypeptides according to the invention in a fungus or yeast. Such promoters are known in the art.

A variety of promoters can be used that are capable of directing transcription in the host cells of the invention. Preferably the promoter sequence is derived from a highly expressed gene. Examples of preferred highly expressed genes from which promoters are preferably derived and/or which are comprised in preferred predetermined target loci for integration of expression constructs, include but are not limited to genes encoding glycolytic enzymes such as triosephosphate isomerases (TPI), glyceraldehyde-phosphate dehydrogenases (GAPDH), phosphoglycerate kinases (PGK), pyruvate kinases (PYK or PKI), alcohol dehydrogenases (ADH), as well as genes encoding amylases, glucoamylases, proteases, xylanases, cellobiohydrolases, β-galactosidases, alcohol (methanol) oxidases, elongation factors and ribosomal proteins. Specific examples of suitable highly expressed genes include e.g. the LAC4 gene from *Kluyveromyces* sp., the methanol oxidase genes (AOX and MOX) from *Hansenula* and *Pichia*, respectively, the glucoamylase (glaA) genes from *A. niger* and *A. awamori*, the *A. oryzae* TAKA-amylase gene, the *A. nidulans* gpdA gene and the *T. reesei* cellobiohydrolase genes.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), a-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SPo2 promoters as well as promoters from extracellular protease genes.

Promoters suitable for plant cells include nopaline synthase (nos), octopine synthase (ocs), mannopine synthase (mas), ribulose small subunit (rubisco ssu), histone, rice actin, phaseolin, cauliflower mosaic virus (CMV) 35S and 19S and circovirus promoters.

All of the above-mentioned promoters are readily available in the art.

The vector may further include sequences flanking the polynucleotide giving rise to RNA which comprise sequences homologous to eukaryotic genomic sequences or viral genomic sequences. This will allow the introduction of the polynucleotides of the invention into the genome of a host cell.

The vector may contain a polynucleotide of the invention oriented in an antisense direction to provide for the production of antisense RNA.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989), Davis et al., Basic Methods in Molecular Biology (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include, but are not limited to, those which confer resistance to drugs or which complement a defect in the host cell. They include e.g. versatile marker genes that can be used for transformation of most filamentous fungi and yeasts such as acetamidase genes or cDNAs (the amdS, niaD, facA genes or cDNAs from *A. nidulans, A. oryzae* or *A. niger*), or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. URA3 (from *S. cerevisiae* or analogous genes from other yeasts), pyrG or pyrA (from *A. nidulans* or *A. niger*), argB (from *A. nidulans* or *A. niger*) or trpC. In a preferred embodiment the selection marker is deleted from the transformed host cell after introduction of the expression construct so as to obtain transformed host cells capable of producing the polypeptide which are free of selection marker genes.

Other markers include ATP synthetase, subunit 9 (oliC), orotidine-5'-phosphatedecarboxylase (pvrA), the bacterial G418 resistance gene (this may also be used in yeast, but not in fungi), the ampicillin resistance gene (*E. coli*), the neomycin resistance gene (*Bacillus*) and the *E. coli* uidA gene, coding for β-glucuronidase (GUS). Vectors may be used in vitro, for example for the production of RNA or used to transfect or transform a host cell.

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve four purposes: 1) to increase expression of recombinant protein; 2) to increase the solubility of the recombinant protein; 3) to aid in the purification of the recombinant protein by acting as a ligand in affinity purification; and 4) to protect the mature protein from proteolytic degradation. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukaryotic cell culture and tetracyline or ampicillin resistance for culturing in *E. coli* and other bacteria. Representative examples of appropriate host include bacterial cells, such as *E. coli, Streptomyces, Salmonella typhimurium*, and certain *Bacillus* species; fungal cells such as *Aspergillus* species, for example *A. niger, A. oryzae* and *A. nidulans*, and yeast such as *Kluyveromyces*, for example *K. lactis* and/or *Pichia*, for example *P. pastoris*; insect cells such as *Drosophila* S2 and *Spodoptera* Sf9; animal cells such as CHO, COS, *Bowes melanoma* and PER.C6 cells; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promotors suitable for use in the present invention include the promoters disclosed in WO-A1-2004/074468, which are hereby enclosed by reference.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at by 100 to 270, the cytomegalovirus early promoter enhancer, the polyoma enhancer on the late side of the replication origin, and adenovirus enhancers.

For effective initiation of translation, sequences could be added such as an optimal Kozak sequence in filamentous fungi or in yeast.

For secretion of the translated protein into the lumen of the endoplasmic reticulum, into the periplasmic space or into the extracellular environment, appropriate secretion signal may be incorporated into the expressed gene. The signals may be endogenous to the polypeptide or they may be heterologous signals. The inventors of the current invention have shown that the use of a lipase signal sequence leads to an improved (soluble) lipase amount (i.e. as present in the supernatant of a host cell which has been genetically modified for producing a lipase according to the invention.

The polypeptide according to the invention may be produced in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention *K. lactis*

The invention provides an isolated polypeptide having lipolitic activity comprising:

(a) an amino acid sequence which is at least 85% homologous to the amino acid sequence according to SEQ ID NO: 2;

(b) an amino acid sequence encoded by a polynucleotide, as defined in the section "Polynucleotides *K. lactis*,"

with the proviso that said polypeptide is not a wildtype lipase polypeptide, such as SEQ ID NO: 2. In other words a sequence showing 100% homology to SEQ ID NO:2 is preferably not within the scope of the invention. At least 1 amino acid should be different from SEQ ID NO: 2. Alternatively, the range of homology should be in the range of 85 to 99.7%, indicating that at least one amino acid must be different when compared to SEQ ID NO: 2.

A peptide or polypeptide being a functional equivalent and being at least 85% homologous to the mature polypeptide in the amino acid sequence according to SEQ ID NO: 2 is comprised within the present invention. A preferred example of a polypeptide according to the invention is a polypeptide having an amino acid sequence according to the polypeptide in the amino acid sequence according to SEQ ID NO: 5 or is a polypeptide having an amino acid sequence according to the polypeptide in the amino acid sequence according to SEQ ID NO: 7 or is a polypeptide having an amino acid sequence according to the polypeptide in the amino acid sequence according to SEQ ID NO: 9 or is a polypeptide having an amino acid sequence according to the polypeptide in the amino acid sequence according to SEQ ID NO: 11, with the proviso that said polypeptide is not a wildtype lipase polypeptide.

The above polypeptides are collectively comprised in the term "polypeptides according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" (or protein) is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual*, 2$^{nd}$, ed. *Cold Spring Harbor Laboratory*, Cold Spring Harbor Laboratory Press, Cold Spring Harbor, N.Y., 1989), By "isolated" polypeptide or protein is intended a polypeptide or protein removed from its native environment. For example, recombinantly produced polypeptides and proteins produced in host cells are considered isolated for the purpose of the invention as are native or recombinant polypeptides which have been substantially purified by any suitable technique such as, for example, the single-step purification method disclosed in Smith and Johnson, Gene 67:31-40 (1988).

As is known to the person skilled in the art it is possible that the N-termini of an amino acid sequence which is at least 85% homologous to the amino acid sequence according to SEQ ID NO: 2 might be heterogeneous as well as the C-terminus, due to processing errors during maturation. In particular such processing errors might occur upon overexpression of the polypeptide. In addition, exo-protease activity might give rise to heterogeneity. The extent to which heterogeneity occurs depends also on the host and fermentation protocols that are used. Such C-terminal processing artefacts might lead to shorter polypeptides or longer polypeptides as indicated herein. As a result of such errors the N-terminus might also be heterogeneous.

In a further embodiment, the invention provides an isolated polynucleotide encoding at least one functional domain of a polypeptide as described herein which contain additional residues and start at position −1, or −2, or −3 etc. Alternatively, it might lack certain residues and as a consequence start at position 2, or 3, or 4 etc. Also additional residues may be present at the C-terminus, e.g. at position 398, 399 etc. Alternatively, the C-terminus might lack certain residues and as a consequence end at position 396, or 395 etc.

The lipolytic enzyme according to the invention can be recovered and purified from recombinant cell cultures by methods known in the art (Protein Purification Protocols, Methods in Molecular Biology series by Paul Cutler, Humana Press, 2004).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Moreover, an amino acid sequence having at least 85% homology to the polypeptide of SEQ ID NO: 2 and comprising mutation:

SerxxxAsn which Ser in SEQ ID NO: 2 is located at position 184 (i.e. xxx=184; Ser184Asn with respect to SEQ ID NO: 2) or comprising mutation:

PheyyyLeu which Phe in SEQ ID NO: 2 is located at position 352 (i.e. yyy=352; Phe352Leu with respect to SEQ ID NO: 2) is explicitly excluded.

Furthermore, an amino acid sequence having at least 85% homology to the polypeptide in SEQ ID NO:2 and comprising only 2 mutations (when compared to SEQ ID NO: 2) at the amino acid sequence level which 2 amino acid sequence mutations are:

SerxxxAsn which Ser in SEQ ID NO: 2 is located at position 184 (i.e. xxx=184; Ser184Asn with respect to SEQ ID NO: 2) and:

PheyyyLeu which Phe in SEQ ID NO: 2 is located at position 352 (i.e. yyy=352; Phe352Leu with respect to SEQ ID NO: 2) is explicitly excluded.

Polypeptides According to the Invention *A. niger*

The invention further provides an isolated polypeptide having lipolitic activity comprising:

(a) an amino acid sequence which is at least 80% homologous to the amino acid sequence according to SEQ ID NO: 2;

(b) an amino acid sequence encoded by a polynucleotide as defined in the section "Polynucleotides *A. niger*,"

with the proviso that said polypeptide is not a wildtype lipase polypeptide, such as SEQ ID NO: 2. In other words a sequence showing 100% homology to SEQ ID NO:2 is preferably not within the scope of the invention. At least 1 amino acid should be different from SEQ ID NO: 2. Alternatively, the range of homology should be in the range of 80 to 99.7%, indicating that at least one amino acid must be different when compared to SEQ ID NO: 2.

The "section Polynucleotide *A. niger*" for example describes that the invention also provides an isolated polynucleotide which comprises a nucleotide sequence selected from:

(a) the nucleotide sequence as set out in SEQ ID NO: 15 or a functional equivalent thereof having at least 80% homology to the nucleotide sequence of SEQ ID NO: 15;

(b) a nucleotide sequence which hybridizes with a polynucleotide being the complement of SEQ ID NO: 15 and wherein said nucleotide sequence is at least 80% homologous to the nucleotide sequence of SEQ ID NO: 15;

(c) a nucleotide sequence encoding the polypeptide comprising the amino acid sequence according to SEQ ID NO: 2 or a functional equivalent thereof having at least 80% homology to the polypeptide in the amino acid sequence of SEQ ID NO: 2; or (d) a nucleotide sequence which is the complement of a nucleotide sequence as defined in (a), (b) or (c), with the proviso that the isolated polynucleotide is not a wildtype lipase polynucleotide.

A peptide or polypeptide being a functional equivalent and being at least 80% homologous to the mature polypeptide in the amino acid sequence according to SEQ ID NO: 2 is comprised within the present invention. A preferred example of a polypeptide according to the invention is a polypeptide having an amino acid sequence according to the polypeptide in the amino acid sequence according to SEQ ID NO: 7 or is a polypeptide having an amino acid sequence according to the polypeptide in the amino acid sequence according to SEQ ID NO: 18 or is a polypeptide having an amino acid sequence according to the polypeptide in the amino acid sequence according to SEQ ID NO: 20 or is a polypeptide having an amino acid sequence according to the polypeptide in the amino acid sequence according to SEQ ID NO: 22, with the proviso that said polypeptide is not a wildtype lipase polypeptide.

The above polypeptides are collectively comprised in the term "polypeptides according to the invention".

The terms "peptide" and "oligopeptide" are explained in the section "Polypeptides according to the invention *K. lactis*" and also apply to this section.

By "isolated" polypeptide or protein is intended a polypeptide or protein removed from its native environment. For example, recombinantly produced polypeptides and proteins produced in host cells are considered isolated for the purpose of the invention as are native or recombinant polypeptides which have been substantially purified by any suitable technique such as, for example, the single-step purification method disclosed in Smith and Johnson, Gene 67:31-40 (1988).

As is known to the person skilled in the art it is possible that the N-termini of an amino acid sequence which is at least 80% homologous to the amino acid sequence according to SEQ ID NO: 2 might be heterogeneous as well as the C-terminus, due to processing errors during maturation. In particular such processing errors might occur upon overexpression of the polypeptide. In addition, exo-protease activity might give rise to heterogeneity. The extent to which heterogeneity occurs depends also on the host and fermentation protocols that are used. Such C-terminal processing artefacts might lead to shorter polypeptides or longer polypeptides as indicated herein. As a result of such errors the N-terminus might also be heterogeneous.

In a further embodiment, the invention provides an isolated polynucleotide encoding at least one functional domain of a polypeptide as described herein which contain additional residues and start at position −1, or −2, or −3 etc. Alternatively, it might lack certain residues and as a consequence start at position 2, or 3, or 4 etc. Also additional residues may be present at the C-terminus, e.g. at position 398, 399 etc. Alternatively, the C-terminus might lack certain residues and as a consequence end at position 396, or 395 etc.

The lipolytic enzyme according to the invention can be recovered and purified from recombinant cell cultures by methods known in the art (Protein Purification Protocols, Methods in Molecular Biology series by Paul Cutler, Humana Press, 2004).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Moreover, an amino acid sequence having at least 80% homology to the polypeptide of SEQ ID NO: 2 and comprising mutation:

SerxxxAsn which Ser in SEQ ID NO: 2 is located at position 184 (i.e. xxx=184; Ser184Asn with respect to SEQ ID NO: 2) or comprising mutation:

PheyyyLeu which Phe in SEQ ID NO: 2 is located at position 352 (i.e. yyy=352; Phe352Leu with respect to SEQ ID NO: 2) is explicitly excluded.

Furthermore, an amino acid sequence having at least 80% homology to the polypeptide in SEQ ID NO:2 and comprising only 2 mutations (when compared to SEQ ID NO: 2) at the amino acid sequence level which 2 amino acid sequence mutations are:

SerxxxAsn which Ser in SEQ ID NO: 2 is located at position 184 (i.e. xxx=184; Ser184Asn with respect to SEQ ID NO: 2) and:

PheyyyLeu which Phe in SEQ ID NO: 2 is located at position 352 (i.e. yyy=352; Phe352Leu with respect to SEQ ID NO: 2) is explicitly excluded.

Polypeptide Fragments

The invention also features biologically active fragments of the polypeptides according to the invention.

Biologically active fragments of a polypeptide of the invention include polypeptides comprising amino acid sequences sufficiently identical to or derived from the amino acid sequence of the protein according to the invention (e.g., the mature polypeptide in the amino acid sequence of SEQ ID NO: 2, i.e. amino acids 20-397), which include fewer amino acids than the full length protein but which exhibit at least one biological activity of the corresponding full-length protein, preferably which exhibit lipolytic activity. Typically, biologically active fragments comprise a domain or motif with at least one activity of the protein according to the invention. A biologically active fragment of a protein of the invention can be a polypeptide which is, for example, 5, 10, 15, 20, 25, or more amino acids in length shorter than the mature polypeptide in SEQ ID NO: 2, and which has at least 85% homology to the mature polypeptide in SEQ ID NO: 2. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the protein according to the invention.

Fusion Proteins

The polypeptides according to the invention (for example SEQ ID NO: 5, 7, 9, 11, 18, 20 or 22) or functional equivalents thereof, e.g., biologically active portions thereof, can be operably linked to a polypeptide not according to the invention (e.g., heterologous amino acid sequences) to form fusion proteins. A "polypeptide not according to the invention" refers to a polypeptide having an amino acid sequence corresponding to a protein which is not substantially homologous to the protein according to the invention. Such "non-polypeptide not according to the invention" can be derived from the same or a different organism. Within a fusion protein the polypeptide according to the invention can correspond to all or a biologically active fragment of the lipolytic enzyme according to the invention. In a preferred embodiment, a fusion protein comprises at least two biologically active portions of the protein according to the invention. Within the fusion protein, the term "operably linked" is intended to indicate that the polypeptide according to the invention and the polypeptide not according to the invention are fused in-frame to each other. The polypeptide not according to the invention can be fused to the N-terminus or C-terminus of the polypeptide.

For example, in one embodiment, the fusion protein is a fusion protein in which the amino acid sequences are fused to the C-terminus of the GST sequences. Such fusion proteins can facilitate the purification of the recombinant protein according to the invention. In another embodiment, the fusion protein according to the invention is a protein containing a heterologous signal sequence at its N-terminus. In certain host cells (e.g., mammalian and yeast host cells), expression and/or secretion of the protein according to the invention can be increased through use of a hetereologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by known methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., Cell 37:767 (1984), for instance.

Preferably, a fusion protein according to the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g, a GST polypeptide). A nucleic acid encoding for a polypeptide according to the invention can be cloned into such an expression vector such that the fusion moiety is linked in-frame to the protein according to the invention.

Functional Equivalents

The terms "functional equivalents" and "functional variants" are used interchangeably herein.

Functional equivalents of the polynucleotide according to the invention are isolated polynucleotides having at least 60%, 65%, 70%, 75%, 80%, 81%, 82%, 83%, 84%, 85%, 86%, 87%, 88%, 89% preferably at least 90% homology to the nucleotide sequence of SEQ ID NO: 1 or to the nucleotide sequence of SEQ ID NO: 15 and that encodes a polypeptide that exhibits at least a particular function of the lipolytic enzyme according to the invention, preferably a polypeptide having lipolytic activity. A functional equivalent of a polypeptide according to the invention is a polypeptide having at least 60%, 65%, 70%, 75%, 80%, 85%, 86%, 87%, 88%, 89%, preferably at least 90%, 91%. 92%, 93%, 94%, 95%, 96%, 97%, 98% or 99% homology to the mature polypeptide in the amino acid sequence of SEQ ID NO: 2 and that exhibits at least one function of a lipolytic enzyme according to the invention, preferably which exhibits lipolytic activity. Functional equivalents as mentioned herewith also encompass biologically active fragments having lipolytic activity as described above.

Functional equivalents of the polypeptide according to the invention may contain substitutions of one or more amino acids of the mature polypeptide of the amino acid sequence according to SEQ ID NO: 2 or substitutions, insertions or deletions of amino acids which do not affect the particular functionality of the enzyme. Accordingly, a functionally neutral amino acid substitution is a substitution in the mature polypeptide of the amino acid sequence according to SEQ ID NO: 2 that does not substantially alters its particular functionality. For example, amino acid residues that are conserved among the proteins of the present invention are predicted to be particularly unamenable to alteration. Furthermore, amino acids conserved among the proteins according to the present invention and other lipolytic enzymes are not likely to be amenable to alteration.

Functional equivalents of the polynucleotides according to the invention may typically contain silent mutations or mutations that do not alter the biological function of the encoded polypeptide. Accordingly, the invention provides nucleic acid molecules encoding polypeptides according to the invention that contain changes in amino acid residues that are not essential for a particular biological activity. However, one can also introduce mutations that do affect a certain characteristic of the polypeptide, such as the polypeptide's ability to bind to the exterior of the host cell producing said polypeptide. It is herein disclosed that mutations affecting glycosylation and/or overall hydrophobicity and/or productivity and/or availability in the supernatant of the polypeptide with SEQ ID NO: 2, have an impact of their binding characteristics. Such proteins differ in amino acid sequence from the mature polypeptide in the amino acid sequence according to SEQ ID NO: 2 but yet retain at least one biological activity thereof, preferably they retain the lipolytic activity. In one embodiment a functional equivalent of the polynucleotide according to the invention comprises a nucleotide sequence encoding a polypeptide according to the invention, wherein the polypeptide comprises a substantially homologous amino acid sequence of at least about 60%, 65%, 70%, 75%, 80%, 85%, preferably at least 90%, 91%, 92%, 93%, 94%, 95%, 96%, 97%, 98%, 99% or more homologous to the mature polypeptide in the amino acid sequence according to SEQ ID NO: 2. In one embodiment the functional equivalent of the mature polypeptide in the amino acid sequence according to SEQ ID NO: 2 having at least 85% homology thereto is the polypeptide having an amino acid sequence according to the mature polypeptide in the amino acid sequence according to SEQ ID NO: 5, in another embodiment it is the polypeptide having an amino acid sequence according to the mature polypeptide in the amino acid sequence according to SEQ ID NO: 7, and in yet another embodiment it is the polypeptide having an amino acid sequence according to the mature polypeptide in the amino acid sequence according to SEQ ID NO: 9 and in another embodiment it is the polypeptide having an amino acid sequence according to the mature polypeptide in the amino acid sequence according to SEQ ID NO: 11. Thus the invention also provides an isolated polynucleotide as described herein, wherein the functional equivalent as recited in part (c) comprises a sequence selected from SEQ ID NO: 5, 7, 9 or 11.

In another embodiment the functional equivalent of the mature polypeptide in the amino acid sequence according to SEQ ID NO: 2 having at least 80% homology thereto is the polypeptide having an amino acid sequence according to the mature polypeptide in the amino acid sequence according to SEQ ID NO: 7, in another embodiment it is the polypeptide having an amino acid sequence according to the mature polypeptide in the amino acid sequence according to SEQ ID NO: 18, and in yet another embodiment it is the polypeptide having an amino acid sequence according to the mature polypeptide in the amino acid sequence according to SEQ ID NO: 20 and in another embodiment it is the polypeptide having an amino acid sequence according to the mature polypeptide in the amino acid sequence according to SEQ ID NO: 22. Thus the invention also provides an isolated polynucleotide as described herein, wherein the functional equivalent as recited in part (c) comprises a sequence selected from SEQ ID NO: 7, 18, 20 or 22.

A functional equivalent of the polynucleotide according to the invention encoding a polypeptide according to the invention will comprise a polynucleotide sequence which is at least about 60%, 65%, 70%, 75%, 80%, 85%, preferably at least 90%, 91%, 92%, 93%, 94%, 95%, 96%, 97%, 98%, 99%, or more homologous to a nucleic acid sequence according to SEQ ID NO 1 or to a nucleic acid sequence according to SEQ ID NO 15.

In one embodiment a functional equivalent of the polynucleotide according to SEQ ID NO: 1 having at least 80% homology thereto is the polynucleotide having a nucleotide sequence according to SEQ ID NO: 4, in another embodiment it is the polynucleotide having a nucleotide sequence according to SEQ ID NO: 6, in yet another embodiment it is the polynucleotide having a nucleotide sequence according to SEQ ID NO: 8 and in yet another embodiment it is the polynucleotide having a nucleotide sequence according to SEQ ID NO: 10. The polynucleotide sequence according to SEQ ID NO: 4 encodes the polypeptide according to SEQ ID NO: 5, the polynucleotide sequence according to SEQ ID NO: 6 encodes the polypeptide according to SEQ ID NO: 7, the polynucleotide sequence according to SEQ ID NO: 8 encodes the polypeptide according to SEQ ID NO: 9 and the polynucleotide sequence according to SEQ ID NO: 10 encodes the polypeptide according to SEQ ID NO: 11. Therefore, the invention provides an isolated polynucleotide as described herein, wherein the functional equivalent as recited in part (a) (which refers to SEQ ID NO: 1) comprises a sequence selected from SEQ ID NO: 4, 6, 8, 10 or 15.

In another embodiment a functional equivalent of the polynucleotide according to SEQ ID NO: 15 having at least 80% homology thereto is the polynucleotide having a nucleotide sequence according to SEQ ID NO: 16, in another embodiment it is the polynucleotide having a nucleotide sequence according to SEQ ID NO: 17, in yet another embodiment it is the polynucleotide having a nucleotide sequence according to SEQ ID NO: 19 and in yet another embodiment it is the polynucleotide having a nucleotide sequence according to SEQ ID NO: 21. The polynucleotide sequence according to SEQ ID NO: 16 encodes the polypeptide according to SEQ ID NO: 7, the polynucleotide sequence according to SEQ ID NO: 17 encodes the polypeptide according to SEQ ID NO: 18, the polynucleotide sequence according to SEQ ID NO: 19 encodes the polypeptide according to SEQ ID NO: 20 and the polynucleotide sequence according to SEQ ID NO: 21 encodes the polypeptide according to SEQ ID NO: 22. Therefore, the invention provides an isolated polynucleotide as described herein, wherein the functional equivalent as recited in part (a) (which refers to SEQ ID NO: 15) comprises a sequence selected from SEQ ID NO: 16, 17, 19 or 21.

An isolated polynucleotide encoding a protein homologous to the mature polypeptide in the amino acid sequence according to SEQ ID NO: 2 can be created by introducing one or more nucleotide substitutions, additions or deletions into the coding nucleotide sequences according to SEQ ID NO: 1 or according to SEQ ID NO: 15 such that one or more amino acid substitutions, deletions or insertions are introduced into the encoded protein. Such mutations may be introduced by standard techniques, such as site-directed mutagenesis and PCR-mediated mutagenesis.

Nucleic acids encoding other family members having lipolytic activity, which thus have a nucleotide sequence that differs from SEQ ID NO: 1, 4, 6, 8, 10, 15, 16, 17, 19 or 21 which fulfils to the conditions mentioned above are within the scope of the invention. Moreover, nucleic acids encoding proteins having lipolytic activity, which have an amino acid sequence which differs from the mature polypeptide in the amino acid sequence SEQ ID NO: 2, 5, 7, 9, 11, 18, 20 or 22 and which fulfil the conditions mention above are within the scope of the invention.

Nucleic acid molecules corresponding to variants (e.g. natural allelic variants) and homologues of the polynucleotides according to the invention can be isolated based on their homology to the nucleic acids disclosed herein using the cDNAs disclosed herein or a suitable fragment thereof, as a hybridisation probe according to standard hybridisation techniques preferably under highly stringent hybridisation conditions.

In another aspect of the invention, improved proteins are provided. Improved proteins are proteins wherein at least one biological activity is improved if compared with the biological activity of the polypeptide having amino acid sequence according to SEQ ID NO: 2. Such proteins may be obtained by randomly introducing mutations along all or part of the coding sequence SEQ ID NO: 1 or 15, such as by saturation mutagenesis, and the resulting mutants can be expressed recombinantly and screened for biological activity. For instance, the art provides for standard assays for measuring the enzymatic activity of lipolytic enzymes and thus improved proteins may easily be selected. Examples of such improved proteins are proteins which have improved solubility features, i.e. proteins which after secretion are available in the supernatant in stead of being bound to the used host cell.

In a further preferred embodiment, the protein according to the invention has an amino acid sequence encoded by an isolated nucleic acid fragment which hybridizes with a polynucleotide being the complement of SEQ ID NO: 1 or 15 and wherein said nucleotide sequence is at least 70% to 80% homologous to the nucleotide sequence of SEQ ID NO: 1 or 15, preferably under highly stringent hybridisation conditions.

Accordingly, the protein according to the invention is preferably a protein which comprises an amino acid sequence at least about 85%, 86%, 87%, 88%, 89%, 90%, 91% 92% 93% 94%, 95%, 96%, 97%, 98%, 99% or more homologous to the mature polypeptide in the amino acid sequence according to SEQ ID NO 2 and retains at least one functional activity of the mature polypeptide in the amino acid sequence according to SEQ ID NO: 2.

Functional equivalents of a protein according to the invention can also be identified e.g. by screening combinatorial libraries of mutants, e.g. truncation mutants, of the protein of the invention for lipolytic enzyme activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having a lipolytic activity according to the invention include, inter alia, (1) isolating the gene encoding the protein, or allelic variants thereof from a cDNA library; (2) in situ hybridization (e.g. FISH) to metaphase chromosomal spreads to provide precise chromosomal location of the gene as described in Verma et al., Human Chromosomes: a Manual of Basic Techniques, Pergamon Press, New York (1988); (3) Northern blot analysis for detecting expression of mRNA in specific tissues and/or cells and 4) probes and primers that can be used as a diagnostic tool to analyse the presence of a nucleic acid hybridisable to the probe in a given biological (e.g. tissue) sample.

Also encompassed by the invention is a method of obtaining a functional equivalent of a gene according to the invention. Such a method entails obtaining a labelled probe that includes an isolated nucleic acid which encodes all or a portion of the protein sequence according to the mature polypeptide in the amino acid sequence according to SEQ ID NO: 2 or a variant of any of them; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the gene according to the invention.

Host Cells

In another embodiment, the invention features cells, e.g., transformed host cells or recombinant host cells comprising a polynucleotide according to the invention or comprising a vector according to the invention. Preferably, said recombinant host cell is capable of expressing or over-expressing said polynucleotide or vector.

A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like. Host cells also include, but are not limited to, mammalian cell lines such as CHO, VERO, BHK, HeLa, COS, MDCK, 293, 3T3, WI38, and choroid plexus cell lines. A number of vectors suitable for stable transfection of mammalian cells are available to the public, methods for constructing such cell lines are also publicly known, e.g., in Ausubel et al. (supra). Especially preferred are cells from filamentous fungi, in particular *Aspergillus* species such as *Aspergillus niger* or *oryzae* or *awamori*. Also especially preferred are yeast cells, in particular *Kluyveromyces* such as *K. lactis*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein produced. To this end, eukaryotic host cells that possess the cellular machinery for proper processing of the primary transcript, glycosylation, and phosphorylation of the gene product can be used. Such host cells are well known in the art.

If desired, a cell as described above may be used to in the preparation of a polypeptide according to the invention. Such a method typically comprises cultivating a recombinant host cell (e.g. transformed or transfected with an expression vector as described above) under conditions to provide for expression (by the vector) of a coding sequence encoding the polypeptide, and optionally recovering, more preferably recovering and purifying the produced polypeptide from the cell or culture medium. Polynucleotides of the invention can be incorporated into a recombinant replicable vector, e.g. an expression vector. The vector may be used to replicate the nucleic acid in a compatible host cell. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably the polypeptide is produced as a secreted protein in which case the nucleotide sequence encoding a mature form of the polypeptide in the expression construct is operably linked to a nucleotide sequence encoding a signal sequence. Preferably the signal sequence is native (homologous) to the nucleotide sequence encoding the polypeptide. Alternatively the signal sequence is foreign (heterologous) to the nucleotide sequence encoding the polypeptide, in which case the signal sequence is preferably endogenous to the host cell in which the nucleotide sequence according to the invention is expressed. Examples of suitable signal sequences for yeast host cells are the signal sequences derived from yeast a-factor genes. Similarly, a suitable signal sequence for filamentous fungal host cells is e.g. a signal sequence derived from a filamentous fungal amyloglucosidase (AG) gene, e.g. the *A. niger* glaA gene or alternatively a part of the AG protein (such as 498 amino acids) can be used as a carrier. This may be used in combination with the amyloglucosidase (also called (gluco) amylase) promoter itself, as well as in combination with other promoters. Hybrid signal sequences may also be used with the context of the present invention. Yet another preferred signal sequence is a lipase signal sequence, for example SEQ ID NO: 14.

Preferred heterologous secretion leader sequences are those originating from the fungal amyloglucosidase (AG) gene (glaA-both 18 and 24 amino acid versions e.g. from *Aspergillus*), the α-factor gene (yeasts e.g. *Saccharomyces* and *Kluyveromyces*) or the α-amylase gene (*Bacillus*).

The vectors may be transformed or transfected into a suitable host cell as described above to provide for expression of a polypeptide of the invention. This process may comprise culturing a host cell transformed with an expression vector as described above under conditions to provide for expression by the vector of a coding sequence encoding the polypeptide.

The invention thus provides host cells transformed or transfected with or comprising a polynucleotide or vector of the invention. Preferably the polynucleotide is carried in a vector for the replication and expression of the polynucleotide. The cells will be chosen to be compatible with the said vector and may for example be prokaryotic (for example bacterial), fungal, yeast or plant cells.

A heterologous host may also be chosen wherein the polypeptide of the invention is produced in a form which is substantially free of enzymatic activities that might interfere with the applications, e.g. free from starch degrading, cellulose-degrading or hemicellulose degrading enzymes. This may be achieved by choosing a host which does not normally produce such enzymes.

The invention encompasses processes for the production of the polypeptide of the invention by means of recombinant expression of a DNA sequence encoding the polypeptide. For this purpose the DNA sequence of the invention can be used for gene amplification and/or exchange of expression signals, such as promoters, secretion signal sequences, in order to allow economic production of the polypeptide in a suitable homologous or heterologous host cell. A homologous host cell is a host cell which is of the same species or which is a variant within the same species as the species from which the DNA sequence is derived.

Suitable host cells are preferably prokaryotic microorganisms such as bacteria, or more preferably eukaryotic organisms, for example fungi, such as yeasts or filamentous fungi, or plant cells. In general, yeast cells are preferred over fungal cells because they are easier to manipulate. However, some proteins are either poorly secreted from yeasts, or in some cases are not processed properly (e.g. hyperglycosylation in yeast). In these instances, a fungal host organism should be selected.

The host cell may over-express the polypeptide, and techniques for engineering over-expression are well known. The host may thus have two or more copies of the encoding polynucleotide (and the vector may thus have two or more copies accordingly).

Therefore in one embodiment of the invention the recombinant host cell according to the invention is capable of expressing or overexpressing a polynucleotide or vector according to the invention.

According to the present invention, the production of the polypeptide of the invention can be effected by the culturing of a host cell according to the invention, which have been transformed with one or more polynucleotides of the present invention, in a conventional nutrient fermentation medium.

The recombinant host cells according to the invention may be cultured using procedures known in the art. For each combination of a promoter and a host cell, culture conditions are available which are conducive to the expression the DNA sequence encoding the polypeptide. After reaching the desired cell density or titer of the polypeptide the culture is stopped and the polypeptide is recovered using known procedures.

The fermentation medium can comprise a known culture medium containing a carbon source (e.g. glucose, maltose, molasses, etc.), a nitrogen source (e.g. ammonium sulphate, ammonium nitrate, ammonium chloride, etc.), an organic nitrogen source (e.g. yeast extract, malt extract, peptone, etc.) and inorganic nutrient sources (e.g. phosphate, magnesium, potassium, zinc, iron, etc.).

The selection of the appropriate medium may be based on the choice of expression host and/or based on the regulatory requirements of the expression construct. Such media are known to those skilled in the art. The medium may, if desired, contain additional components favouring the transformed expression hosts over other potentially contaminating microorganisms.

The fermentation can be performed over a period of 0.5-30 days. It may be a batch, continuous or fed-batch process, suitably at a temperature in the range of, for example, from about 0 to 45° C. and/or at a pH, for example, from about 2 to about 10. Preferred fermentation conditions are a temperature in the range of from about 20 to about 37° C. and/or at a pH of from about 3 to about 9. The appropriate conditions are usually selected based on the choice of the expression host and the protein to be produced.

After fermentation, if necessary, the cells can be removed from the fermentation broth by means of centrifugation or filtration. After fermentation has stopped or after removal of the cells, the polypeptide of the invention may then be recovered and, if desired, purified and isolated by conventional means.

An Example of a Host Cell Expressing a Polypeptide as Described Herein

Upon overexpressing CPO PGE in yeast, a large amount of produced protein sticks to the exterior (i.e. to the membrane surrounding the cell) of the yeast cells. The same is true, although to a lesser extent, for some of the herein described mutants. The inventors of the present invention have surprisingly noted that cells with immobilised lipase at its exterior can be used in all kinds of applications (to be discussed in more detail later on). Before applying immobilised lipase the host cells are preferably inactivated/killed.

The invention therefore provides a recombinant host cell comprising a polynucleotide or comprising a vector as described herein, preferably said cell is capable of expressing or over-expressing said polynucleotide or vector to produce the desired polypeptide, which host cell after expression of the polypeptide encoded by said polynucleotide, is inactivated. Even more preferably, said inactivated/killed cell has at least part of the polypeptide encoded by said polynucleotide attached to its surrounding cell membrane or cell wall.

The person skilled in the art is well capable of inactivating/killing a host cell, for example by using classical approaches with benzoates or parabens.

As an alternative, the inventors have developed another killing route by using incubation at alkaline pH values. This method will be explained in more detail later on.

After inactivating/killing the used host cell, the cells can be separated by using any suitable technique (for example centrifugation) and subsequently the cells can be dried and used in a powder formulation. Preferably the used micro-organism is yeast, such as, but not limited to, *Kluveromyces* (for example *K. lactis*). Even more preferably, the used micro-organism is capable of expressing (or expresses) a polypeptide as described herein. Surprisingly such cells show a free fatty acids profile suitable for use in for example dairy applications.

In one of its aspects, the inactivated/killed micro-organism is a recombinant micro-organism and preferably said micro-organism produced (or is capable of producing) a polypeptide of interest such as a lipolytic enzyme.

In yet another aspect the inactivated/killed micro-organism as described above is used in food manufacturing, for example in the preparation of a diary product.

In a further aspect, the invention provides a method for preparing a dairy product wherein an inactivated micro-organism as described above is added to a dairy composition used in the production of a dairy product under conditions sufficient for the enzyme to react.

Release of a Polypeptide as Described Herein from the Host Cell

As described in the previous section, the use of inactivated/killed host cells with a polypeptide as described herein attached to their membrane is suitable for use in the manufacture of for example food compositions.

Alternatively, one can decide to obtain the produced polypeptide free from the membrane. It is shown herein that the polypeptide according to the invention can be freed (at least in part) from the host cell by incubating the host cells (which host cells are optionally inactivated/killed) with the bound polypeptide at alkaline pH, preferably pH 10-11.

The invention therefore provides a method for at least in part releasing a polypeptide bound to the exterior of a micro-organism comprising contacting said micro-organism with an aqueous solution having a pH of approximately 9-12 and allowing the obtained solution to incubate for at least 2 hours at a temperature of between 4 and 30 degrees Celsius. In a more preferred embodiment, the used pH is approximately 9.5-11.5 or approximately 10-11. Most preferred is a pH of around 11 (i.e. between pH 10.5-11.5) and even more preferably the incubation time is between 2 hours and 4-5 days. The temperature can for example be selected based on the time of incubation and can vary between 4 and 30 degrees Celsius. Upon increased incubation time, the temperature is preferably decreased to lower temperatures such as for example 4 to 20, 4 to 15 or 4 to 10 or 4 to 8 degrees Celsius.

The selection of the variables time, temperature and pH can easily be made by the skilled person and depend for example on the desired concentration of enzyme/yield or on the concentration of used biomass.

The desired pH can be obtained by adding a concentrated acidic or alkaline solution to the fermentation liquid as such. It is also possible to first remove as much fermentation liquid as possible and the resuspending the cells in a suitable solution with the desired pH.

In one of its aspect such a method further comprises maintaining the pH at an approximately constant level (for example deviation between plus or minus 0.5 pH units) by monitoring the pH at regular intervals (or continuously) and optionally by adding an acidic or alkaline solution.

In one of its aspects such a method further comprises the use of a surfactant to further improve the release from the polypeptide of the cellular biomass.

In one of its aspects, the optionally inactivated/killed micro-organism is a recombinant micro-organism and preferably said micro-organism produced (or is capable of producing) a polypeptide of interest such as a lipolytic enzyme. Preferably the used micro-organism is yeast, such as, but not limited to, *Kluveromyces* (for example *K. lactis*). Even more preferably, said lipolytic enzyme is any of the herein described polypeptides.

Preferably, said method uses inactivated/killed biomass as starting material. Moreover, the method could include a step of inactivating or killing the biomass.

A Method for Killing a Host Cell

The invention further provides an alternative method for killing/inactivating host cells. Typically host cells are killed by using killing agents such as benzoates and/or parabens. Surprisingly, it is now disclosed that killing of host cells can be obtained without using such a classical killing agent. Cells can equally well be killed by increasing the pH to alkaline values.

The invention therefore provides a method for killing a micro-organism comprising contacting said micro-organism with an aqueous solution having a pH of from 9 to 11 and allowing the obtained solution to incubate for at least 2 hours at a temperature of between 10 and 20 degrees Celsius. In one of its aspects said micro-organism is a recombinant micro-organism (for example *Kluveromyces*) and in yet another aspect said micro-organism produces a polypeptide of interest, preferably a lipolytic enzyme, even more preferably a lipolytic polypeptide according to the invention.

The invention further provides use of an alkaline pH, such as pH 9-11, for killing (host) cells.

Typically, the cells to be killed are first grown at temperatures such as 30 degrees Celsius. After a desired cell density is obtained and/or after the cells have been provided with enough time to produce a protein according to the invention, the temperature is typically lowered from around 30 degrees Celsius (i.e. fermentation temperature) to about 10 to 20 degrees Celsius (more preferably to about 13 to 17 degrees Celsius). After lowering the temperature, the pH is adjusted to around 9 to 11 (more preferably around pH 10). Optionally, the cells can first be transferred (for example pumped) to a storage vessel before lowering the temperature and increasing the pH.

The incubation time can vary between 4 to 5 days and preferably between 2-4 days. The time needed for killing off depends for example on the biomass concentration.

A Method for Killing a Host Cell and Releasing a Polypeptide Bound to Said Host Cell The above described methods for at least in part releasing a polypeptide bound to a cell and for killing a cell can be conveniently combined into one method.

The invention therefore provides a method for killing a micro-organism and for at least in part releasing a polypeptide bound to the exterior of a micro-organism comprising contacting said micro-organism with an aqueous solution having a pH of approximately 9 to 11 (preferably about 10) and allowing the obtained solution to incubate for at least 2 hours at a temperature of between 10 and 20 degrees Celsius (preferably around 15 degrees Celsius), further comprising contacting said micro-organism with an aqueous solution having a pH of approximately 9 to 12, preferably 9 to 11 (and even more preferably between 10.5-11.5) and allowing the obtained solution to incubate for at least 2 hours at a temperature of between 4 and 30 degrees Celsius (preferably between 4 to 8 degrees Celsius). Optionally, a stabiliser can be added during any of these steps. For the skilled person stabilizers are well known additives. To improve the stability of the produced protein the pH is preferably maintained at a constant level (for example around 10).

In one of its aspects said micro-organism is a recombinant micro-organism and in yet another aspect said micro-organism produces a polypeptide of interest, preferably a lipolytic enzyme. In a preferred embodiment, said lipolytic enzyme is a polypeptide according to the invention. In yet another preferred embodiment the used host cell is *Kluveromyces* such as *K. lactis*.

The invention thus for example provides a method for producing a lipase and releasing said lipase from biomass comprising:
  fermenting a host cell using suitable conditions (pH, temperature etc.)
  cooling the obtained biomass to approximately 15 degrees Celsius
  killing the host cells by incubating said cells at a pH of approximately 9-11, preferably 10-11
  optionally desorption of the lipase bound to the biomass by incubating during 2-5 days at a pH of approximately 9 to 12, 9 to 11 and preferably between 10-11 at 4-8 degrees Celsius
  optionally biomass separation (for example by centrifugation)
  optionally germ reduction filtration
  optionally concentration by ultrafiltration
  optionally freeze drying
  optionally another germ reduction filtration
  optionally formulation of the enzyme, for example by adding formulation agents like glycerol
  optionally adding adsorbent to the fermentation Production Scale In a preferred embodiment the methods for killing a micro-organism and the methods for releasing a polypeptide from cells capable of expressing said polypeptide as described herein are performed on biomass material obtained from large(r) scale productions. For examples productions on Eschweiler scale such as 10 to 15 liter fermentations or productions on even larger scale such as using 100, 140, 200 or 280 $m^3$ fermentors. In a preferred embodiment the host cells are subjected to large scale fermentation before being subjected to a killing method as described herein or before being subjected to a method for releasing the produced enzymatic activity.

Cells as Adsorbent for Lipases

As described herein, part of the lipases of the invention bind to the outer structure of the used host cells. As a consequence, cells like yeast cells (for example *Kluveromyces* cells such as *K. lactis* cells) can be used to immobilise lipase, for example lipases from other sources, such as lipases derived from goat, kid goat, calf or lamb.

The invention thus provides the use of a *Kluveromyces* cell as adsorbens for a lipolytic enzyme.

Use of the Lipolytic Enzyme in Industrial Processes

The invention also relates to the use of the lipolytic enzyme according to the invention in a number of industrial processes. Despite the long-term experience obtained with these processes, the lipolytic enzyme according to the invention features a number of significant advantages over the enzymes currently used. Depending on the specific application, these advantages can include aspects like lower production costs, reproducibility of fermentation and thus the end product, higher specificity towards the substrate, less antigenic, less undesirable side activities, higher yields when produced in a suitable micro-organism, more suitable pH and temperature ranges, better tastes of the final product as well as food grade, Hallal and kosher aspects Preferably the isolated polypeptide according to the invention having lipolytic activity can be used in the food industry, more preferably in food manufacturing.

In one of its aspects the invention provides use of an isolated polypeptide as described herein or obtainable according to any of the methods of the invention in food manufacturing. The invention further provides use of an inactivated micro-organism as described above in food manufacturing. Preferably, said use is in the manufacture of a dairy product, preferably in the manufacture of cheese, cheese-like product, enzyme modified cheese (EMC) or in the manufacture of free fatty acid mixtures obtainable by the lypolisis of butter fat or cream.

Also provided is a diary product obtainable by the use of any one the described uses or methods.

Dairy Applications

In one preferred embodiment the polypeptide according to the invention can be used in the dairy industry such as a method for preparing a dairy product wherein an isolated polypeptide of the invention or obtainable according to a method of the invention, is added to a dairy composition used in the production of a dairy product under conditions sufficient for the enzyme to react. Also provided is a method for preparing a dairy product wherein an inactivated micro-organism of the invention is added to a dairy composition used in the production of a dairy product under conditions sufficient for the enzyme to react.

In one embodiment the polypeptide according to the invention is used in the manufacture of a dairy product, preferably a cheese, cheese-like product, EMC, or of milk fat-derived free fatty acid mixtures, preferably to develop and/or intensify the flavour of the dairy product.

In the context of the present invention a 'dairy product' refers to any kind of milk-based product, including but not limited to cheese, butter, EMC, cream, dairy analog etcetera. Of particular interest in the present context are milk fat-containing products and their equivalents, including regular cheeses, cheese analogues, processed cheeses, butter, spreads, margarines, EMC, etc.

In a preferred embodiment, the dairy product is a cheese. The cheese may be of any variety, e.g. hard cheeses such as Chester, Danbo, Manchego, Saint Paulin, Cheddar, Monterey, Colby, Edam, Gouda, Muenster, Swiss type, Gruyere, Emmenthaler, Parmesan, Pecorino, Provolone, and Romano; curd-cheese such as Feta, pasta filata cheeses such as Mozzarella; processed cheese; white mould cheese such as Brie and Camembert; or blue mould cheeses such as Gorgonzola and Danish blue cheese, or fresh cheese such as e.g. Ricotta, Cream cheese, Neufchatel or Cottage cheese. Preferred types of cheese in this context are Parmesan, Pecorino, Provolone, Romano or Feta.

The term 'dairy analogues' refers to dairy-like products which contain fat (such as e.g. milk fat, e.g. cream) as part of the composition, and which further contain, as part of the composition, a non-milk constituent, such as e.g. vegetable oil.

The present invention also relates to a method for preparing a dairy product wherein an isolated polypeptide according to the invention is added to a dairy composition used in the production of a dairy product.

In the context of the present invention, a dairy composition may be a composition comprising milk and/or one or more milk components and/or milk fractions which is the starting composition in the production of the dairy product according to the invention or it may be an intermediate product in the production of the dairy product (e.g. curd or whey). The dairy composition is a suitable substrate for the lipolytic enzyme and therefore the dairy composition will comprise at least milk fat and/or other fat, e.g. vegetable-derived fat. Lipolytic enzymes according to the invention are able to catalyse the hydrolysis of ester bonds in glycerides present in the dairy composition and they have therefore lipase activity. Glycerides are esters of glycerol and fatty acids. Triglycerides (also known as triacylglycerol or triacylglycerides) are mostly present in vegetable oils and animal fat. Lipases (EC 3.1.1.3) are defined herein as enzymes that hydrolyse one or more of the fatty acids from lipids; more specifically they hydrolyse the ester bond between fatty acid and hydroxyl groups of the glycerol.

A milk component may be any constituent of milk such as milk fat, milk protein, casein, whey protein, lactose. A milk fraction may be any fraction of milk such as e.g. skimmed milk, butter milk, whey, cream, butter, milk treated by ultrafiltration, milk powder, whole milk powder, butter milk powder, or skimmed milk powder. In the present context milk may be the lacteal secretion of any mammal. Thus, milk may be obtained by milking, e.g., cow, sheep, goat, buffalo, or camel.

The dairy product produced with the method of this aspect of the invention may be produced with any suitable process known in the art and the lipolytic enzyme will be added to the dairy composition at any suitable step during the production of the dairy product under suitable conditions of e.g. enzyme concentration, temperature and time sufficient for the enzyme to exhibit its lipolytic activity.

In one embodiment, the method according to the invention is a method for the production of cheese. In this case the method will comprise a step in which curd is formed by enzymatic coagulation of a dairy composition with rennet, or by acidic coagulation with food grade acid or acid produced by lactic acid bacteria growth and it is subsequently separated from the whey. Depending on the type of cheese to be produced, the production of cheese may further comprise processing of the curd and aging of the resulting cheese. The method to produce cheese according to this aspect of the invention will preferably include aging of the resulting cheese. The lipolytic enzyme can be added to a dairy composition in various stages of cheese preparation. Preferably, the enzyme is added to the milk prior to or together with the addition of a coagulant (e.g. chymosin). Addition at this point ensures a homogenous distribution of the enzyme throughout the cheese. Alternatively, the enzyme can be added in a later stage, e.g. to the curd, but this introduces the risk of inhomogeneous enzyme distribution in the cheese. For that reason, addition of the enzymes to the milk is preferred.

In another embodiment the method to produce a dairy product according to the present invention is the manufacture of milk fat-derived free fatty acid mixtures which is obtained by lypolisis of milk fat (e.g. butter fat or cream) to yield a free fatty acid mixture which can be for example used flavouring, e.g. in blue cheese flavour. These free fatty acid mixtures can be used as flavour ingredients in the production of other products, e.g. spreads, soups, dressings, snacks, chips, nachos, etcetera). Other lipase applications include the use in modified milk powder (Kilara in Encyclopedia of Dairy Sciences, (2003; Fox et all eds, Academic Press) pp. 914-918).

In yet another embodiment the method to produce a dairy product according to the present invention is a method to produce EMC. In this case the method can typically be performed using conditions known to those skilled in the art (see e.g. Ch. 2.12 in Industrial Enzymology, $2^{nd}$ Ed., Godfrey, West, Eds, MacMillan Press, London, 1996; Wilkinson et al in Encyclopedia of Dairy Sciences, (2003; Fox et all eds, Academic Press) pp. 434-438).

The amount of enzyme to be added in any one of the above-mentioned processes will depend on the enzyme activity and on the desired flavour effect in the final product. The amount to be used in an application can be determined by those skilled in the art by using a dose response curve. In this approach increasing amounts of enzyme are added to the dairy composition and subsequently the intensity of the flavour profile is analysed in the final product by a trained taste panel.

In a preferred embodiment of the use according to the invention or of the method to produce a dairy product according to the invention, the lipolytic enzyme according to the invention is used for development and/or intensification of flavour. Flavour development in the production of a dairy product is due, among others, to the action of enzymes, be it produced by microorganisms used during the production of the dairy product or specifically added during the manufacture, more specifically to the action of lipolytic and proteolytic enzymes.

Lipolytic enzymes are responsible for the lipolysis of milk fat present in the dairy product and the consequent release in the product of free fatty acid mixtures (hereafter indicated as FFA). The composition of the free fatty acid mixture is partially responsible for the final flavour of the dairy product. Starting from a substrate containing milk fat, a lipolytic enzyme will produce a specific FFA mixture of C4- to C18- free fatty acids wherein the relative amount of each component in the mixture will depend on the specificity of the enzyme towards the hydrolysis of specific triglyceride ester bonds involving the C4- to C18-fatty acids present in the triglyceride. For example a lipolytic enzyme which has high specificity for C4-fatty acids will preferentially hydrolyse triglyceride ester bonds of the triglyceril moiety with a C4-fatty acid rather than with C6- to C18-fatty acids and the relative content of C4-free fatty acid in the mixture will be higher if compared with the relative content of C6- to C18- free fatty acids. Furthermore the relative amount of each component in the mixture will also depend on the starting substrate and on the composition of the triglycerides present therein. Because every fatty acid is responsible for imparting to a product specific flavour characteristics, when a specific milk fat containing substrate is subjected to the action of a lipolytic enzyme under conditions of enzyme concentration, temperature and time sufficient for the enzyme to react, a specific FFA mixture is produced which gives rise to a specific flavour profile in the substrate. The specificity of several lipolytic enzymes towards the release of free fatty acids and therefore also the generated flavour profile can be compared with each other by determination of a FFA profile for each of the enzymes using the same substrate. A FFA profile gives the relative amount of each of C4- to C18-free fatty acids in respect of the total amount of free fatty acid released by the action of the lipolytic enzyme on the substrate. The FFA profile will generally depend from the starting substrate, on the specificity of the lipolytic enzyme towards the fatty acid substituents in the lipid composition.

The degree of fat conversion (D) is calculated as follows (expressed in %):

D=[(total amount of FFA in the composition which has been treated with the lipolytic enzyme)−(total amount of FFA in the untreated composition)]/(total fatty acids present in the composition). The total amount of FFA and of total amount of fatty acid is expressed in mol/kg of substrate.

The lipolytic enzyme according to the invention has preferably a higher specificity towards the release of short chain free fatty acids, i.e. C4- to C10-free fatty acids, preferably C4-free fatty acids, if compared with the release of longer chain free fatty acids, i.e. C12- to C18-free fatty acids. In a preferred embodiment a lipolytic enzyme according to the invention has a degree of specificity towards C4- to C10-free fatty acids if compared with C12- to C18-free fatty acids which is expressed by the Specificity Ratio ($R_{spec}$) which is at least 0.4, preferably at least 0.5, more preferably at least 0.6 or 0.7, most preferably at least 0.8, 0.9, 1, 1.1, 1.5, 1.7, 2, 2.5, 3. Generally the $R_{spec}$ will be as high as possibly attainable.

$R_{spec}$ can be calculated as follows:

$$R_{spec} = \Sigma\text{Relative C4-C10 content}/\Sigma\text{Relative C12-C18 content}.$$

Wherein "ΣRelative C4-C10 content" is the sum of the relative content of C4-, C6-, C8- and C10-free fatty acids present in the composition which has been treated with a lipolytic enzyme and wherein "ΣRelative C12-C18 content" is the sum of the relative content of C12-, C14-, C16- and C18-free fatty acids present in the composition which has been treated with a lipolytic enzyme.

The "relative Cx content", wherein X can be any of 4, 6, 8, 10, 12, 14, 16, 18, corresponds to the percentage (%) of the amount of Cx-free fatty acid in the composition which has been treated with the lipolytic enzyme in respect with the total amount of free fatty acids present in the composition which has been treated with the lipolytic enzyme. The amount of FFA (or of free fatty acid) in the above mentioned formula is expressed in mol/kg.

The $R_{spec}$ is determined in a dairy composition made using young cheese (preferably Cheddar or Gouda cheese, preferably a young cheese with a ripening time of less than 2 weeks) and wherein the lipolytic enzyme is incubated under conditions (such as of dosage, incubation time and incubation temperature) that lead to a degree of fat conversion in the incubated sample comprised between 1%-25%, wherein the degree of fat conversion is calculated as indicated above.

The invention also relates to a dairy product which is obtainable by the method or any of the described uses according to the invention In a preferred embodiment of the use of any isolated peptide according to the invention or of the method to produce a dairy product according to the invention the ΣRelative C4-C10 content/ΣRelative C12-C18 content is at least 0.4, preferably at least 0.5, more preferably at least 0.6 or 0.7, most preferably at least 0.8, 0.9, 1, 1.1, 1.5, 1.7, 2, 2.5, 3. In e.g. Parmesan cheese treated with ruminant pregastric esterase this ratio is approximately 1.7 (calculated from data from D. T. Lai, A. D. Mackenzie, C. J. O'Connor, K. W. Turner *J. Dairy Sci.* 80:2249-2257 (1997), page 2255). Relative C4-C10 content" and "ΣRelative C12-C18" have the same meaning as above.

In the art it is known that when a lipolytic enzyme acting on a milk-fat containing substrate primarily releases short chain fatty acids (e.g. C4 and C6 fatty acids) this leads to the development of a piquant, sharp, spicy, tangy flavour, while e.g. release of medium chain fatty acid can lead to a soapy taste.

Therefore in a preferred embodiment of the use of the invention or of the method to produce a dairy product according to the invention, the polypeptide is used to develop flavour, preferably, the sharp, tangy, spicy notes in the flavour profile of the dairy product are increased, preferably the soapy notes in the flavour profile of the dairy product are decreased.

In a further aspect the invention relates to a dairy product obtainable by the method to prepare a dairy product according to the invention. Examples of suitable dairy products are those mentioned in the previous aspects of the invention.

Bakery Applications

Another example of an industrial application of the lipolytic enzyme according to the invention in food is its use in baking applications to improve dough and/or baked product quality.

A lipolytic enzyme according to the invention can show at least one of the following activities: lipase, phospholipase, galactolipase or lysolipase activity.

Glycerides and lipases have been defined above.

Glycolipids (e.g. galactolipids) consist of a glycerol backbone with two esterified fatty acids in an outer (sn-1) and middle (sn-2) position, while the third hydroxyl group is bound to sugar residues such as in case of galactolipids a galactose, for example monogalacosyldiglyceride or digalactosyldiglyceride. Galactolipase (EC 3.1.1.26) catalyses the hydrolysis of one or both fatty acyl group(s) in the sn-1 and sn-2 positions respectively from a galactosyldiglyceride.

Phospholipids consist of a glycerol backbone with two esterified fatty acids in an outer (sn-1) and the middle (sn-2) position, while the third hydroxyl group of the glycerol is esterified with phosphoric acid. The phosphoric acid may, in turn, be esterified to for example an amino alcohol like ethanolamine (phosphatidylethanolamine), choline (phosphatidylcholine). Phospholipases are defined herein as enzymes that participate in the hydrolysis of one or more bonds in the phospholipids.

Several types of phospholipase activity can be distinguished which hydrolyse the ester bond(s) that link the fatty acyl moieties to the glycerol backbone:

Phospholipase A1 (EC 3.1.1.32) and A2 (EC 3.1.1.4) catalyse the deacylation of one fatty acyl group in the sn-1 and sn-2 positions respectively, from a diacylglycerophospholipid to produce a lysophospholipid. This is a desirable activity for emulsifier replacement.

Lysophospholipase (EC 3.1.1.5—also called phospholipase B by the Nomenclature Committee of the International Union of Biochemistry and Molecular Biology (Enzyme Nomenclature, Academic Press, New York, 1992)) catalyses the hydrolysis of the remaining fatty acyl group in a lysophospholipid. A phospholipase B has been reported from *Penicil-*

*lium notatum* (Saito et al., 1991, Methods in Enzymology 197:446-456), which catalyses the deacylation of both fatty acids from a diacylglycerophospholipid and intrinsically possesses lysophospholipase activity. For emulsifier replacement lysophospholipase activity is less desirable, since this would result in deletion of the combination of a polar head and apolar tail, disabling the resulting product to influence surface properties. Surprisingly it was shown that the lipolytic enzyme according to the invention shows relatively low lysophospholipase activity in the dough.

Wheat flour contains approximately 2.2-2.9% lipids. The flour lipids can be divided into starch lipids (0.8-0.9%) and non-starch lipids (1.4-2.0%). Whereas the starch lipids consist mainly of polar lysophospholipids, the non-starch lipids consist of about 40% neutral triglycerides and 40% polar phospho- and glycolipids.

Baking enzymes may be used in a manifold of baked products. The term "baked products" is herein defined as to comprise bread products such as tin bread, loaves of bread, French bread as well as rolls, cakes, pies, muffins, yeast raised and cake doughnuts and the like.

A lipolytic enzyme according to the invention can for example be used in baked products. Baked products such as bread are prepared from a dough.

Therefore in one embodiment of the invention provides the use of an isolated polypeptide according to the invention in the preparation of a dough and provides a dough comprising the polypeptide according to the invention. The invention also provides the preparation of a dough comprising the steps of adding the polypeptide according to the invention to at least one of the dough ingredients.

Dough is usually made from the basic ingredients (wheat) flour, water and optionally salt. Depending on the baked products, other ingredients added may be sugars, flavours etceteras. For leavened products, primarily baker's yeast is used next to chemical leavening systems such as a combination of an acid (generating compound) and bicarbonate.

Yeast, enzymes and chemical additives are generally added separately to the dough.

Enzymes may be added in a dry, e.g. granulated form or in liquid form. The chemical additives are in most cases added in powder form. Also, processing aid compositions which are tailored to specific baking applications, may be composed of a dedicated mixture of chemical additives and enzyme.

The preparation of a dough from the ingredients and processing aids described above is well known in the art and comprises mixing of said ingredients and processing aids and one or more moulding and fermentation steps.

The preparation of baked products from such doughs is also well known in the art and may comprise moulding and shaping and further fermentation of the dough followed by baking at required temperatures and baking times. In one embodiment the invention provides a method to prepare a baked product comprising the step of baking the dough according to the invention. The invention also provides a baked product obtainable according to this method. Preferably the baked product according to the invention is bread.

The present invention also relates to methods for preparing a dough or a baked product comprising incorporating into the dough an effective amount of a lipolytic enzyme of the present invention which improves one or more properties of the dough or the baked product obtained from the dough relative to a dough or a baked product in which the polypeptide is not incorporated.

The phrase "incorporating into the dough" is defined herein as adding the lipolytic enzyme according to the invention to the dough, any ingredient from which the dough is to be made, and/or any mixture of dough ingredients from which the dough is to be made. In other words, the lipolytic enzyme according to the invention may be added in any step of the dough preparation and may be added in one, two or more steps. The lipolytic enzyme according to the invention is added to the ingredients of a dough that is kneaded and baked to make the baked product using methods well known in the art. See, for example, U.S. Pat. No. 4,567,046, EP-A-426, 211, JP-A-60-78529, JP-A-62-111629, and JP-A-63-258528.

The term "effective amount" is defined herein as an amount of the lipolytic enzyme according to the invention that is sufficient for providing a measurable effect on at least one property of interest of the dough and/or baked product.

The term "improved property" is defined herein as any property of a dough and/or a product obtained from the dough, particularly a baked product, which is improved by the action of the lipolytic enzyme according to the invention relative to a dough or product in which the lipolytic enzyme according to the invention is not incorporated. The improved property may include, but is not limited to, increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product and/or improved anti-staling of the baked product.

The improved property may be determined by comparison of a dough and/or a baked product prepared with and without addition of a polypeptide of the present invention in accordance with the methods of present invention which are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume and is evaluated by the ratio of height:width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g., TAXT2) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic.

The term "increased volume of the baked product" is measured as the volume of a given loaf of bread determined by an automated bread volume analyser (eg. BVM-3, TexVol Instruments AB, Viken, Sweden), using ultrasound or laser detection as known in the art.

The term "reduced blistering of the baked product" is defined herein as a visually determined reduction of blistering on the crust of the baked bread.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (eg. C-cell, Calibre Control International Ltd, Appleton, Warrington, UK).

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved anti-staling of the baked product" is defined herein as the properties of a baked product that have a reduced rate of deterioration of quality parameters, e.g., softness and/or elasticity, during storage.

The present invention provides a dough according to the invention having at least one of the improved properties selected from the group consisting of increased strength, increased elasticity, increased stability, reduced stickiness and/or improved extensibility of the dough.

The invention also provides a baked product according to the invention having increased loaf volume. The invention provides as well a baked product according to the invention having at least one improved property selected from the group consisting of increased volume, improved flavour, improved crumb structure, improved crumb softness, reduced blistering and/or improved anti-staling.

The term "dough" is defined herein as a mixture of flour and other ingredients firm enough to knead or roll. The dough may be fresh, frozen, pre-pared, or pre-baked. The preparation of frozen dough is described by Kulp and Lorenz in Frozen and Refrigerated Doughs and Batters.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, noodles (boiled or (stir-)fried), pita bread, tortillas, tacos, cakes, pancakes, biscuits, cookies, doughnuts, bagels, pie crusts, steamed bread, and crisp bread, and the like.

Lipolytic enzymes of the present invention and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme such described in WO01/11974 and WO02/26044. Granulates and agglomerated powders may be prepared by conventional methods, e.g., by spraying the lipolytic enzyme according to the invention onto a carrier in a fluid-bed granulator. The carrier may consist of particulate cores having a suitable particle size. The carrier may be soluble or insoluble, e.g., a salt (such as NaCl or sodium sulphate), sugar (such as sucrose or lactose), sugar alcohol (such as sorbitol), starch, rice flour, wheat flour, corn grits, maltodextrins, soy. The lipolytic enzyme according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

The lipolytic enzyme according to the invention may also be incorporated in yeast comprising compositions such as disclosed in EP-A-0619947, EP-A-0659344 and WO02/49441.

For inclusion in pre-mixes of flour it is advantageous that the polypeptide according to the invention is in the form of a dry product, e.g., a non-dusting granulate, whereas for inclusion together with a liquid it is advantageously in a liquid form.

One or more additional enzymes may also be incorporated into the dough. Therefore the invention provides a baking enzyme composition comprising the lipolytic enzyme according to the invention and one or more additional enzymes. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase,—such as an alpha-amylase (useful for providing sugars fermentable by yeast and retarding staling), beta-amylase, maltogenic amylase or non-maltogenic amylase—, cyclodextrin glucanotransferase, protease, peptidase, in particular, an exopeptidase (useful in flavour enhancement), transglutaminase, lipase (useful for the modification of lipids present in the dough or dough constituents so as to soften the dough), galactolipase, phospholipase, cellulase, hemicellulase, in particular a pentosanase such as xylanase (useful for the partial hydrolysis of pentosans, more specifically arabinoxylan, which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, hexose oxidase, e.g., a glucose oxidase, aldose oxidase, pyranose oxidase, lipoxygenase or L-amino acid oxidase (useful in improving dough consistency).

When one or more additional enzyme activities are to be added in accordance with the methods of the present invention, these activities may be added separately or together with the polypeptide according to the invention, optionally as constituent(s) of the bread-improving and/or dough-improving composition. The other enzyme activities may be any of the enzymes described above and may be dosed in accordance with established baking practices.

The present invention also relates to methods for preparing a baked product comprising baking a dough obtained by a method of the present invention to produce a baked product. The baking of the dough to produce a baked product may be performed using methods well known in the art.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide of the present invention. The baking additive preferably has a narrow particle size distribution with more than 95% (by weight) of the particles in the range from 25 to 500 µm.

In dough and bread making the present invention may be used in combination with the processing aids defined hereinbefore such as the chemical processing aids like oxidants (e.g. ascorbic acid), reducing agents (e.g. L-cysteine), and/or emulsifiers (e.g. DATEM, SSL and/or CSL), and/or any precursors of emulsifiers which can be a substrate for the lipolytic enzyme of the invention and/or enzymatic processing aids such as oxidoreductases (e.g. glucose oxidase), polysaccharide modifying enzymes (e.g. α-amylase, hemicellulase, branching enzymes, etc.) and/or protein modifying enzymes (endoprotease, exoprotease, branching enzymes, etc.).

In one embodiment the invention provides a baking composition comprising a lipolytic enzyme according to the invention and DATEM. DATEM is the acronym for diacetyl tartaric acid esters of mono- and diglycerides. One of the main components in DATEM may be 1-stearoyl-3-diacetyl-tartryl-glycerol.

The skilled man can easily determine suitable lipolytic enzyme and DATEM amounts to be used in the baking composition according to the invention. The optimal amounts of DATEM or of lipolytic enzyme respectively can first be determined whereby one or more properties of the dough or of the baking product produced with said dough are improved if compared with the properties of doughs or baked products obtained by neither adding DATEM nor lipolytic enzyme. Subsequently 30% to 50% w/w of optimal amount of each product can be used in the composition and the skilled man can verify by routine experimentation at which DATEM and lipolytic enzyme ratio in the composition a synergistic effect is observed.

In another preferred embodiment of the invention, the baking composition comprising DATEM and a lipolytic enzyme according to the invention is used in a method to produce a dough or a baked product of the invention.

The baking composition according to the invention may comprise next to a lipolytic enzyme according to the invention and to DATEM, one or more processing aids used in baking such as those mentioned above and/or one or more additional enzymes as described above. The baking composition comprising DATEM and the lipolytic enzyme according to the invention can be in any form suitable to be used in baking, such as in a solid or a liquid form. A composition in solid form can e.g. be a powder or a granulate. The liquid composition can be e.g. a water or an oil based composition and optionally may be stabilized. The baking composition comprising the lipolytic enzyme according to the invention and DATEM may also be part of a pre-mix as defined above. The baking composition comprising the lipolytic enzyme according to the invention and DATEM can be added as such to the flour used to prepare the dough. Optionally it can be formed directly in the dough by separately adding the lipolytic enzyme according to the invention and DATEM in the appropriate amounts to the dough ingredients.

A lipolytic enzyme according to the invention can be used in the production of cake and in the production of a batter from which a cake can be derived.

A lipolytic enzyme according to the invention can be used in all types of cake, including shortened cakes, such as for example pound cake and butter cake, and including foam cakes, such as for example meringues, sponge cake, biscuit cake, roulade, genoise and chiffon cake. Sponge cake is a type of soft cake based on wheat flour, sugar, baking powder and eggs (and optionally baking powder). The only fat present is from the egg yolk, which is sometimes added separately from the white. It is often used as a base for other types of cakes and desserts. A pound cake is traditionally prepared of one pound each of flour, butter, eggs, and sugar, optionally complemented with baking powder. In chiffon cake the butter/margarine has been replaced by oil. Sugar and egg yolk content has been decreased compared to pound or sponge cake and egg white content has been increased.

A lipolytic enzyme according to the invention can be used both in regular cakes and in cakes in which the amount of eggs and/or fat has been reduced. The reduction of the amount of eggs and/or fat which is possible differs per type of cake. The man skilled in the art knows the amount of eggs and/or fat which are regularly present in cake recipes and which is dependent on the type of cake. In general a reduction of the amount of eggs of at least 5% w/w can be reached. More preferably a reduction of the amount of eggs of at least 10% w/w can be reached, even more preferably a reduction of at least 15% w/w can be reached. It was shown that even a reduction of the amount of eggs used of at least 20% w/w can be reached. The reduction of the amount of eggs can be at least 30% w/w, 40% w/w or even at least 50% w/w.

In general a reduction of the amount of fat of at least 10% can be reached. More preferably a reduction of the amount of fat of at least 20% can be reached, even more preferably a reduction of at least 30% can be reached. It was shown that even a reduction of the amount of fat used of at least 50% can be reached.

In the International Patent Application number PCT/EP2008/051147 it has been disclosed that a phospholipase A can be used in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. In the same patent application it has also been disclosed that a phospholipase A can be used in the production of cake to enable reduction of the amount of eggs and/or fat used in the cake recipe. In particular it was shown that it was possible when using phospholipase A to reduce the amount of eggs and/or fat used in the recipe whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. The term at least maintaining is hereby used to indicate that a property is maintained or improved.

A composition comprising at least a phospholipase A and a lipolytic enzyme according to the invention can be used in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume.

In this context all types of phospholipase A can be used, for example phospholipase A1 or phospholipase A2. Any type of phospholipase A1 can be used. Phospholipase A1 is widespread in nature, e.g. in microorganisms *E. coli*, in snake venoms, and in mammals in the brain, testis and liver. An example of a suitable commercially available phospholipase A1 is Lecitase Ultra™ (Novozymes). Any type of phospholipase A2 can be used. Preferably a phospholipase A2 is used. An example of a suitable commercially available phospholipase A2 is Cakezyme™ (DSM) or Lecitase L10 (Novozymes). A preferred phospholipase A2 is porcine pancreatic phospholipase A2 for example expressed in *Aspergillus niger* (Cakezyme™, DSM).

Measuring whether a property is maintained, improved or deteriorated in general is measured by preparing a batter and/or a cake in an original recipe, not containing any phospholipase A and any lipolytic enzyme according to the invention and by preparing other batters and/or cakes in a recipe containing phospholipase A, optionally less eggs and/or fat and optionally the lypolitic enzyme according to the invention and comparing a certain property. In case the properties of the two batters or cakes to be compared are substantially the same, the property is maintained, in case they differ either an improvement or a deterioration has taken place. For all mentioned properties below a measurement method has been given as well as an indication when a property can be considered as improved.

The batter viscosity can be measured with a Faringograph by standard methods according to the International Association of Cereal Chemistry (ICC) and the American Association of Cereal Chemistry (AACC 54-2, ICC 115). Whether e.g. the batter viscosity of a batter made with reduced amount of eggs and/or fat and comprising phospholipase A and a lipolytic enzyme according to the invention has improved or deteriorated in respect with the same batter but comprising either phospholipase A alone or neither phospholipase A nor lipolytic enzyme can for example be measured as follow. In case the batter viscosity of a batter containing a reduced amount of eggs and/or fat and prepared with phospholipase A and the lipolytic enzyme according to the invention is the same as that of e.g. the same batter prepared without phospholipase A and without the lipolytic enzyme or is the same as that of e.g. the same batter prepared with phospholipase A only the batter viscosity has been maintained. In case the batter viscosity has increased, it has improved.

The specific batter density can be measured by weighing a predetermined volume of batter. The specific density is improved if it is decreased.

The crumb softness of the cake is evaluated either empirically by the skilled test baker or measured by the use of a texture analyzer (e.g., TAXT2) as known in the art. Actually crumb firmness of the cake is measured as is known to the person skilled in the art. The crumb softness measured within 24 hours after baking is called initial crumb softness. The crumb softness more than 24 hours after baking is called crumb softness upon storage, and is also a measure for determining shelf life. In case the initial crumb softness has increased, it has improved. In case the crumb softness upon storage has increased, it has improved.

Crumb pore homogeneity of the cake can be evaluated empirically by the skilled test baker or by digital image analysis as known in the art (e.g. C-cell, Calibre Control International Ltd, Appleton, Warrington, UK). In case the deviation in pore size is small, the crumb is called more homogeneous. In case the deviation in pore size has become smaller, the property is improved.

Crumb pore diameter of the cake can be evaluated using digital image analysis as known in the art (e.g. C-cell, Calibre Control International Ltd, Appleton, Warrington, UK). In case the average crumb pore diameter decreases, the property is improved. Preferably, this is the case when at the same time the same cake volume is maintained.

The shelf-life of the cake can be measured by determining the resilience of the cake in time. This is part of the method to measure crumb softness, as is known to the person skilled in the art, whereby the relaxation of the cake is also measured by the use of a texture analyzer (e.g., TAXT2) as known in the art.

The volume of a given cake can be determined by an automated bread volume analyser (eg. BVM-3, TexVol Instruments AB, Viken, Sweden), using ultrasound or laser detection as known in the art. In case the volume is increased, the property is improved. Alternatively the cake height after baking in the same size tin is an indication of the cake volume. In case the cake height is increased, the cake volume has increased.

The emulsion stability of the batter can be determined by determining the cake height and visual analysis of the cake structure. In case the cake height has decreased, the emulsion stability of the batter has decreased. In case the cake structure is more dense, the emulsion stability of the batter also has decreased.

The present invention provides the use of a composition comprising a lipolytic enzyme according to the invention and phospholipase A in the production of cake to improve at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume. The present invention also provides the use of a composition comprising a lipolytic enzyme according to the invention and phospholipase A in the production of cake to enable reduction of the amount of eggs and/or fat used in the cake recipe, preferably whilst at least maintaining at least one of the properties selected from the group consisting of: (i) batter viscosity, (ii) specific density, (iii) initial crumb softness, (iv) crumb pore homogeneity, (v) crumb pore diameter, (vi) crumb softness upon storage, (vii) shelf life and/or (viii) cake volume.

The skilled man can easily determine suitable amounts of respectively phospholipase A and a lipolytic enzyme according to the invention to be used in the composition depending on the cake recipe and type.

Optionally one or more other ingredients can be present in the composition, next to phospholipase A and to the lipolytic enzyme according to the invention, e.g. to allow reduction of eggs and/or fat in the cake such as e.g. alternative protein sources, hydrocolloids, modified starch, yeast extract, calcium. Preferable ingredients are yeast extract, modified starch, calcium.

A yeast extract may be used which comprises at least 30% w/w 5'-ribonucleotides, preferably at least 34% w/w, 38% w/w, 40% w/w or 42% w/w, more preferably at least 44% w/w, 46% w/w, 48% w/w or at least 50% w/w 5'-ribonucleotides on the basis of sodium chloride free dry matter. It has been found that the use of such yeast extract not only improves the taste of the cake, but also has a surprising emulsifying effect, since upon its use, the viscosity of the batter improves.

In the context of the present invention, the phrase "5'-ribonucleotides" refers to the total amount of 5'-monophosphate ribonucleotides formed during RNA degradation, viz. 5'-monophosphate guanine (5'-GMP), 5'-monophosphate uracil (5'-UMP), 5'-monophosphate cytosine (5'-CMP), 5'-monophosphate adenine (5'-AMP), where 5'-AMP may be partially or completely converted into 5'-monophosphate inosine (5'-IMP). For example, in a yeast extract which comprises 30% w/w 5'-ribonucleotides on the basis of sodium chloride free dry matter, the total amount of 5'-GMP, 5'-UMP, 5'-CMP, 5'-AMP and 5'-IMP is 30% w/w on the basis of sodium chloride free dry matter. In a preferred embodiment, a yeast extract is used wherein the total amount of 5'-GMP plus 5'-IMP is at least 15% w/w, preferably at least 17% w/w, 19% w/w, 20% w/w or 21% w/w, more preferably at least 22% w/w, 23% w/w, 24% w/w or 25% w/w, on the basis of sodium chloride free dry matter. Due to the constitution of RNA, from which the 5'-ribonucleotides arise, 5'-GMP and 5'-IMP will always be present in approximately equal amounts in this embodiment. In the context of the present invention, weight percentage calculations of the 5'-ribonucleotides are based on the disodium salt heptahydrate thereof unless otherwise specified. All percentages are calculated on sodium chloride free dry matter. In the present invention, the phrase 'sodium chloride free dry matter' refers to the fact that for the calculation of the weight percentage the weight of any sodium chloride present in the yeast extract is excluded from the composition. The measurement of sodium chloride in the yeast extract and the above-mentioned calculation can be performed by methods known to those skilled in the art. An example of yeast extracts comprising 40% w/w 5'-ribonucleotides of which 20% w/w 5'-GMP plus 5'-IMP, weight percentages being based on sodium chloride free yeast extract dry matter, is sold under the trademark Maxarite® Delite (DSM Food Specialties, The Netherlands).

Modified starch can be used to reduce the amount of fat used in the cake recipe even further. All types of modified starch can be used, for example modified potato starch or modified wheat starch. Preferably modified potato starch is used, such as for example disclosed in U.S. Pat. No. 6,864,063. Most preferably modified potato starch is used which is obtained by treating potato starch with amylomaltase. An example of preferred modified potato starch is sold under the trademark Etenia® (Avebe Food). It has been surprisingly found that in cakes comprising a reduced amount of fat, e.g. as low as 30% w/w, and which are prepared using a combination of phospholipase A, a lipolytic enzyme according to the invention and modified potato starch, desired cake properties as those mentioned above, e.g. batter viscosity, are improved if compared with cakes produced by using 30% w/w less fat and no addition of phospholipase A, lipolytic enzyme and modified potato starch.

Calcium is preferably added to enhance the activity of the phospholipase A. It has been found especially advantageous to add approximately between 40-200 mg $CaCl_2.H_2O$ per 5,000 CPU Phospholipase A (hereafter indicated as PLA) to the cake recipe. Preferably, between 50 and 150 mg $CaCl_2.H_2O$ per 5,000 CPU PLA is added to the cake recipe and most preferably at least 90 mg $CaCl_2.H_2O$ per 5,000 CPU PLA. CPU (Chromogenic Phospholipase Unit=1 EYU (Egg Yolk Unit) is defined as the amount of enzyme that liberates 1 µmol of acid per minute from egg yolk at 40° C. and pH8.0. Substrate in this method: rac 1,2-dioctanoyldithio phosphatidylcholine measured spectrophotometric at 405 nm. Surprisingly, has been found that the cake batter does not provide enough calcium for the phospholipase A to work efficiently.

The invention further provides a method to prepare a batter or a method to prepare a cake wherein a composition comprising a phospholipase A and a lipolytic enzyme according to the invention is added to the cake ingredients.

Typical ingredients of the cake are wheat flour, eggs and sugar. Optionally, baking powder, salt, water, emulsifiers (such as for example PGE's and monoglycerides), margarine, butter and/or oil are added (for example for pound cakes and muffins).

A method to prepare a batter according to the invention preferably comprises the steps of:
preparing the batter of the cake by adding at least:
sugar
flour
phospholipase A, the lipolytic enzyme according to the invention and eggs
A method to prepare a cake according to the invention further comprises the step of
baking the batter to yield a cake According to the above-mentioned method both cakes comprising a reduced amount of eggs and/or fat and cakes where no eggs and/or fat reduction has been applied can be prepared.

The man skilled in the art knows how to prepare a batter or a cake starting from cake ingredients. Optionally one or more other ingredients can be present in the composition e.g. to allow reduction of eggs and/or fat in the cake, such as protein sources, hydrocolloids, yeast extract, modified starch, calcium. Preferable ingredients are yeast extract, modified starch, calcium as defined above.

The invention further provides a cake or a batter obtainable by the method mentioned above. The invention also provides a baking composition, which may for example be used in the production of cake or batter, comprising a phospholipase A and a lipolytic enzyme according to the invention. This baking composition can also be used in dough products and baked products obtained from such dough. For example it can be used in dough products further containing eggs and in baked products derived thereof, such as brioche and panettone, both regular and with a reduced amount of eggs.

Said baking composition can also be part of a cake pre-mix comprising also flour and optionally other ingredients.

The above-mentioned industrial applications of a lipolytic enzyme according to the invention comprise only a few examples and this listing is not meant to be restrictive.

A lipolytic enzyme may conveniently be produced in micro-organisms. In the above processes, it is advantageous to use lipolytic enzyme that are obtained by recombinant DNA techniques. Recombinant enzymes may be produced at a low cost price, high yield, free from contaminating agents like bacteria or viruses but also free from bacterial toxins or contaminating other enzyme activities.

Other Applications

Other applications for a lipolytic enzymes described herein are their use as an emulsifier, their use in detergents (for removing (animal) fat) or their use for cleaning waste pipes for example waste pipes of kitchens in which fat is used.

Composition

In yet another embodiment, the invention provides a composition comprising a polypeptide as described herein (i.e. an enzyme with lipolytic activity) and an acceptable carrier or preservative. Alternatively, the invention provides a composition comprising a polypeptide as described herein (i.e. an enzyme with lipolytic activity) and a second enzyme. Preferably, said second enzyme is an aspartic protease or a phospholipase. In an embodiment of the invention, the aspartic protease is a *Rhizomucor miehei* aspartic protease. The term "*Rhizomucor miehei* aspartic protease" encompasses the aspartic protease homologously produced in *Rhizomucor miehei*. A process for the preparation of the enzyme via fermentation is described in U.S. Pat. No. 3,988,207. The term "*Rhizomucor miehei* aspartic protease" also encompasses a recombinant *Rhizomucor miehei* aspartic protease, for example a *Rhizomucor miehei* aspartic protease produced in a host organism (e.g. other than *Rhizomucor miehei*) transformed with DNA coding for the *Rhizomucor miehei* aspartic protease. A method for the production of a recombinant *Rhizomucor miehei* aspartic protease in a host organism is described in EP-A-700253. In another embodiment of the invention the aspartic protease is chymosin. Chymosin may for instance be extracted from the stomach of a calf, camel or seal. In a preferred embodiment of the invention the chymosin is produced by a microorgansim, e.g. via recombinant DNA technology in bacteria, e.g. *Escherichia coli*, yeast, e.g. *Kluyveromyces lactis*, or filamentous fungi, e.g. in *Aspergillus niger*. Phospholipases have been described in the section "bakery applications" and apply also to this section.

Hereafter the invention is illustrated by the following non-limiting examples.

EXAMPLES

Materials and Methods

*A. niger* Strains

WT 1: This *A. niger* strain is used as a wild-type strain. This strain is deposited at the CBS Institute under the deposit number CBS 513.88.

WT 2: This *A. niger* strain is a WT 1 strain comprising a deletion of the gene encoding glucoamylase (g/aA). WT 2 was constructed by using the "MARKER-GENE FREE" approach as described in EP 0 635 574 B1. In this patent it is extensively described how to delete g/aA specific DNA sequences in the genome of CBS 513.88. The procedure resulted in a MARKER-GENE FREE ΔglaA recombinant *A. niger* CBS 513.88 strain, possessing finally no foreign DNA sequences at all.

WT 3: To disrupt the pepA gene encoding the major extracellular aspartic protease PepA in WT 2, pepA specific DNA sequences in the genome of WT 2 were deleted, as described by van den Hombergh et al. (van den Hombergh J P, Sollewijn Gelpke M D, van de Vondervoort P J, Buxton F P, Visser J. (1997)—Disruption of three acid proteases in *Aspergillus niger*—effects on protease spectrum, intracellular proteolysis, and degradation of target proteins—Eur J. Biochem. 247 (2): 605-13). The procedure resulted in a MARKER-GENE FREE WT 3 strain, with the pepA gene inactivated in the WT 2 strain background.

WT 4: To delete the hdfA gene in WT 3, the method as earlier described in detail in WO05/095624 was used to generate *Aspergillus niger* WT 4 (ΔglaA, ΔpepA, ΔhdfA).

WT 5: This *A. niger* strain is a WT 4 strain comprising a deletion which results in an oxalate deficient *A. niger* strain. WT 5 was constructed by using the method as described in EP1157100 and U.S. Pat. No. 6,936,438, in which an oxalate deficient strain was obtained by deletion of the oahA gene, encoding oxaloacetate hydrolase, Strain WT 5 was selected as a representative strain with the oahA gene inactivated in the WT 4 strain background.

WT 6: This *A. niger* strain is a WT 5 strain comprising the deletion of three genes encoding alpha-amylases (amyB, amyBI and amyBII) in three subsequent steps. The construction of deletion vectors and genomic deletion of these three genes has been described in detail in WO2005095624. The vectors pDEL-AMYA, pDEL-AMYBI and pDEL-AMYBII, described in WO2005095624, have been used according the "MARKER-GENE FREE" approach as described in EP 0 635 574 B1. The procedure described above resulted in WT 6, an oxalate deficient, MARKER-GENE FREE ΔglaA, ΔpepA, ΔhdfA, ΔamyA, ΔamyBI and ΔamyBII amylase-negative recombinant *A. niger* CBS 513.88 strain, possessing finally no foreign DNA sequences at all. As such, strain WT 6 has a low amylase background, has a higher HR/NHR ratio for more efficient targeting of sequences and is more optimized for extracellular protein expression and detection compared to WT 1.

Description of *K. lactis* Strains

To assess the expression of PGE and its variants in *K. lactis* two strains were tested. GG799 (New England Biolabs) and a derivative of *K. lactis* CBS 685.97, WT 4, that is in more detail describe in U.S. Pat. No. 6,265,186 B1. *K. lactis* WT 4 was derived from CBS685.97 by means of mutagenesis (classical strain improvement) and genetic engineering.

*A. niger* Shake Flask Fermentations

Fresh spores ($10^6$-$10^7$) of *A. niger* strains were inoculated in 20 ml CSL-medium (100 ml flask, baffle) and grown for 20-24 hours at 34° C. and 170 rpm. After inoculation of 5-10 ml CSL pre-culture in 100 ml CSM medium (500 ml flask, baffle) the strains were fermented at 34° C. and 170 rpm for up to 5 days.

The CSL medium consisted of (in amount per liter): 100 g Corn Steep Solids (Roquette), 1 g $NaH_2PO_4*H_2O$, 0.5 g $MgSO_4.7H_2O$, 10 g glucose*$H_2O$ and 0.25 g Basildon (antifoam). The ingredients were dissolved in demi-water and the pH was adjusted to pH 5.8 with NaOH or $H_2SO_4$; 100 ml flasks with baffle and foam ball were filled with 20 ml fermentation medium and sterilized for 20 minutes at 120° C. after which 200 μl of a sterile solution containing 5000 IU/ml penicillin and 5 mg/ml Streptomycin was added to each flask after cooling to room temperature.

The CSM medium consisted of (in amount per liter): 150 g maltose*$H_2O$, 60 g Soytone (peptone), 1 g $NaH_2PO_4$*H2O, 15 g $MgSO_4.7H_2O$, 0.08 g Tween 80, 0.02 g Basildon (antifoam), 20 g MES, 1 g L-arginine. The ingredients were dissolved in demi-water and the pH was adjusted to pH 6.2 with NaOH or $H_2SO4$; 500 ml flasks with baffle and foam ball were filled with 100 ml fermentation broth and sterilized for 20 minutes at 120° C. after which 200 μl of a sterile solution containing 5000 IU/ml penicillin and 5 mg/ml Streptomycin was added to each flask after cooling to room temperature.

*K. lactis* Shake Flask Fermentations

A single colony of a *K. lactis* PGE transformant was inoculated into 100 ml (flask) of YEP (4%)-D/MES medium that contained per liter: 10 g yeast extract, 20 g bacto peptone, 40 g glucose and 100 mM MES pH 6.7. The fermentation was performed at 30° C. in a shake incubator at 280 rpm. Supernatant was collected at day 2 and 3 and further analysed as describe below.

SDS-PAGE Electrophoresis

Sample Pre-Treatment

30 μl sample was added to 35 μl water and 25 μl NuPAGE™ LDS sample buffer (4×) Invitrogen and 10 μl NuPAGE™ Sample Reducing agent (10×) Invitrogen. Samples were heated for ten minutes at 70° C. in a thermo mixer.

SDS-PAGE

SDS-PAGE was performed in duplicate according to the method based on the manual Novex Pre-Cast Gel Electrophoresis Guide (version B, 2003) from Invitrogen. One of the two gels was used for blotting, 10 μl of the sample solutions and 1 μl marker M12 (Invitrogen) were applied on the gels (NuPAGE™ BisTris, Invitrogen).

The gels were run at 200V, using the XCELL Surelock, with 600 ml 20 times diluted MES-SDS buffer in the outer buffer chamber and 200 ml 20 times diluted MES-SDS buffer, containing 0.5 ml of antioxidant (NuPAGE™ Invitrogen) in the inner buffer chamber. After running, the gels were fixed for one hour with 50% Methanol/7% Acetic acid (50 ml), rinsed twice with demineralised water and stained with Sypro Ruby (50 ml, Invitrogen) overnight.

Images were made using the Typhoon 9200 (610 BP 30, Green (532 nm), PMT 600V, 100 micron) after washing the gel for ten minutes with demineralised water.

Conditions of the Electrophoresis
Gel: 4-12% Bis-Tris gel
Buffer: MES SDS running buffer
Runtime: 35 minutes Western Blotting Western blotting was performed in an Xcell II Blot Module on an Xcell Surelock Mini-Cell electrophoresis unit from Invitrogen. The method was based on the manual Novex Pre-Cast Gel Electrophoresis Guide (version B, 2003) from Invitrogen.

membrane: NC 0.45 µm
Runtime: 90 minutes at 25V
Buffer: transfer buffer with methanol After the transfer to the membrane the following steps were performed:

Block the membrane in 20 ml skim milk (1% skim milk in PBST; 10 mM PBS+0.05% TWEEN20) for two hours.
Rabbit polyclonal antibody against PGE; dissolve 40 µl Antibody in 20 ml PBST) overnight at room temperature (1:500).
Rinse membrane with PBS-T and wash next 3×20' with PBST buffer.
Antibody 2: ECL Plex Goat Anti-Rabbit IgG Cy3 (GE Healthcare); dissolve 10 µl ECL
Plex in 25 ml PBST, keep in dark) 1 hour (1:2500)
Rinse membrane 4 times and wash next 2×10' in PBST
Wash 2×10' in PBS An image was made of the membrane using the Typhoon 9200 (670 BP 30, green (532 nm), PMT 450V, 100 micron).

PGE Polyclonal Antibody

PGE polyclonal antibodies were ordered at Eurogentec (Belgium) using the speedy 28-days program and two synthesized PGE peptides as antigens. The PGE antibody was validated against the commercial Piccantase C (DFS) enzyme preparation (data not shown).

Tributyrine Plate Assay

Rhodamine B Lipase Plate Screening Assay with Tributyrin (C4) as a Substrates.

The Rhodamine B plate assay is commonly used for the screening of lipase activity presence in the samples and was adapted from assay described in literature (G. Kouker, K. E. Jaeger, Applied and Environmental Microbiology, 1987, 211-213).

All chemicals used were analytical grade. The 0.1M Acetate BS pH=5.5 was used.

Arabic gum emulsion was made by dissolving 17.9 g NaCl and 0.41 g $KH_2PO_4$ in 400 ml of $H_2O$ and finally 540 ml of glycerol (87%) was added. Six (6.0) g of Arabic gum is slowly added and after dissolving the total volume of 1000 ml was achieved by adding of $H_2O$.

Rhodamine B solution was prepared by dissolving Rhodamine B at concentration of 20 mg/ml in ethanol.

Four (4) % Agarose solution was prepared by dissolving 4 g agarose in 100 ml buffer solution and warmed up in microwave until it became homogeneous liquid.

Substrate used to screen lipase activity was tributyrin.

Assay Procedure:

For 15 ml final solution: add 1 ml of substrate and 1.5 ml Arabic gum emulsion to 5 ml buffer solution and sonificate using Soniprep with an amplitude of 20 micron for 2×60 sec or optionally Ultraturex set at green for 2 minutes. To this solution add 7.5 ml of hot agarose solution and 150 µl of Rhodamine B. Pour the final solution in one-well Petri dish plate and equalize. After cooling keep plates in the refrigerator until the use. Just before the use make holes of 3 mm diameter using replicator. Ten (10) µl of solution that has to be checked for the lipase activity has to be pipetted into each hole. The plate has to be incubated at 37° C. for 18-24 hours. The fluorescent halo around the hole indicates lipase activity.

pNP-Butyrate Assay—1—

Pre-Gastric Esterase (PGE) activity was determined at 37° C. on a final concentration of 1 mM para-nitrophenyl butyrate as substrate against an internal enzymatic standard. To 120 µl of 0.1 M sodium phosphate buffer pH 6.7 containing 0.2% BSA, 15 µl of substrate solution was added. After preheating to 37° C., 15 µl of sample in an appropriate dilution was added (dilution in 0.1 M sodium phosphate buffer pH 6.7 containing 0.2% BSA), after which the absorbance increase over 5 minutes of incubation at 37° C. was measured photometrically at 405 nm.

The substrate solution was prepared by making a 50 mM para-nitrophenyl butyrate stock solution in acetonitril, which was diluted five times in 0.1 M sodium phosphate buffer pH 6.7 containing 0.2% BSA and 2% Triton X-100.

Sample responses were corrected for a blank background (incubation of 15 µl of 0.1 M sodium phosphate buffer pH 6.7 containing 0.2% BSA instead of sample) and typically ranged from 0.05 to 0.5 dAbs after blank correction.

The internal standard was calibrated in a titrimetric assay on tributyrin, performed at pH 6.0 and 30° C. Five ml of a PGE sample solution (prepared in milliQ water) were added to 30 mL of a pre-heated tributyrin/Arabic gum emulsion (93 and 57 g/L in water, respectively). Free fatty acid release was measured over 5 minutes by titration with 0.02 N NaOH.

This assay is considered to be an assay which results in relative amounts of lipase pNP-Butyrate Assay—2—

Pre-Gastric Esterase (PGE) activity was determined at 37° C. on a final concentration of 1 mM para-nitrophenyl butyrate as substrate. To 120 µl of 0.1 M sodium phosphate buffer pH 6.7 containing 0.2% BSA, 15 µl of substrate solution was added. After preheating to 37° C., 15 µl of sample in an appropriate dilution was added (dilution in 0.1 M sodium phosphate buffer pH 6.7 containing 0.2% BSA), after which the absorbance increase over 5 minutes of incubation at 37° C. was measured photometrically at 405 nm. The substrate solution was prepared by making a 50 mM para-nitrophenyl butyrate stock solution in acetonitril, which was diluted five times in 0.1 M sodium phosphate buffer pH 6.7 containing 0.2% BSA and 2% Triton X-100.

Sample responses were corrected for a blank background (incubation of 15 µl of 0.1 M sodium phosphate buffer pH 6.7 containing 0.2% BSA instead of sample) and typically ranged from 0.05 to 0.5 dAbs after blank correction.

Activity was expressed as the amount of para-nitrophenol released from the substrate in µmol/min under the conditions of the test. Activity calculation was done based on determination of the molar extinction coefficient of para-nitrophenol under assay conditions.

This assay is considered to be an assay which results in absolute amounts of lipase and is preferably used.

Example 1

Construction of PGE Expression Vectors Containing the Wild Type Gene and its Codon-Pair Optimized Variant The full length cDNA sequence of calf pregasteric esterase was published by Timmermans et. al (1994, Gene 147: 259-262). For testing the expression of PGE in eukaryotic production micro-organisms such as *Kluyveromyces lactis* and *Aspergillus niger* this sequence was codon pair optimized using in house developed algorithm. All genes were prepared synthetically (Sloning or GeneArt Germany).

*A. niger*

For expression of PGE in *A. niger* several expression construct variants were prepared (Table 6). The variables were: the codon usage, the type of the signal sequence or the leader protein and the pre(pro-)sequence processing site.

TABLE 6

*A. niger* constructs

| Name of construct | Protein | PGE gene | Signal sequence (s.s.) or carrier protein | KexB site |
|---|---|---|---|---|
| pANPGE-1 | ANPGE-1 | wildtype (SEQ ID NO. 3) | tAG | yes (KR) |
| pANPGE-2 | ANPGE-2 | wildtype | tAG | no |
| pANPGE-3 | ANPGE-3 | CPO (SEQ ID NO. 15) | tAG | yes (KR) |
| pANPGE-4 | ANPGE-4 | CPO | tAG | no |
| pANPGE-7 | ANPGE-7 | wildtype | native PGE | native | tAG—truncated glucoamylase from *A. niger* (498 amino acids) used as carrier protein.

Figure 1:
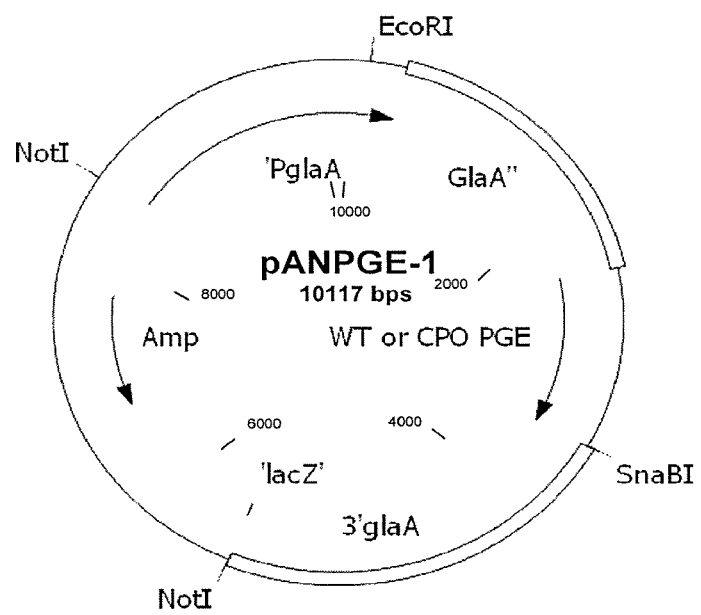
FIG. 1 *A. niger* expression vector—example for pANPGE-1.

The PGE encoding gene was expressed in *A. niger* from an expression vector shown in FIG. 1. The PGE encoding gene (wild type or codon pair optimized) was prepared synthetically as a fusion to the carrier protein (tAG) or the signal sequence (PGE wt). The fusion fragment was inserted into an *A. niger* expression vector as shown for pANPGE-1 in FIG. 1.

*K. lactis*

For expression of PGE in *K. lactis* the following expression constructs were made (Table 7). The variables were: the codon usage, the type of the signal pre(pro-) sequence and the pre(pro-)-sequence processing site.

TABLE 7

*K. lactis* constructs

| Name of construct | Protein | PGE gene | Signal sequence (s.s.) | Kex processing site |
|---|---|---|---|---|
| pKLPGE-1 | KLPGE-1 | wildtype (SEQ ID NO. 3) | α-factor s.s. *K. lactis* | KR |

TABLE 7-continued

*K. lactis* constructs

| Name of construct | Protein | PGE gene | Signal sequence (s.s.) | Kex processing site |
|---|---|---|---|---|
| pKLPGE-2 | KLPGE-2 | wildtype | α-factor s.s. *K. lactis* | KREAEA |
| pKLPGE-3 | KLPGE-3 | CPO (SEQ ID NO. 1) | α-factor s.s. *K. lactis* | KR |
| pKLPGE-4 | KLPGE-4 | CPO | α-factor s.s. *K. lactis* | KREAEA |
| pKLPGE-5 | KLPGE-5 | wildtype | native | native |

The PGE encoding genes were synthesized (Sloning or GeneArt, Germany) as a fusion with the signal pre(pro-) sequence and they were cloned via HindIII and NotI restriction sites to the pKLAC1 *K. lactis* expression vector (New England Biolabs). Another *K. lactis* expression vector (pKLPGE) was also tested that contains few modifications compared to pKLAC1 (see FIG. 8).

Example 2

Mutant Variants of PGE for Expression in *K. lactis* and *A. Niger*

Due to difficulties with expression of PGE in *A. niger* and *K. lactis*, namely caused by sticking of the enzyme to biomass, several PGE mutant variants affected in the number of glycosylation sites or hydrophilicity (or changing the polarity) were designed, see Table 8 and Table 9. pI mutants are also charge (hydrophilicity) mutants in order to make the surface more polar. However the charge distribution with respect to negative and positive charges is different. In case of the so-called pI mutants the distribution positive/negative charges has been shifted towards more negative charges (lys/arg>>Asp/glu) resulting in a lower pI. For the hydrophobicity mutant variants the charge distribution with respect to positive/negative is more or less kept the same as the pI of the wild type PGE or was allowed to shift towards more alkaline pI.

Here we show the examples of expression of different mutant variants with codon pair optimized nucleotide sequence in *K. lactis* and *A. niger*. The PGE mutant variants encoding genes were made synthetically and cloned in the *K. lactis* and *A. niger* expression vectors as described above.

TABLE 8

Mutants of PGE expressed in *K. lactis*

| Mutant number nt sequence | Name of mutant construct | Mutant protein | Modification compared to wildtype native PGE sequence (SEQ ID NO. 2) |
|---|---|---|---|
| 1 SEQ ID NO. 4 | pKLPGE-8 | KLPGE-8 | 1 extra glycosylation site was added by modifying amino acid K98 to N (SEQ ID NO. 5) |
| 2 SEQ ID NO. 6 | pKLPGE-9 | KLPGE-9 | 5 extra glycosylation sites were added by modifying amino acids: A70 to S K98 to N R158 to N and R159 to K H318 to N and P320 to S I361 to T (SEQ ID NO. 7) |
| 3 SEQ ID NO. 8 | pKLPGE-11 | KLPGE-11 | pI shift of 6.96 to 7.74; number of polar residues was increased from 165 to 181 and number of charged amino |

TABLE 8-continued

Mutants of PGE expressed in K. lactis

| Mutant number nt sequence | Name of mutant construct | Mutant protein | Modification compared to wildtype native PGE sequence (SEQ ID NO. 2) |
|---|---|---|---|
| 4 SEQ ID NO. 10 | pKLPGE-12 | KLPGE-12 | acids residues from 80 to 91 (for alignment with PGE wt see FIG. 2) (SEQ ID NO. 9) pI shift from 6.96 to 6.7; number of polar residues was increased from 165 to 188 and number of charged amino acids residues from 80 to 103 (for alignment with PGE wt see FIG. 3) (SEQ ID NO. 11) |
| 5 SEQ ID NO. 12 and 14 | pKLPGE-10 | KLPGE-10 | PGE variant with native signal sequence fused to α-MAT factor signal pre(pro-)sequence (SEQ ID NO. 2) |

TABLE 9

Mutants of PGE expressed in A. niger

| Mutant number nt sequence | Name of mutant construct | Mutant protein | Modification compared to wildtype native PGE sequence (SEQ ID NO. 2) |
|---|---|---|---|
| 1 SEQ ID NO. 16 | pANPGE-10 | ANPGE-10 | 5 extra glycosylation sites were added by modifying amino acids: A70 to S K98 to N R158 to N and R159 to K H318 to N and P320 to S I361 to T (SEQ ID NO.) |
| 2 SEQ ID NO. 17 | pANPGE-16 | ANPGE-16 | pI shift from 6.96 to 6.7; number of polar residues was increased from 165 to 188 and number of charged amino acids residues from 80 to 103 (SEQ ID NO.) |
| 3 SEQ ID NO. 19 | pANPGE-12 | ANPGE-12 | pI shift from 6.96 to 4.6, number of polar residues was increased from 165 to 186 and number of charged amino acids residues from 80 to 88 |
| 4 SEQ ID NO. 21 | pANPGE-13 | ANPGE-13 | pI shift from 6.96 to 4.88, number of polar residues was increased from 165 to 180 and number of charged amino acids residues from 80 to 83 |

Example 3

Transformations of A. niger and K. lactis with the PGE Wild Type Expression Constructs and Screening of PGE Expressing Transformants A. niger A. niger WT 6 was co-transformed with a plasmid carrying the A. nidulans amdS selection marker (see FIG. 4) and a plasmid containing a PGE construct (Table 6). For each of the transformations, 20 colonies were purified on selective medium containing acetamide and subsequently spore plates were prepared, all as described in WO99/32617.

The spores were harvested as described above and the shake flask fermentations were performed in CSL/CSM medium. At day 2 and day 5 supernatant samples were collected and screened for lipase activity using the tributyrine plate assay. Only in samples harvested from the pANPGE-3 and pANPGE-4 A. niger transformants activity halos could be detected (data not shown). To confirm that all the selected A. niger transformants were true co-transformants, e.g. that they contained both plasmids, a genetic check was performed (not shown). The result confirmed that among the 20 selected transformants at least 50% contained one or more copies of the PGE expressing construct. This result indicated that active PGE could be produced in A. niger using the codon pair optimized PGE sequence expressed as a fusion protein to truncated glucoamylase.

The pANPGE-3 and pANPGE-4 A. niger WT 6 transformants showing the largest halo on the tributyrine plate assay were examined for expression of PGE using SDS-PAGE (Invitrogen). Only in the strains carrying the PGE constructs lacking KexB processing site the PGE protein could be clearly visualized as a fusion to tAG in the early stages of the fermentation (day 2, see FIG. 5). The transformants containing constructs with the KexB site showed a band of MW about 50 kDa becoming more visible by prolonged treatment of broth with Triton X-100. It could correspond to PGE. Treating of the biomass with TritonX-100 let to further release of the protein to the supernatant indicating that the produced PGE enzyme sticks to the biomass (not shown). The PGE enzyme produced by A. niger was examined in a cheese application test for its specificity to hydrolyze short fatty acids from milk fat. The results confirmed that the cloned gene expressed PGE protein with the right enzymatic specificity (not shown).

K. lactis

K. lactis GG799 or K. lactis WT 4 was transformed with the PGE containing K. lactis expression plasmid (pKLAC1 or pKLPGE). For each of the transformations, 20 colonies were purified on selective medium containing acetamide. A single colony was used to inoculate a yeast fermentation medium to access the production of PGE. Supernatant was collected at day 2 and 3 and it was screen for lipase activity on a plate assay containing tributyrine as an enzymatic substrate (see above). No clear activity halo could be detected on the plate (data not shown). Also analysis of the supernatant on SDS-PAGE for PGE production did not show a positive result. Two pKLPGE-3 *K. lactis* transformants containing a single copy and three copies of the codon pair optimized PGE gene were further fermented on larger scale basis.

Example 4

Screening of the *K. Lactis* PGE Mutant Transformants

*K. lactis* GG799 or *K. lactis* WT 4 was transformed with 5 PGE mutant variants (Table 8) and the transformants were selected as described above (example 3). Surprisingly, 4 out of the 5 PGE mutants showed a clear activity halo (not shown). An activity halo was never seen before when examining the supernatant of the PGE wt *K. lactis* transformants. Only the pKLPGE-10 *K. lactis* transformants did not show lipase activity. To confirm that the selected amdS positive pKLPGE-10 transformants contained the PGE expression construct a genetic check was performed (data not shown). Indeed, all 20 amdS positive pKLPGE-10 *K. lactis* transformants also contained the PGE expression construct.

For each construct, pKLPGE-8, pKLPGE-9, pKLPGE-11 and pKLPGE-12, 3 transformants showing the largest halo on the tributyrine plate assay were examined for lipase activity using pNP-butyrate as a substrate (see above). The summary of various activity assays for the PGE mutants is shown in Table 10. For *K. lactis* pKLPGE-3 (PGE CPO) transformants (various copy number) maximum activity of 0.2 U/ml was obtained. Here, an increase in activity more than 50× was observed for the PGE mutant variant no. 4, PGE-12. A number of mutants of the PGE-9, PGE-11 and PGE-12 variants were fermented on a larger scale basis.

*K. lactis* GG799 is the corresponding yeast host cell without any PGE construct, i.e. the blank or control in this experiment.

TABLE 10

Summary of activity tests of PGE mutants expressed in *K. lactis*

| Sample | Day 2 | | | | Day 3 | | | |
|---|---|---|---|---|---|---|---|---|
| | pNP assay (U/ml) | | Plate assay | | pNP assay (U/ml) | | Plate assay | |
| *K. lactis* Transformant | Broth | Supernatant | Broth | Supernatant | Broth | Supernatant | Broth | Supernatant |
| pKLPGE-8 #1 | <0.2 | <0.1 | +/− | − | 0.24 | <0.1 | ++ | − |
| pKLPGE-8 #2 | <0.2 | <0.1 | + | +/− | 0.22 | <0.1 | ++ | +/− |
| pKLPGE-8 #3 | <0.2 | <0.1 | +/− | − | 0.31 | <0.1 | ++ | − |
| pKLPGE-9 #1 | 0.37 | <0.1 | ++ | ++ | 0.71 | 0.15 | +++ | +++ |
| pKLPGE-9 #2 | <0.2 | <0.1 | ++ | + | 0.23 | <0.12 | ++ | ++ |
| pKLPGE-9 #3 | 0.44 | <0.1 | ++ | +/− | 0.98 | 0.15 | +++ | +++ |
| pKLPGE-11 #1 | <0.2 | <0.1 | + | − | 0.28 | <0.1 | + | +/− |
| pKLPGE-11 #2 | 0.27 | <0.1 | + | − | 0.57 | <0.1 | + | +/− |
| pKLPGE-11 #3 | 0.32 | <0.1 | + | − | 0.84 | <0.1 | + | +/− |
| pKLPGE-12 #1 | 1.4 | 0.28 | ++ | + | 1.9 | 0.41 | ++ | + |
| pKLPGE-12 #2 | 4.0 | 0.67 | ++ | + | 6.6 | 1.2 | + | + |
| pKLPGE-12 #3 | 8.0 | 1.6 | ++ | +/− | 13 | 2.8 | ++ | + |
| pKLPGE-10 #1 | <0.2 | <0.1 | − | − | <0.12 | <0.1 | − | − |
| pKLPGE-10 #2 | <0.2 | <0.1 | − | − | <0.12 | <0.1 | − | − |
| pKLPGE-10 #3 | <0.2 | <0.1 | − | − | <0.12 | <0.1 | − | − |
| GG799 | <0.12 | <0.1 | − | − | <0.12 | <0.1 | − | − |

+++, ++, +, +/−, − correspond to large, medium, small, not clear and no halo on the tributyrine plate assay, respectively.

It is concluded that by modification of glycosylation sites and by changing the polarity of the enzyme parts exposed to the surface (determined based on PGE modelling) we could dramatically improve the PGE enzyme expression in *K. lactis*. Furthermore a significant amount of the activity was also found in the supernatant.

Example 5

Screening of the *A. niger* PGE Mutant Transformants

*A. niger* WT 6 was co-transformed with a plasmid carrying the *A. nidulans* amdS selection marker (see FIG. 4) and a plasmid containing the PGE mutant variants (Table 11). The transformants were selected as described above (example 3) only instead of day 5, day 3 supernatant was collected. For all 4 PGE mutants several transformants showed a clear activity halo (data not shown).

For each construct, pANPGE-10, pANPGE-16, pANPGE-12 and pANPGE-13, transformants (1-3) that showed the largest halo on the tributyrine plate assay were examined for lipase activity using pNP-butyrate as a substrate (see above). The summary of various activity assays for the PGE mutants is shown in Table 11. A selected transformant of the wild type PGE, pANPGE-3#2, and the empty strain—WT6 were examined along with the selection of the mutants.

TABLE 11

Summary of activity tests of PGE mutants expressed in *A. niger*

| Sample A. niger transformant | Day 2 pNP-butyrate assay Supernatant | Day 2 Plate assay Supernatant | Day 3 pNP-butyrate assay Supernatant | Day 3 Plate assay Supernatant |
|---|---|---|---|---|
| pANPGE-10#1 | 2.71 | ++++ | 0.72 | ++ |
| pANPGE-16#2 | 7.13 | +++ | 4.61 | ++ |
| pANPGE-16#11 | 1.73 | + | 0.59 | +/− |
| pANPGE-12#33 | 2.44 | + | 1.31 | − |
| pANPGE-12#16 | 6.98 | ++ | 12.2 | + |
| pANPGE-12#15 | 4.78 | ++ | 4.05 | + |
| pANPGE-13#56 | 7.09 | ++++ | 8.4 | ++ |
| pANPGE-13#30 | 5.94 | ++++ | 9.99 | ++ |
| pANPGE-13#07 | 3.7 | ++ | 4.21 | + |
| pANPGE-3#2 | 0.6 | + | 0.12 | − |
| WT6 | 0 | − | 0 | − |

++++, +++, ++, +, +/−, − correspond to very large, large, medium, small, not clear and no halo on the tributyrine plate assay, respectively.

From Table 11 it is clear that all the mutant variants are producing an active enzyme and that the activity is significantly increased compared to the selected multicopy transformant pANPGE-3 #2. The supernatant samples of WT6 and the selected transformants pANPGE-12#16 and pANPGE-13#30 were further analysed on SDS-PAGE gel (Invitrogen) and by western blotting using PGE polyclonal antibodies (see FIG. 9). For the *A. niger* PGE mutant variant no 3 (pANPGE-12), a band corresponding to the mature PGE could be detected on the SDS-PAGE gel. Using the PGE polyclonal antibody PGE, cross-hybridizing bands could be detected in supernatants of both transformants. The highest molecular weight band (about 55 kDa) corresponds probably to the mature PGE mutant and the cross-hybridizing bands of the lower molecular weight could be a result of a proteolytic degradation.

It is concluded that by modification of glycosylation sites and by changing the polarity of the enzyme parts exposed to the surface (determined based on PGE modelling) we could dramatically improve the PGE enzyme expression in *A. niger*. Furthermore high enzymatic activity was also found in the supernatant.

Example 6

Dairy Application—Free Fatty Acid (FFA) Profile Generated by Lipases of Invention in a Cheese-Like System The FFA profile generated by KLPGE-4, KLPGE-9, KLPGE-11, KLPGE-12 (produced in *K. lactis*) and ANPGE-3 (*A. niger*) polypeptides according to the invention and FFA profiles of a microbial lipase (Piccantase® R8000, a microbial lipase from *Rhizomucor miehei* from DSM Food Specialties, The Netherlands) (herewith abbreviated as PicR8000) and animal lipase (Piccantase® C, a animal lipase prepared from calf dried tissues DSM Food Specialties, The Netherlands) (herewith abbreviated as PicC) after incubation with Cheddar cheese paste were compared. The FFA profile of Parmesan cheese as a gold standard is taken from D. T. Lai, A. D. Mackenzie, C. J. O'Connor, K. W. Turner *J. Dairy Sci.* 80:2249-2257 (1997), page 2255 (herewith abbreviated as ParmCh). The FFA profile of Cheddar cheese paste incubated with water instead of lipases was used as a negative control or blank in all experiments and it like the FFA profile of Cheddar cheese that known from literature, M. V. Arbige, P. R. Freund, S. C. Silver, J. T. Zelko, Food Technology 1986, pages 91-98.

The Cheddar cheese paste was prepared from young Cheddar cheese by grating and mixing with water to final moisture content 46.4% w/w (fat content on dry matter was 49.3% w/w). The Cheddar cheese paste was pasteurized for 5 min at +80° C., divided into small portions and stored at +4° C. until the use as a substrate for the lipolytic enzymes in this experiment.

Each of the tested lipases solutions were added to the warm +40° C. portion of Cheddar cheese paste, thoroughly mixed and incubated for 3-4 days at +40° C. The lipases dosages were chosen in order to get the fat conversion ratio of Cheddar cheese paste between 1-25%. In order to stop the lipolytic activity in Cheddar cheese paste, samples were instantly frozen at −20° C. and stored frozen until the analysis.

All samples were analyzed with respect to their FFA profile. Determination of the released FFA in the Cheddar cheese pastes were carried out according to a standard method described in the art (Jong C., de and Badings H. T. *J. High Resolution Chromatography,* 13:84-98 (1990)). In short, after extraction of unreacted fat and FFA from the samples each FFA was isolated by solid-phase extraction method and the isolated FFAs were analyzed by gas chromatography on a capillary column. The peaks on chromatograms were identified by comparison of the retention times with a standard mixture containing the same FFAs. The FFA contents in the various samples were calculated from the peak areas of the individual FFAs using internal standards that were added to the samples (with correction for detector response and extraction yield).

The free fatty acids contents were measured in mg of each free fatty acid per kg fat and further using molecular weight of FFA was recalculated in mmol per kg fat.

As a result, the free fatty acids profiles given in mmol/kg were used for calculation of the percent of fat conversion in each sample in order to control the lipases activity in samples and should be between 1-25% for confident results. The degree of fat conversion was also corrected for background using FFA profile of blank measurement that is Cheddar cheese paste incubated with water.

Therefore, the degree of fat conversion in each sample can be determined as follows and assuming that Cheddar cheese paste contains a total amount of fatty acids of 1.19 mol/kg:

$$D = \frac{(\text{total amount of } FFA \text{ in sample} - \text{amount of } FFA \text{ acids in blank}) * 100\%}{1.19} \quad [1]$$

Using formula [1] the D was calculated for each sample and results are summarised in Table 12.

TABLE 12

Degree of fat conversion

| Lipase | D % |
|---|---|
| KLPGE-4 | 2.3 |
| KLPGE-9 | 2.0 |
| KLPGE-12 | 5.3 |

TABLE 12-continued

| Degree of fat conversion | |
|---|---|
| Lipase | D % |
| KLPGE-11 | 1.4 |
| ANPGE-3 | 3.0 |
| PicC | 4.4 |
| PicR8000 | 11.3 |

As could be seen from Table 12 the D is between 1-25% meaning that enzyme dosages were in proper range.

In order to compare the specificity of lipases to release certain FFA independent to their dosages it is convenient to calculate the relative Cx content of each FFA to total FFA and thus FFA profiles are expressed in mol %. This method of comparison is well known to the person in the art and widely used in literature. Since it was found that FFA profiles of investigated samples do not change significantly between day 1 and day 4 the data only for day 4 are presented in Table 13 and shown in FIG. 7.

The FFA profile of Parmesan Cheese is given as well, see D. T. Lai, A. D. Mackenzie, C. J. O'Connor, K. W. Turner *J. Dairy Sci.* 80:2249-2257 (1997), page 2255

TABLE 13

Relative Cx content in each sample

Relative Cx-content in each sample (expressed in mol %)

| Cx FFA | KLPGE-4 | KLPGE-9 | KLPGE-12 | KLPGE-11 | ANPGE-3 | PicC | PicR8000 | ParmCh |
|---|---|---|---|---|---|---|---|---|
| 4:0 | 35.9 | 42.0 | 28.1 | 28.6 | 40.7 | 45.3 | 12.7 | 39.6 |
| 6:0 | 8.9 | 8.7 | 7.6 | 6.3 | 11.0 | 8.2 | 7.0 | 13.2 |
| 8:0 | 3.0 | 2.5 | 2.5 | 2.1 | 3.4 | 2.2 | 3.8 | 3.7 |
| 10:0 | 6.1 | 5.6 | 5.0 | 5.3 | 5.6 | 5.3 | 5.2 | 6.9 |
| 12:0 | 6.6 | 6.3 | 5.7 | 5.6 | 5.9 | 5.8 | 6.3 | 5.3 |
| 14:0 | 10.1 | 9.6 | 12.3 | 10.1 | 9.4 | 9.5 | 15.4 | 6.7 |
| 16:0 | 14.0 | 13.2 | 18.2 | 16.9 | 13.2 | 12.9 | 24.3 | 11.8 |
| 18:0 | 2.8 | 2.1 | 4.1 | 3.5 | 1.8 | 1.6 | 8.2 | 3.1 |
| 18:1 | 12 | 8.7 | 14.9 | 14.0 | 8.8 | 8.2 | 15.8 | 9 |
| 18:2 | 0.6 | 1.3 | 1.6 | 7.5 | 0.2 | 1.0 | 1.2 | 0.6 |

From Table 13 and FIG. 7 it is clear that FFA profile of Parmesan cheese is different from that generated by microbial lipase PicR8000 which is marketed for production of sharp and piquant varieties of Italian cheeses, such as Provolone, Parmesan, Romano, Technical Bulletin, DSM the Netherlands. It is generally known that microbial lipases are not short C4-C10 FFA specific and a lot of examples including commercial preparations are available in literature. Until now PicR8000 is used as one of the microbial lipases that is able to release short FFA from milk fat.

Surprisingly it was found that lipases according to the KLPGE-4, KLPGE-9, KLPGE-11, KLPGE-12 (produced in *K. lactis*) and ANPGE-3 (produced in *A. niger*) show in comparison with PicR8000 high specificity for the release of C4-free fatty acid. The FFA profile generated by these polypeptides is closer to the FFA profile of Parmesan cheese and FFA profile generated by PicC if compared with that of PicR8000. It is experimentally revealed that lipase of invention are microbially produced: KLPGE-4, KLPGE-9, KLPGE-11, KLPGE-12 (produced in *K. lactis*) and ANPGE-3 (produced in *A. niger*) have close specificity to animal derived lipase PicC to release short C4-C10 FFA and are able to generate FFA profile close to Parmesan cheese.

Specificity of the lipases could be compared using specificity ratio $R_{spec}$ that could be calculated as:

$$R_{spec} = \frac{\sum C4 - C10}{\sum C12 - C18}$$

where $\Sigma C4\text{-}C10$ and $\Sigma C12\text{-}C18$ are sums of relative FFA. The values of the $R_{spec}$ for KLPGE-4, KLPGE-9, KLPGE-11, KLPGE-12 (produced in *K. lactis*), ANPGE-3 (produced in *A. niger*), PicC and PicR8000 are given in Table 14.

TABLE 14

Specificity ratio $R_{spec}$ of lipases KLPGE-4, KLPGE-9, KLPGE-11, KLPGE-12 and ANPGE-3 in comparison with microbial lipase PicR8000, animal lipase PicC and Parmesan cheese.

| | KLPGE-4 | KLPGE-9 | KLPGE-12 | KLPGE-11 | ANPGE-3 | PicC | PicR8000 | ParmCh |
|---|---|---|---|---|---|---|---|---|
| $R_{spec}$ | 1.2 | 1.4 | 0.8 | 0.7 | 1.5 | 1.6 | 0.4 | 1.7 |

As it can be seen the lipases according to the invention KLPGE-4, KLPGE-9, KLPGE-11, KLPGE-12 (produced in *K. lactis*) and ANPGE-3 (produced in *A. niger*) show a high specificity for the release of C4- to C10-free fatty acids that comparable to animal derived lipase PicC and are differ to microbial enzyme Piccantase® R8000 which is less specific.

Example 7

Dairy Application—Use of Calf Pregastric Esterase (Piccantase C3x) and KLPGE-9 in Cheddar Manufacturing and Organoleptic Assessment of Produced Cheddar Cheeses Cheddar cheese was manufactured using a generic UK style recipe. After pasteurisation (15 seconds at 73° C.), the milk was inoculated using DSM DelvoTEC MT53A starter culture (1.5 units per 1000 L cheese milk). The milk was allowed to pre ripen for 45 minutes. The enzymes tested were added 15 minutes prior to the rennet. Table 15 lists the quantities of enzymes used.

TABLE 15

Level of addition of the lipase enzymes to cheese milk

| Cheese vat | Dosage levels enzyme preparation |
|---|---|
| 1 | Piccantase C3, 20 g per 175 L cheese milk |
| 2 | KLPGE-9, 20 g per 175 L cheese milk |
| 3 | KLPGE-9, 60 g per 175 L cheese milk |

Piccantase C3 = Calf pregastric esterase (batch 90629C3) containing 21.0 U/g activity (pNP-butyrate assay)
PGE9 = Ultra-filtrate fraction VIJ.922.04 containing 42.2 U/g activity (pNP-butyrate assay)

Maxiren 600 was used as rennet (52.5 IMCU per 1 L cheese milk). After approximately 30 minutes, the coagulum was firm enough to be cut. Cooking commenced after 10 minutes to a temperature of 38° C. Regular pH checks were made and when the pH had dropped below 6.2, the whey was drained off and the cheddaring part of the manufacturing process started. The curd slabs were turned at regular intervals and when the pH reached 5.3, the slabs were milled and salted. The milled, salted curd was allowed to mellow for approximately 15 minutes after which the curd was moulded and pressed overnight. The following morning the cheeses were removed from the moulds, vacuum packed and ripened at 11° C. The composition of the cheeses was determined on post press samples and organoleptic assessment took place after 4, 8 and 16 weeks of ripening. Table 16 lists the gross composition of the cheeses.

TABLE 16

Composition of post press Cheddar samples.

| Cheese | Salt % | Fat % | pH | Moisture % |
|---|---|---|---|---|
| Piccantase C3 | 1.7 | 31.0 | 5.40 | 36.8 |
| KLPGE-9, 20 g/175 L | 1.7 | 31.4 | 5.40 | 36.5 |
| KLPGE-9, 60 g/175 L | 1.7 | 31.2 | 5.38 | 36.3 |

The cheeses were organoleptically assessed after 4, 8 and 16 weeks of ripening by an external panel (Table 17). All intensity values were obtained by a Fizz sensory data acquisition system, using unstructured line scales The sensory data X were preprocessed to $\tilde{X}$ in order to correct for individual use of scale according the following formula $$\tilde{X}_{ijkl} = \frac{X_{ijkl} - \overline{X}_{i\ldots}}{\overline{S}_{i\ldots}} \cdot \sqrt[I]{\prod_{v=1}^{I} \overline{S}_{v\ldots}} + \frac{1}{I}\sum_{v=1}^{I} \overline{X}_{v\ldots}$$

where i=1, . . . , I assessors, j=1, . . . , J products, k=1, . . . , K replicates, l=1, . . . , L attributes.

With individual difference scaling it is assumed that each assessor uses the line scales differently, regardless of the attribute used. Hence, assessors who use a small part of the scale and on different positions are scaled to the same level as assessors who use large part of the scale on different positions. The data were modelled by means of variance components estimated by restricted maximum likelihood (REML) using the products as fixed effects and the panellist and product×panellist interactions as random effects. The advantage of these REML-models is that data are modelled in agreement with the known structure of the data (i.e. product dependent variability of assessors, session and round effects can explicitly be modelled enabling better estimates of the true product variability, which is our main interest.

The letters (for example A or B) as used in Table 17 show the significant differences.

TABLE 17

Results of the organoleptic assessment of 4, 8 and 16 weeks ripened cheddar made with different enzyme preparations.

| | Week 4 assessment (N = 12) | | | | Week 8 assessment (N = 8) | | | | Week 16 assessment (N = 12) | | | |
|---|---|---|---|---|---|---|---|---|---|---|---|---|
| | PiccC3 | KLPGE9 20 g | KLPGE9 60 g | p-Value | PiccC3 | KLPGE9 20 g | KLPGE9 60 g | p-Value | PiccC3 | KLPGE9 20 g | KLPGE9 60 g | p-Value |
| Flavor attribute | | | | | | | | | | | | |
| Intensity | 40.1 | 34.3 | 40.8 | 0.0948 | 43.6 | 37.6 | 41.4 | 0.2159 | 48.1 | 45.3 | 47.8 | 0.1626 |
| Salt | 26.5 | 29.0 | 28.4 | 0.2318 | 23.8 | 23.3 | 22.4 | 0.8785 | 33.3 | 32.3 | 32.8 | 0.8920 |
| Sour | 29.7 | 26.6 | 30.0 | 0.2161 | 25.1 | 20.4 | 24.9 | 0.0785 | 36.3 | 36.8 | 37.0 | 0.9151 |
| Sweet | 16.8 | 15.7 | 15.3 | 0.5787 | 18.6 | 18.6 | 18.3 | 0.9807 | 20.0 | 19.3 | 20.3 | 0.7959 |
| Dairy | 16.4 | 15.5 | 16.1 | 0.8600 | 12.6 | 12.4 | 12.8 | 0.9347 | 17.8 | 18.5 | 18.3 | 0.8464 |
| Butter | 13.4 | 13.9 | 13.0 | 0.8458 | 11.9 | 12.7 | 12.9 | 0.4958 | 13.9 | 15.8 | 14.8 | 0.4281 |
| Savory | 15.8 | 15.3 | 16.3 | 0.6919 | 13.8 | 12.3 | 13.4 | 0.4046 | 20.4 | 21.8 | 20.9 | 0.5909 |
| Farmer | 16.8 | 16.0 | 16.2 | 0.9654 | 20.8 (AB) | 19.1 (B) | 28.6 (A) | * | 20.1 | 17.2 | 20.1 | 0.2843 |
| Fruity | 8.5 | 8.5 | 8.8 | 0.7893 | 7.3 | 7.4 | 8.2 | 0.1623 | 10.2 | 10.8 | 9.7 | 0.7725 |
| Nutty | 11.5 | 11.0 | 11.8 | 0.7998 | 7.9 | 7.9 | 8.8 | 0.3346 | 15.4 | 14.0 | 13.1 | 0.1426 |
| Mouth feel attribute | | | | | | | | | | | | |
| Rubbery | 44.2 | 42.0 | 41.0 | 0.4707 | 30.9 | 30.8 | 30.3 | 0.9804 | 32.5 | 30.2 | 30.4 | 0.7163 |
| Hardness | 42.9 | 41.4 | 43.9 | 0.2413 | 38.4 | 39.6 | 38.8 | 0.6519 | 34.7 | 34.1 | 36.0 | 0.4653 |
| Stickiness | 13.5 | 14.4 | 14.6 | 0.5969 | 15.3 | 15.6 | 15.6 | 0.9618 | 30.0 | 30.2 | 28.8 | 0.6222 |

TABLE 17-continued

Results of the organoleptic assessment of 4, 8 and 16 weeks ripened cheddar made with different enzyme preparations.

| | Week 4 assessment (N = 12) | | | | Week 8 assessment (N = 8) | | | | Week 16 assessment (N = 12) | | | |
|---|---|---|---|---|---|---|---|---|---|---|---|---|
| | PiccC3 | KLPGE9 20 g | KLPGE9 60 g | p-Value | PiccC3 | KLPGE9 20 g | KLPGE9 60 g | p-Value | PiccC3 | KLPGE9 20 g | KLPGE9 60 g | p-Value |
| Grainy | 41.8 | 39.8 | 40.9 | 0.6572 | 29.4 | 32.1 | 31.4 | 0.6370 | 27.1 (A) | 22.8 (B) | 27.0 (A) | * |
| Mealy/dry | 29.0 | 25.7 | 28.0 | 0.2663 | 20.4 | 23.4 | 20.0 | 0.2977 | 17.8 | 17.0 | 19.0 | 0.5623 |
| Crystals | 4.3 | 4.6 | 4.2 | 0.1123 | 4.4 | 4.7 | 4.4 | 0.5730 | 5.0 | 5.3 | 5.5 | 0.0812 |
| Fatty | 12.5 | 14.0 | 14.4 | 0.3252 | 10.1 | 11.1 | 8.2 | 0.1888 | 16.5 | 17.7 | 16.8 | 0.7635 |
| Aftertaste attribute | | | | | | | | | | | | |
| Intensity | 37.5 (A)A | 26.6 (B) | 32.5 (A) | ** | 37.4 | 32.6 | 36.4 | 0.0706 | 45.0 (A) | 37.6 (B) | 43.6 (A) | ** |
| Sweet | 16.6 | 14.9 | 14.6 | 0.3542 | 17.8 | 17.7 | 17.6 | 0.9902 | 18.1 | 17.3 | 19.7 | 0.1360 |
| Bitter | 22.1 (A) | 17.3 (B) | 22.0 (A) | ** | 23.1 | 22.0 | 24.6 | 0.1543 | 32.6 | 31.3 | 33.3 | 0.6660 |
| Soapy | 34.7 (A) | 16.2 (B) | 29.5 (A) | *** | 38.1 (A) | 20.8 (B) | 35.3 (A) | ** | 44.3 (A) | 23.7 (B) | 36.8 (A) | *** |
| Length | 37.4 (A) | 26.1 (B) | 33.9 (A) | *** | 40.2 (A) | 31.8 (B) | 37.3 (A) | ** | 45.8 (A) | 36.9 (B) | 43.8 (A) | *** |

* significant at 5%
** significant at 1%
*** significant at 0.1%

It was concluded from the REML analysis data and the scored organoleptic attributes that the tested KLPGE-9 did match the applied calf pregastric esterase (Piccantase C3) fully in all attributes examined. No significant differences in scored attributes and performance in the tested Cheddar cheeses (from an organoleptic point of view) were found comparing the highest dosage of KLPGE-9 and the calf derived Piccantase C. The lower dosage KLPGE-9 did score for several attributes lower, as expected.

Example 8

Dairy Application—Use of Calf Pregastric Esterase (Piccantase C3x), KLPGE-9 and KLPGE-12 in Enzyme Modified Cheese (EMC) and Organoleptic Assessment of the Resulting EMC Cheddar cheese based EMC was made using a generic recipe with a composition as described in table 18. Mild cheddar was shredded and the listed components were added in mentioned order while mixing the cheese slurry at ambient temperature. The cheese slurry was slowly heated to 72° C. while constantly mixing. The cheese slurry was kept at 72° C. for approximately 10 min until a smooth cheese paste was obtained. The paste was cooled to 50° C. and divided in smaller fractions. Each different fraction was used for incubation with a different enzyme preparation (table 19). After addition of the enzyme preparation, the cheese slurry was mixed thoroughly and incubated for 40 hours at 40° C. After the incubation the obtained EMC samples were heated for 20 minutes at 72° C., subsequently cooled to ambient temperature and stored frozen in closed, clean and sterile containers (<−20° C.) until further use. The EMC samples were analysed for FFA composition (table 20; FIG. 10) and used for organoleptic assessment by an external descriptive panel.

TABLE 18

Composition of cheese base used for EMC preparation

| Ingredient description | Weight (g) | Composition (%) |
|---|---|---|
| Mild Cheddar | 1000 | 79.6% |
| Potable water | 180 | 14.3% |
| Sodiumchloride | 33 | 2.63% |
| Tri-sodiumcitrate | 41 | 3.26% |
| Potassiumsorbate | 2.7 | 0.21% |
| total | 1257 | 100% |

TABLE 19

Enzyme dosages used for EMC preparation

| Lipase description | Activity (U/g) | Dosage in EMC (% w/w) |
|---|---|---|
| Piccantase C3 (batch 80815C3) | 18.4 | 3.0 |
| KLPGE-9 (batch VIJ.922.04) | 42.2 | 1.5 |
| KLPGE-12 (batch VIJ.922.14) | 1980 | 1.5 |

TABLE 20

Free fatty acid composition of enzyme treated EMC preparations

| Sample description | Concentrations free fatty acid in mmol/kg EMC[#] | | | | | | | | | | |
|---|---|---|---|---|---|---|---|---|---|---|---|
| | C4:0 | C6:0 | C8:0 | C10:0 | C12:0 | C14:0 | C16:0 | C18:0 | C18:1 | C18:2 | sum |
| Piccantase C3 3.0% | 56.6 | 14.7 | 4.7 | 7.1 | 7.4 | 10.8 | 11.7 | 1.7 | 9.9 | 0.5 | 125.0 |
| KLPGE-9 1.5% | 28.8 | 7.1 | 2.5 | 4.1 | 4.5 | 6.5 | 7.5 | 0.9 | 6.3 | 0.5 | 68.6 |
| KLPGE-12 1.5% | 43.0 | 13.9 | 7.5 | 9.9 | 10.9 | 26.2 | 44.3 | 9.3 | 33.6 | 1.6 | 200.3 |

[#]Values corrected for free fatty acids concentrations in non-lipase treated EMC base To assure that the panellist were offered samples for organoleptic assessment containing equal amounts of total FFA, the prepared EMC's were diluted in a white sauce/paste made of 12% maize (corn) starch in pasteurized milk (1% fat). The final EMC mixture after dilution in the white sauce/paste for organoleptic judgement did contain an amount of EMC representing for each mixture 14-16 mmol total FA per kg white sauce/EMC mixture.

The samples of EMC diluted in white sauce were organoleptically assessed (at ambient temperature) within 2 hours after preparation of the samples by an external descriptive panel (table 4). All intensity values were obtained by a Fizz sensory data acquisition system, using unstructured line scales (N=13).

The sensory data X were preprocessed to $\tilde{X}$ in order to correct for individual use of scale according the following formula $$\tilde{X}_{ijkl} = \frac{X_{ijkl} - \overline{X}_{i...}}{\overline{S}_{i...}} \cdot \sqrt{\prod_{v=1}^{I} \overline{S}_{v...} + \frac{1}{I}\sum_{v=1}^{I} \overline{X}_{v...}}$$

where i=1, ..., I assessors, j=1, ..., J products, k=1, ..., K replicates, l=1, ..., L attributes.

With individual difference scaling it is assumed that each assessor uses the line scales differently, regardless of the attribute used. Hence, assessors who use a small part of the scale and on different positions are scaled to the same level as assessors who use large part of the scale on different positions. The data were modelled by means of variance components estimated by restricted maximum likelihood (REML) using the products as fixed effects and the panellist and product×panellist interactions as random effects. The advantage of these REML-models is that data are modelled in agreement with the known structure of the data (i.e. product dependent variability of assessors, session and round effects can explicitly be modelled enabling better estimates of the true product variability, which is our main interest.

TABLE 21

Results of the organoleptic assessment of the different enzyme treated EMC's (each mixture diluted to comparable FFA level in white sauce/paste)

| | KLPGE-12 | KLPGE-9 | Piccantase C3 | p-value |
|---|---|---|---|---|
| Odour attributes | | | | |
| Intensity | 42.3 | 45.3 | 45.5 | 1.0 |
| Prickling | 29.7 | 34.6 | 34.2 | 0.486 |
| Sour | 34.7 | 35.1 | 33.1 | 1.0 |
| Flavour attributes | | | | |
| Intensity | 49.4 | 50.7 | 44.7 | 0.050 |
| Salt | 25.1 (C) | 39.0 (A) | 31.9 (B) | *** |
| Sweet | 32.5 | 30.0 | 33.6 | 0.895 |
| Dairy | 31.8 | 30.4 | 31.4 | 1.0 |
| Savoury | 17.7 (B) | 25.7 (A) | 22.8 (AB) | ** |
| Farmer | 24.2 (B) | 32.2 (A) | 27.8 (AB) | * |
| Fruity | 9.7 | 11.0 | 11.7 | 0.867 |
| Aftertaste attributes | | | | |
| Intensity | 47.0 | 43.0 | 42.5 | 0.623 |
| Farmer | 22.8 | 26.0 | 24.8 | 1.0 |
| Bitter | 31.4 (A) | 26.5 (AB) | 23.8 (B) | * |
| Soapy | 47.3 | 41.0 | 38.0 | 0.200 |
| Length | 51.0 | 46.9 | 44.8 | 0.325 |

\* significant at 5% (p < 0.05)
\*\* significant at 1% (p < 0.01)
\*\*\* significant at 0.1% (p < 0.001)

It was concluded that (like the earlier described manufactured cheddar cheese) the EMC made with KLPGE-9 did match in all attributes completely with the EMC made with Piccantase C3. There was a difference scored in saltiness, but this could be totally contributed to the different dilutions applied to equalize and match the total FFA in the final EMC mixtures offered for tasting.

It was further concluded that EMC made with KLPGE-12 did match both the EMC's made with KLPGE-9 and Piccantase C3 very close and was scored almost identical. Piccantase C3 and KLPGE-12 were fully grouped for all the examined attributes except saltiness and bitter attribute. Lower salt in KLPGE-12 can be contributed to the higher dilution applied, as explained before. The bitter attribute is both scored for KLPGE-9 and KLPGE-12 (however limited, significant at only p<0.05) and is to be most likely contributed to the formulation of both enzyme preparation.

Example 9

Dairy Application—Use of ANPGE-12 and ANPGE-13 in Enzyme Modified Cheese (EMC) to Determine FFA Profile Cheddar cheese based EMC was made using a generic recipe with a composition as described in table 22. Mild/Young and mature cheddar was shredded and the listed components were added in mentioned order while mixing the cheese slurry at ambient temperature. The cheese slurry was slowly heated to 72° C. while constantly mixing. The cheese slurry was kept at 72° C. for approx. 10 min until a smooth cheese paste was obtained. The paste was cooled to 50° C. and divided in smaller fractions. Each different fraction was used for incubation with a different enzyme preparation (table 23). After addition of the enzyme preparation, the cheese slurry was mixed thoroughly and incubated for 72 hours at 40° C. After the incubation the obtained EMC samples were cooled to ambient temperature and stored frozen in closed, clean and sterile containers (<−20° C.) until further use. The EMC samples were analysed for FFA composition (table 24; FIG. 11).

TABLE 22

Composition of cheese base used for EMC preparation

| Ingredient description | Weight (g) | Composition (%) |
|---|---|---|
| Mild/Young Cheddar | 775.5 | 51.7% |
| Mature Cheddar | 104.4 | 7.0% |
| Potable water | 501 | 33.4% |
| Anhydrous fat | 89.4 | 6.0% |
| sodiumchloride | 3.0 | 0.20% |
| di-sodiumphosphate | 12.6 | 0.84% |
| tri-sodiumphosphate | 6.6 | 0.44% |
| tri-sodiumcitrate | 7.8 | 0.52% |
| total | 1500 | 100% |

TABLE 23

Enzyme dosages used for EMC preparation

| Lipase description | Activity (U/g) | Dosage in EMC (% w/w) |
|---|---|---|
| KLPGE-12 (batch PGE.GRZ.1004) | 600 | 3.3% |
| ANPGE-12, supernatant day 4 | 15.4 | 15% |
| ANPGE-13, supernatant day 4 | 8.8 | 15% |

TABLE 24

Free fatty acid composition of lipase treated EMC preparations

| Sample description | Concentrations free fatty acid in mmol/kg EMC[#] | | | | | | | | | | |
|---|---|---|---|---|---|---|---|---|---|---|---|
| | C4:0 | C6:0 | C8:0 | C10:0 | C12:0 | C14:0 | C16:0 | C18:0 | C18:1 | C18:2 | sum |
| KL-PGE12 (batch PGE.GRZ.1004) | 57.2 | 20.3 | 7.7 | 14.1 | 13.9 | 35.9 | 70.9 | 19.1 | 42.3 | 7.4 | 288.8 |
| ANPGE-12, supernatant day 4 | 53.2 | 14.7 | 4.9 | 9.6 | 9.6 | 24.2 | 44.1 | 9.7 | 25.7 | 3.9 | 199.6 |
| ANPGE-13, supernatant day 4 | 58.6 | 19.1 | 6.8 | 14.4 | 12.8 | 29.4 | 51.8 | 11.9 | 34.3 | 5.2 | 244.2 |

[#]Values corrected for free fatty acids concentrations in non-lipase treated EMC base It was concluded that both *A. niger* enzyme preparations were capable of releasing a fair amount of free fatty acids compared to the used KLPGE-12 preparation and the mol ratio of all three enzyme preparations tested were considered identical.

Example 10

Releasing CPO PGE from Host Cell

Strain *K. lactis* expressing the KLPGE-3 protein was fermented on a lab scale basis. The end of fermentation sample was adjusted to pH 10 with help of 4N NaOH.

FIG. 6 provides a typically curve obtained for *K. lactis* broth which at the end of fermentation was adjusted to pH 10 and incubated at 4 degrees Celsius.

The y-axis represents the ratio supernatant/broth. The supernatant was obtained by centrifugation (10 minutes, 4000 rpm).

The activities were measured with the pNP-butyrate assay.

Example 11

Killing of Host Cells 7.1 *K. lactis* Transformant DKLPGE-12 #3

Killing started at the end of fermentation at 116 hours by adjusting the pH to 10. After 48 hours, 10 µl broth was plated undiluted on a PDA plate and incubated for 5 days at 30 degrees Celsius. After 5 days there was no growth. The plate was left at 30 degrees Celsius for another couple of days and again checked, still no growth was observed. It is concluded that the pH treatment resulting in killing of the cells.

7.2. *K. lactis* Transformants pKLPGE-9 #1 and #3 and *K. lactis* Transformant pKLPGE-11 #3

Killing started at the end of fermentation at 118 h by adjusting the pH to 10 and incubating at 15 degrees Celsius. After incubation samples were taken, plated on PDA, and incubated for 7 days at 30 degrees. None of the plates showed growth.

Example 12

Combinations of Functional Equivalents

The specification provides multiple examples of functional equivalents/mutants/alternatives.

It is clear for the skilled person that the separate mutations can also be combined. One can for example combine a hydrophilicity mutant with a glycosylation mutant.

The invention claimed is:

1. A recombinant polypeptide having lipolytic activity comprising: an amino acid sequence, which is at least 80% homologous to the amino acid sequence of SEQ ID NO: 2, wherein the amino acid sequence of the recombinant polypeptide comprises, when compared to SEQ ID NO: 2, amino acid substitutions of A70S, K98N, R158N, R159K, H318N, P320S, and I361T.

2. The isolated polypeptide of claim 1, which is SEQ ID NO:7.

3. A composition comprising the polypeptide of claim 1 and an acceptable carrier or preservative.

4. A composition comprising the polypeptide of claim 1 as a lipolytic enzyme, and a second enzyme.

5. The composition of claim 4, wherein said second enzyme comprises an aspartic protease or a phospholipase.

6. The isolated polypeptide of claim 1, having lipolytic activity comprising an amino acid sequence, which is at least 80% homologous to amino acids 20-397 of the amino acid sequence according to SEQ ID NO:2.

7. A recombinant host cell comprising the polypeptide of claim 1.

8. A method for manufacturing a polypeptide having lipolytic activity comprising cultivating the recombinant host cell of claim 7 under conditions which allow for expression of the polypeptide and optionally recovering the polypeptide from the cell or culture medium.

9. The recombinant host cell of claim 7, which has part of the polypeptide attached to its outer cell membrane or cell wall.

10. A method for releasing a polypeptide bound to the exterior of the recombinant host cell of claim 9, comprising contacting said host cell with an aqueous solution having a pH of approximately 9-12 and allowing the obtained solution to incubate for at least 2 hours at a temperature of between from 4 and 30 degrees Celsius.

11. The method of claim 10 further comprising maintaining the pH at a constant value.

12. A method for preparing a dairy product comprising adding the recombinant polypeptide of claim 1 to a dairy composition used in the production of a dairy product under conditions sufficient for the enzyme catalyze the hydrolysis of fat.

13. The method of claim 12 wherein the ΣRelative C4-C10 content/ΣRelative C12-C18 content is at least 0.7, wherein "ΣRelative C4-C10 content" is the sum of the relative content of C4-, C6-, C8- and C10-free fatty acids present in the composition which has been treated with a polypeptide having lipolytic activity and wherein "ΣRelative C12-C18 content" is the sum of the relative content of C12-, C14-, C16- and C18-free fatty acids present in the composition which has been treated with a polypeptide having lipolytic activity.

* * * * *

SEQUENCE LISTING

```
<160> NUMBER OF SEQ ID NOS: 23

<210> SEQ ID NO 1
<211> LENGTH: 1137
<212> TYPE: DNA
<213> ORGANISM: Artificial Sequence
<220> FEATURE:
<223> OTHER INFORMATION: cDNA codon-pair optimized (CPO) pregasteric
      esterase (PGE) for K.lactis; processed, i.e. without signal
      sequence coding part

<400> SEQUENCE: 1
ttcttaggta agatcgctaa gaacccagaa gcctctatga acgtttccca aatgatttct      60
tactggggtt acccatctga aatgcacaag gtcattaccg ctgacggtta catttttgcaa    120 gtttaccgta tcccacacgg taagaacaac gctaaccatt tgggtcaaag accagttgtc    180
tttttgcaac acggtttatt gggttccgct actaactgga tctccaattt gccaaagaac    240
tctctaggtt tcttgttggc tgatgctggt tacgatgtct ggttaggtaa ctctagaggt    300
aacacctggg ctcaagaaca cttgtactac tctccagact ccccagaatt ctgggctttc    360
tccttcgacg aaatggctga atacgactta ccatctacta tcgacttcat tttgagaaga    420
actggtcaaa agaaattgca ttacgttggt cactcccaag gtactactat cggtttcatt    480
gccttctcca cctccccaac cttggctgaa aagatcaagg tcttctacgc tttagcccca    540
```

```
gttgctactg ttaagtacac caaatctttg ttcaacaaat tggctttgat cccacacttc    600
ttgttcaaga ttatctttgg tgacaagatg ttctatccac acaccttttt ggaacaattc    660
ttgggtgtcg aaatgtgttc tagagaaacc ttggatgtct tgtgtaagaa cgctttattc    720
gctatcactg tgttgacaa caagaacttt aacatgtcta gattggatgt ttacattgcc    780
cacaacccag ccggtacctc cgtccaaaac accttgcact ggagacaagc tgttaagtct    840
ggtaagttcc aagccttcga ctggggtgcc cataccaaa acttgatgca ctaccaccaa    900
ccaactcctc caatttacaa tttgaccgct atgaacgttc aattgccgt ctggtccgct    960 gataacgatt tgctagctga ccctcaagat gtcgacttct tgttgtctaa gttgtctaac   1020
ttgatctacc acaaggaaat cccaaactac aaccatttgg atttcatctg ggctatggac   1080
gctccacaag aagtttacaa cgaaatcgtc tctttgatgg ctgaagacaa gaaataa     1137
```

<210> SEQ ID NO 2
<211> LENGTH: 397
<212> TYPE: PRT
<213> ORGANISM: Artificial Sequence
<220> FEATURE:
<223> OTHER INFORMATION: protein PGE wt with the signal sequence as well
      as CPO PGE; the amino acids 1-19 represent the signal sequence and
      the amino acids 20-397 represent mature PGE

<400> SEQUENCE: 2

```
Met Trp Trp Leu Leu Val Thr Val Cys Phe Ile His Met Ser Gly Asn
1               5                   10                  15

Ala Phe Cys Phe Leu Gly Lys Ile Ala Lys Asn Pro Glu Ala Ser Met
            20                  25                  30

Asn Val Ser Gln Met Ile Ser Tyr Trp Gly Tyr Pro Ser Glu Met His
        35                  40                  45

Lys Val Ile Thr Ala Asp Gly Tyr Ile Leu Gln Val Tyr Arg Ile Pro
    50                  55                  60

His Gly Lys Asn Asn Ala Asn His Leu Gly Gln Arg Pro Val Val Phe
65                  70                  75                  80

Leu Gln His Gly Leu Leu Gly Ser Ala Thr Asn Trp Ile Ser Asn Leu
                85                  90                  95

Pro Lys Asn Ser Leu Gly Phe Leu Leu Ala Asp Ala Gly Tyr Asp Val
            100                 105                 110

Trp Leu Gly Asn Ser Arg Gly Asn Thr Trp Ala Gln Glu His Leu Tyr
        115                 120                 125

Tyr Ser Pro Asp Ser Pro Glu Phe Trp Ala Phe Ser Phe Asp Glu Met
    130                 135                 140

Ala Glu Tyr Asp Leu Pro Ser Thr Ile Asp Phe Ile Leu Arg Arg Thr
145                 150                 155                 160

Gly Gln Lys Lys Leu His Tyr Val Gly His Ser Gln Gly Thr Thr Ile
                165                 170                 175

Gly Phe Ile Ala Phe Ser Thr Ser Pro Thr Leu Ala Glu Lys Ile Lys
            180                 185                 190

Val Phe Tyr Ala Leu Ala Pro Val Ala Thr Val Lys Tyr Thr Lys Ser
        195                 200                 205

Leu Phe Asn Lys Leu Ala Leu Ile Pro His Phe Phe Lys Ile Ile
    210                 215                 220

Phe Gly Asp Lys Met Phe Tyr Pro His Thr Phe Leu Glu Gln Phe Leu
225                 230                 235                 240

Gly Val Glu Met Cys Ser Arg Glu Thr Leu Asp Val Leu Cys Lys Asn
```

```
                        245                 250                 255
Ala Leu Phe Ala Ile Thr Gly Val Asp Asn Lys Asn Phe Asn Met Ser
            260                 265                 270

Arg Leu Asp Val Tyr Ile Ala His Asn Pro Ala Gly Thr Ser Val Gln
        275                 280                 285

Asn Thr Leu His Trp Arg Gln Ala Val Lys Ser Gly Lys Phe Gln Ala
    290                 295                 300

Phe Asp Trp Gly Ala Pro Tyr Gln Asn Leu Met His Tyr His Gln Pro
305                 310                 315                 320

Thr Pro Pro Ile Tyr Asn Leu Thr Ala Met Asn Val Pro Ile Ala Val
                325                 330                 335

Trp Ser Ala Asp Asn Asp Leu Leu Ala Asp Pro Gln Asp Val Asp Phe
            340                 345                 350

Leu Leu Ser Lys Leu Ser Asn Leu Ile Tyr His Lys Glu Ile Pro Asn
        355                 360                 365

Tyr Asn His Leu Asp Phe Ile Trp Ala Met Asp Ala Pro Gln Glu Val
    370                 375                 380

Tyr Asn Glu Ile Val Ser Leu Met Ala Glu Asp Lys Lys
385                 390                 395
```

<210> SEQ ID NO 3
<211> LENGTH: 1137
<212> TYPE: DNA
<213> ORGANISM: Bos taurus
<220> FEATURE:
<221> NAME/KEY: misc_feature
<222> LOCATION: (1)..(1137)
<223> OTHER INFORMATION: wild type PGE

<400> SEQUENCE: 3

| | | | | | | |
|---|---|---|---|---|---|---|
| ttccttggaa | aaattgctaa | gaaccctgaa | gccagtatga | atgttagtca | gatgatttcc | 60 |
| tactggggct | acccaagtga | gatgcataaa | gttataactg | cggatggtta | tatccttcag | 120 |
| gtctatcgga | ttcctcatgg | aaagaataat | gctaatcatt | taggtcagag | acctgttgtg | 180 |
| tttctgcagc | atggtcttct | tggatcagcc | acaaactgga | tttccaacct | gcccaagaac | 240 |
| agcctgggct | tcctcctggc | agatgctggt | tatgacgtgt | ggctggggaa | cagcagagga | 300 |
| aacacctggg | cccaggaaca | tttatactat | tcaccagact | ccccggaatt | ctgggctttc | 360 |
| agctttgatg | aaatggcgga | atatgacctt | ccatctacaa | ttgatttcat | cttaaggaga | 420 |
| acaggacaga | agaagctaca | ctatgttggc | cattcccaag | gcaccaccat | tggttttatc | 480 |
| gcctttctcta | ccagtcccac | attggctgaa | aaaatcaaag | tcttctatgc | attagcccca | 540 |
| gttgccacag | tgaagtacac | caagagcctg | tttaacaaac | ttgcacttat | tcctcacttc | 600 |
| ctcttcaaga | ttatatttgg | tgacaaaatg | ttctacccac | acactttttt | ggaacaattt | 660 |
| cttggtgttg | aaatgtgctc | ccgtgagaca | ctggatgtcc | tttgtaagaa | tgccttgttt | 720 |
| gccattactg | gagttgacaa | taaaaacttc | aacatgagtc | gcttagatgt | gtatatagca | 780 |
| cataatccag | caggaacttc | tgttcaaaac | accctccact | ggagacaggc | tgttaagtct | 840 |
| gggaaattcc | aagcttttga | ctggggagcc | ccatatcaga | acctaatgca | ttatcatcag | 900 |
| cccacacctc | ccatctacaa | tttaacagcc | atgaatgtcc | caattgcagt | atggagtgct | 960 |
| gacaatgacc | tgttggctga | ccctcaggat | gttgactttc | tgctttcaaa | actctctaat | 1020 |
| ctcatttacc | acaaggaaat | tccaaattac | aatcacttgg | actttatctg | ggcaatggat | 1080 |
| gcacctcaag | aagtttacaa | tgaaattgtt | tctttgatgg | ccgaagacaa | aaagtag | 1137 |

<210> SEQ ID NO 4
<211> LENGTH: 1137
<212> TYPE: DNA
<213> ORGANISM: Artificial Sequence
<220> FEATURE:
<223> OTHER INFORMATION: cDNA mutant 1 (excluding signal sequence)

<400> SEQUENCE: 4

```
tttttgggta agattgccaa gaacccagaa gcctccatga acgtttctca aatgatctct      60
tactggggtt acccatctga aatgcacaag gttatcactg ctgacggtta catcttacaa     120
gtctacagaa tcccacacgg taagaacaat gctaaccatt tgggtcaaag accagttgtt     180
ttcttgcaac atggtctatt aggttctgcc accaactgga tctccaactt gccaaacaac     240
tctttgggtt tcttgttggc tgatgctggt tacgatgtct ggttaggtaa ctccagaggt     300
aacacctggg ctcaagaaca cttgtactac tctccagatt ctccagaatt ctgggctttc     360
tctttcgacg aaatggctga atacgacttg ccatctacca ttgacttcat cttgagaaga     420
accggtcaaa agaaattgca ctcgttggt cactctcaag gtaccaccat ggtttcatt      480
gctttctcca cttctccaac tttggctgaa aagatcaagg ttttctacgc tttggctcca     540
gttgccaccg tcaagtacac caaatcttta ttcaacaaat tggctttgat tccacacttc     600
ttattcaaga tcatcttcgg tgacaagatg ttctatcctc acactttctt ggaacaattc     660
ttgggtgttg aaatgtgttc cagagaaact ttggatgtct tgtgtaagaa cgctttgttt     720
gccatcactg gtgttgacaa caagaacttc aacatgtccc gtttggatgt ctacattgct     780
cacaacccag ctggtacttc cgttcaaaac actttgcact ggagacaagc tgtcaaatct     840
ggtaagttcc aagcctttga ctggggtgct ccataccaaa acttgatgca ctaccaccaa     900
ccaaccccac caatctacaa cttgactgcc atgaacgttc caattgctgt ctggtccgct     960
gacaacgatt tgttggctga ccctcaagat gtcgacttct gctatccaa gttgtccaac    1020
ttgatctacc acaaggaaat tccaaactac aaccatttgg atttcatctg gctatggac    1080
gctccacaag aagtctacaa cgaaattgtc tctttgatgg ctgaagacaa gaagtaa      1137
```

<210> SEQ ID NO 5
<211> LENGTH: 378
<212> TYPE: PRT
<213> ORGANISM: Artificial Sequence
<220> FEATURE:
<223> OTHER INFORMATION: protein mutant 1 (lacking signal sequence)

<400> SEQUENCE: 5

```
Phe Leu Gly Lys Ile Ala Lys Asn Pro Glu Ala Ser Met Asn Val Ser
1               5                   10                  15

Gln Met Ile Ser Tyr Trp Gly Tyr Pro Ser Glu Met His Lys Val Ile
            20                  25                  30

Thr Ala Asp Gly Tyr Ile Leu Gln Val Tyr Arg Ile Pro His Gly Lys
        35                  40                  45

Asn Asn Ala Asn His Leu Gly Gln Arg Pro Val Val Phe Leu Gln His
    50                  55                  60

Gly Leu Leu Gly Ser Ala Thr Asn Trp Ile Ser Asn Leu Pro Asn Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ala Gln Glu His Leu Tyr Tyr Ser Pro
            100                 105                 110
```

Asp Ser Pro Glu Phe Trp Ala Phe Ser Phe Asp Glu Met Ala Glu Tyr
        115                 120                 125

Asp Leu Pro Ser Thr Ile Asp Phe Ile Leu Arg Arg Thr Gly Gln Lys
130                 135                 140

Lys Leu His Tyr Val Gly His Ser Gln Gly Thr Thr Ile Gly Phe Ile
145                 150                 155                 160

Ala Phe Ser Thr Ser Pro Thr Leu Ala Glu Lys Ile Lys Val Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro His Phe Leu Phe Lys Ile Ile Phe Gly Asp
        195                 200                 205

Lys Met Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
            260                 265                 270

His Trp Arg Gln Ala Val Lys Ser Gly Lys Phe Gln Ala Phe Asp Trp
        275                 280                 285

Gly Ala Pro Tyr Gln Asn Leu Met His Tyr His Gln Pro Thr Pro Pro
    290                 295                 300

Ile Tyr Asn Leu Thr Ala Met Asn Val Pro Ile Ala Val Trp Ser Ala
305                 310                 315                 320

Asp Asn Asp Leu Leu Ala Asp Pro Gln Asp Val Asp Phe Leu Leu Ser
                325                 330                 335

Lys Leu Ser Asn Leu Ile Tyr His Lys Glu Ile Pro Asn Tyr Asn His
            340                 345                 350

Leu Asp Phe Ile Trp Ala Met Asp Ala Pro Gln Glu Val Tyr Asn Glu
        355                 360                 365

Ile Val Ser Leu Met Ala Glu Asp Lys Lys
    370                 375

<210> SEQ ID NO 6
<211> LENGTH: 1137
<212> TYPE: DNA
<213> ORGANISM: Artificial Sequence
<220> FEATURE:
<223> OTHER INFORMATION: cDNA mutant 2 (excluding signal sequence)

<400> SEQUENCE: 6
tttttgggta agattgccaa gaacccagaa gcctccatga acgtttctca atgatctct      60 tactggggtt acccatctga aatgcacaag gtcatcactg ctgatggtta catcttacaa    120
gtctacagaa ttccacacgg taagaacaac tccaaccatt gggtcaaag accagttgtc    180 tttttgcaac acggtctatt aggttctgct accaactgga tctccaactt gccaaacaac   240
tctttgggtt tcttgttggc tgatgccggt tacgatgtct ggttaggtaa ctcccgtggt    300
aacacctggg ctcaagaaca cttgtactac tctccagact ctccagaatt ctgggctttc   360
tctttcgacg aaatggctga atacgacttg ccatctacca ttgacttcat cttgaacaag    420
accggtcaaa agaagttgca ctacgttggt cactctcaag gtaccaccat tggtttcatc    480
gctttctcca cttctccaac tttggctgaa aagatcaagg ttttctacgc tttggctcca   540

```
gttgctaccg tcaagtacac caaatcttta ttcaacaaat tggctttgat tccacacttc     600
ttattcaaga tcatcttcgg tgacaagatg ttctacccac acactttctt ggaacaattc     660
ttgggtgttg aaatgtgttc cagagaaact ttggatgtct tgtgtaagaa cgctttgttt     720
gccatcactg tgttgacaa caagaacttc aacatgtcca gattagatgt ctacattgct      780
cacaacccag ccggtacttc tgttcaaaac actttgcact ggagacaagc tgtcaagtct     840
ggtaagttcc aagccttcga ctggggtgct ccataccaaa acttgatgca ctacaaccaa     900
tccactccac ctatctacaa cttgactgcc atgaacgttc aattgctgt ctggtctgct      960 gacaacgatt tgttggctga ccctcaagat gtcgatttct tgctatccaa gttgtccaac    1020
ttgacctacc acaaggaaat tccaaactac aaccatttgg acttcatctg ggctatggac    1080
gctccacaag aagtttacaa cgaaatcgtt tctttgatgg ctgaagacaa aaaataa       1137
```

<210> SEQ ID NO 7
<211> LENGTH: 378
<212> TYPE: PRT
<213> ORGANISM: Artificial Sequence
<220> FEATURE:
<223> OTHER INFORMATION: protein mutant 2 (lacking signal sequence)

<400> SEQUENCE: 7

```
Phe Leu Gly Lys Ile Ala Lys Asn Pro Glu Ala Ser Met Asn Val Ser
1               5                   10                  15

Gln Met Ile Ser Tyr Trp Gly Tyr Pro Ser Glu Met His Lys Val Ile
            20                  25                  30

Thr Ala Asp Gly Tyr Ile Leu Gln Val Tyr Arg Ile Pro His Gly Lys
        35                  40                  45

Asn Asn Ser Asn His Leu Gly Gln Arg Pro Val Val Phe Leu Gln His
    50                  55                  60

Gly Leu Leu Gly Ser Ala Thr Asn Trp Ile Ser Asn Leu Pro Asn Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ala Gln Glu His Leu Tyr Tyr Ser Pro
            100                 105                 110

Asp Ser Pro Glu Phe Trp Ala Phe Ser Phe Asp Glu Met Ala Glu Tyr
        115                 120                 125

Asp Leu Pro Ser Thr Ile Asp Phe Ile Leu Asn Lys Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Thr Leu Ala Glu Lys Ile Lys Val Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro His Phe Leu Lys Ile Ile Phe Gly Asp
        195                 200                 205

Lys Met Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
```

```
                260              265                 270
     His Trp Arg Gln Ala Val Lys Ser Gly Lys Phe Gln Ala Phe Asp Trp
                    275                 280                 285

Gly Ala Pro Tyr Gln Asn Leu Met His Tyr Asn Gln Ser Thr Pro Pro
                290                 295                 300

Ile Tyr Asn Leu Thr Ala Met Asn Val Pro Ile Ala Val Trp Ser Ala
     305                 310                 315                 320

Asp Asn Asp Leu Leu Ala Asp Pro Gln Asp Val Asp Phe Leu Leu Ser
                     325                 330                 335

Lys Leu Ser Asn Leu Thr Tyr His Lys Glu Ile Pro Asn Tyr Asn His
                 340                 345                 350

Leu Asp Phe Ile Trp Ala Met Asp Ala Pro Gln Glu Val Tyr Asn Glu
                 355                 360                 365

Ile Val Ser Leu Met Ala Glu Asp Lys Lys
                 370                 375

<210> SEQ ID NO 8
<211> LENGTH: 1137
<212> TYPE: DNA
<213> ORGANISM: Artificial Sequence
<220> FEATURE:
<223> OTHER INFORMATION: cDNA mutant 3 (excluding signal sequence)

<400> SEQUENCE: 8
tttttgggta agattgccaa gaacccagaa gcctccatga acgtctctca aatgatctct     60
tactggggtt acccatctga agaacacaag gttaccactg aagacggtta catcttggaa    120
gtcaacagaa ttccacacgg taagaagaac tctgaaaaca ccggtcaaag acctgttgtt    180
ttcttgcaac acggtctatt gggttctgct accaactgga tctccaactt gccaaagaac    240
tctttaggtt tcttgttggc tgacgctggt tacgatgtct ggttaggtaa ctcccgtggt    300
aacacctggg ctagaaagca tttgtactac tctccagatt ccaaggaatt ctgggctttc    360
tctttcgatg aaatggccaa gtacgacttg ccatctacca ttgacttcat cttgagaaga    420
accggtcaaa gaaaattgca ctacgttggt cactctcaag gtaccaccat cggtttcatt    480
gctttctcca cttctccaga attggctgaa agatcaaga cttttctacgc tttggctcca    540 gttgctaccg ttaagtacac caaatctttta ttcaacaaat ggctttgat tccacacttc    600 ttgttcaaga tcattttcgg tgacaagatg ttctacccac acactttctt ggaacaattt    660
ttgggtgtcg aaatgtgttc cagagaaact ttggatgtct tatgtaagaa cgctttgttt    720
gccatcactg gtgttgacaa caagaacttc aacatgtcca gattagatgt ttacattgct    780
cacaacccag ccggtacttc cgttcaaaac actttgcact ggagacaagc tgtcaaatct    840
ggtaagttcc aagcctacga ctggggttct ccagaccaaa cagaatgca ctaccatcaa    900 tccactccac caatctacaa cttgactgct atgaacgttc caactgctgt ctggtctgct    960
gacaacgatt tgttggctga ccctcaagat gtcaagaact tgctatccaa gttgtccaac    1020
ttgatctacc acaaggaaat tccaaactac aaccatttgg acttcatctg gggtgaagat    1080
gctccacaag aagtttacaa cgaaatcgtc tctttgatga aggaagacaa gaaataa      1137

<210> SEQ ID NO 9
<211> LENGTH: 378
<212> TYPE: PRT
<213> ORGANISM: Artificial Sequence
<220> FEATURE:
<223> OTHER INFORMATION: protein mutant 3 (lacking signal sequence)
```

<400> SEQUENCE: 9

```
Phe Leu Gly Lys Ile Ala Lys Asn Pro Glu Ala Ser Met Asn Val Ser
1               5                   10                  15

Gln Met Ile Ser Tyr Trp Gly Tyr Pro Ser Glu His Lys Val Thr
            20                  25                  30

Thr Glu Asp Gly Tyr Ile Leu Glu Val Asn Arg Ile Pro His Gly Lys
        35                  40                  45

Lys Asn Ser Glu Asn Thr Gly Gln Arg Pro Val Val Phe Leu Gln His
    50                  55                  60

Gly Leu Gly Ser Ala Thr Asn Trp Ile Ser Asn Leu Pro Lys Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ala Arg Lys His Leu Tyr Tyr Ser Pro
            100                 105                 110

Asp Ser Lys Glu Phe Trp Ala Phe Ser Phe Asp Glu Met Ala Lys Tyr
        115                 120                 125

Asp Leu Pro Ser Thr Ile Asp Phe Ile Leu Arg Arg Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Glu Leu Ala Glu Lys Ile Lys Thr Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro His Phe Leu Phe Lys Ile Ile Phe Gly Asp
        195                 200                 205

Lys Met Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
            260                 265                 270

His Trp Arg Gln Ala Val Lys Ser Gly Lys Phe Gln Ala Tyr Asp Trp
        275                 280                 285

Gly Ser Pro Asp Gln Asn Arg Met His Tyr His Gln Ser Thr Pro Pro
    290                 295                 300

Ile Tyr Asn Leu Thr Ala Met Asn Val Pro Thr Ala Val Trp Ser Ala
305                 310                 315                 320

Asp Asn Asp Leu Leu Ala Asp Pro Gln Asp Val Lys Asn Leu Leu Ser
                325                 330                 335

Lys Leu Ser Asn Leu Ile Tyr His Lys Glu Ile Pro Asn Tyr Asn His
            340                 345                 350

Leu Asp Phe Ile Trp Gly Glu Asp Ala Pro Gln Glu Val Tyr Asn Glu
        355                 360                 365

Ile Val Ser Leu Met Lys Glu Asp Lys Lys
    370                 375
```

<210> SEQ ID NO 10
<211> LENGTH: 1137
<212> TYPE: DNA
<213> ORGANISM: Artificial Sequence
<220> FEATURE:
<223> OTHER INFORMATION: cDNA mutant 4 (excluding signal sequence)

<400> SEQUENCE: 10

```
tttttgggta agattgccaa gaacccagaa gcctccatga acgtttctga aatcatctct      60
tactggggtt acccatctga agaacacgaa gttaccactg aagatggtta cattttggaa    120
gttaaccgta ttccacacgg taagaagaac tctgaacaca ccggtaagag acctgttgtt    180
ttcttacaac acggtctatt aggttctgct accaactgga tctctaactt gccaaagaac    240
tctttgggtt tcttgttggc tgatgctggt tacgatgtct ggttaggtaa ctccagaggt    300
aacacctggt ccagaaagca aagacttta tctccagact ccaaggaatt ctgggctttc    360
tctttcgacg aaatggccaa gtacgatttg ccatctacca ttgacttcat cttaaagaag    420
actggtcaaa agaaattgca ctcgtcggt cactctcaag gtaccaccat ggtttcatc      480
gctttctcca cctctccaga attggccaag aagatcaaga ctttctacgc tttggctcca    540
gttgctaccg tcaaatacac caaatcttta ttcaacaaat ggctcatttt gccagaattt    600
ttgttcaagg acttgttcgg tgacaaggaa ttctacccac acactttctt ggaacaattc    660
ttgggtgttg aaatgtgttc cagagaaact ttggatgtct tgtgtaagaa cgctttgttt    720
gccatcactg gtgtcgacaa caagaacttc aacatgtcca gattggatgt ttacattgct    780
cacaacccag ctggtacttc cgtccaaaac actttgcact ggagacaagc tgtcaaatct    840
ggtaagttcc aagccttcga ctggggttct ccagaccaaa acatgaagca ctaccatcaa    900
tccactccac cagaatacaa cgttaccgac atgaaggttc caactgctgt ctggtctgct    960
gacaacgatt tgttggctga ccctcaagat gttgacttct gttgtccaa attgtccaac   1020
ttgatctacc acaaggaaat cccacactac aaccatttgg acttcatctg gggtgaagat   1080
gctccacaag aagtctacaa cgaaattatc agattgatga aggaagacaa gaagtaa      1137
```

<210> SEQ ID NO 11
<211> LENGTH: 378
<212> TYPE: PRT
<213> ORGANISM: Artificial Sequence
<220> FEATURE:
<223> OTHER INFORMATION: protein mutant 4 (lacking signal sequence)

<400> SEQUENCE: 11

```
Phe Leu Gly Lys Ile Ala Lys Asn Pro Glu Ala Ser Met Asn Val Ser
  1               5                  10                  15

Glu Ile Ile Ser Tyr Trp Gly Tyr Pro Ser Glu Glu His Glu Val Thr
             20                  25                  30

Thr Glu Asp Gly Tyr Ile Leu Glu Val Asn Arg Ile Pro His Gly Lys
         35                  40                  45

Lys Asn Ser Glu His Thr Gly Lys Arg Pro Val Val Phe Leu Gln His
     50                  55                  60

Gly Leu Leu Gly Ser Ala Thr Asn Trp Ile Ser Asn Leu Pro Lys Asn
 65                  70                  75                  80

Ser Leu Gly Phe Leu Leu Ala Asp Ala Gly Tyr Asp Val Trp Leu Gly
                 85                  90                  95

Asn Ser Arg Gly Asn Thr Trp Ser Arg Lys His Lys Thr Leu Ser Pro
            100                 105                 110

Asp Ser Lys Glu Phe Trp Ala Phe Ser Phe Asp Glu Met Ala Lys Tyr
        115                 120                 125

Asp Leu Pro Ser Thr Ile Asp Phe Ile Leu Lys Lys Thr Gly Gln Lys
    130                 135                 140
```

Lys Leu His Tyr Val Gly His Ser Gln Gly Thr Thr Ile Gly Phe Ile
145                 150                 155                 160

Ala Phe Ser Thr Ser Pro Glu Leu Ala Lys Ile Lys Thr Phe Tyr
            165                 170                 175

Ala Leu Ala Pro Val Ala Thr Val Lys Tyr Thr Lys Ser Leu Phe Asn
            180                 185                 190

Lys Leu Ala His Leu Pro Glu Phe Leu Phe Lys Asp Leu Phe Gly Asp
            195                 200                 205

Lys Glu Phe Tyr Pro His Thr Phe Leu Glu Gln Phe Leu Gly Val Glu
        210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
                260                 265                 270

His Trp Arg Gln Ala Val Lys Ser Gly Lys Phe Gln Ala Phe Asp Trp
            275                 280                 285

Gly Ser Pro Asp Gln Asn Met Lys His Tyr His Gln Ser Thr Pro Pro
290                 295                 300

Glu Tyr Asn Val Thr Asp Met Lys Val Pro Thr Ala Val Trp Ser Ala
305                 310                 315                 320

Asp Asn Asp Leu Leu Ala Asp Pro Gln Asp Val Asp Phe Leu Leu Ser
                325                 330                 335

Lys Leu Ser Asn Leu Ile Tyr His Lys Glu Ile Pro His Tyr Asn His
            340                 345                 350

Leu Asp Phe Ile Trp Gly Glu Asp Ala Pro Gln Glu Val Tyr Asn Glu
            355                 360                 365

Ile Ile Arg Leu Met Lys Glu Asp Lys Lys
370                 375

<210> SEQ ID NO 12
<211> LENGTH: 1134
<212> TYPE: DNA
<213> ORGANISM: Artificial Sequence
<220> FEATURE:
<223> OTHER INFORMATION: cDNA mutant 5 (excluding signal sequence)

<400> SEQUENCE: 12
ttcttgggta agatcgccaa gaacccagaa gcctccatga acgtttccca aatgatctct    60
tactggggtt acccatctga aatgcacaag gtcatcactg ctgacggtta catcttacaa   120
gtctacagaa tcccacacgg taagaacaat gccaaccatt tgggtcaaag accagttgtt   180
ttcttgcaac acggtctatt aggttctgct accaactgga tctccaactt gccaaagaac   240
tctttgggtt tcttgttggc tgatgctggt tacgatgtct ggttgggtaa ctccagaggt   300
aacacctggg ctcaagaaca cttgtactac tctccagatt ctccagaatt ctgggctttc   360
tccttcgacg aaatggctga atacgacttg ccatctacca ttgacttcat cttgagaaga   420
accggtcaaa agaaattgca ctacgttggt cactctcaag taccaccat gggtttcatt    480 gctttctcca cttctccaac tttggctgaa agatcaagg ttttctacgc tttggctcca    540
gttgccaccg tcaagtacac caagtcttta ttcaacaaat ggctttgat tccacacttc   600 ttgttcaaga tcatctttgg tgacaagatg ttctacccac acactttctt ggaacaattc   660
ttgggtgttg aaatgtgttc tcgtgaaact ttggatgttc tatgtaagaa cgctttgttt   720

```
gccatcactg gtgttgacaa caagaacttc aacatgtcca gattggacgt ctacattgct    780
cacaacccag ccggtacttc tgttcaaaac actttgcact ggagacaagc tgtcaaatct    840
ggtaagttcc aagcctttga ctggggtgct ccataccaaa acttgatgca ctaccatcaa    900
ccaactccac caatttacaa cttgactgcc atgaacgttc caattgctgt ctggtctgct    960
gacaacgact tattagctga tcctcaagat gtcgatttct tgttgtccaa gttgtccaac   1020
ttgatctacc acaaggaaat cccaaactac aaccatttgg atttcatctg gctatggac   1080 gctcctcaag aagtctacaa cgaaattgtc tctttgatgg ctgaagacaa gaaa          1134
```

<210> SEQ ID NO 13
<211> LENGTH: 397
<212> TYPE: PRT
<213> ORGANISM: Artificial Sequence
<220> FEATURE:
<223> OTHER INFORMATION: protein mutant 5

<400> SEQUENCE: 13

```
Met Trp Trp Leu Leu Val Thr Val Cys Phe Ile His Met Ser Gly Asn
  1               5                  10                  15

Ala Phe Cys Phe Leu Gly Lys Ile Ala Lys Asn Pro Glu Ala Ser Met
             20                  25                  30

Asn Val Ser Gln Met Ile Ser Tyr Trp Gly Tyr Pro Ser Glu Met His
         35                  40                  45

Lys Val Ile Thr Ala Asp Gly Tyr Ile Leu Gln Val Tyr Arg Ile Pro
     50                  55                  60

His Gly Lys Asn Asn Ala Asn His Leu Gly Gln Arg Pro Val Val Phe
 65                  70                  75                  80

Leu Gln His Gly Leu Leu Gly Ser Ala Thr Asn Trp Ile Ser Asn Leu
                 85                  90                  95

Pro Lys Asn Ser Leu Gly Phe Leu Leu Ala Asp Ala Gly Tyr Asp Val
            100                 105                 110

Trp Leu Gly Asn Ser Arg Gly Asn Thr Trp Ala Gln Glu His Leu Tyr
        115                 120                 125

Tyr Ser Pro Asp Ser Pro Glu Phe Trp Ala Phe Ser Phe Asp Glu Met
    130                 135                 140

Ala Glu Tyr Asp Leu Pro Ser Thr Ile Asp Phe Ile Leu Arg Arg Thr
145                 150                 155                 160

Gly Gln Lys Lys Leu His Tyr Val Gly His Ser Gln Gly Thr Thr Ile
                165                 170                 175

Gly Phe Ile Ala Phe Ser Thr Ser Pro Thr Leu Ala Glu Lys Ile Lys
            180                 185                 190

Val Phe Tyr Ala Leu Ala Pro Val Ala Thr Val Lys Tyr Thr Lys Ser
        195                 200                 205

Leu Phe Asn Lys Leu Ala Leu Ile Pro His Phe Leu Phe Lys Ile Ile
    210                 215                 220

Phe Gly Asp Lys Met Phe Tyr Pro His Thr Phe Leu Glu Gln Phe Leu
225                 230                 235                 240

Gly Val Glu Met Cys Ser Arg Glu Thr Leu Asp Val Leu Cys Lys Asn
                245                 250                 255

Ala Leu Phe Ala Ile Thr Gly Val Asp Asn Lys Asn Phe Asn Met Ser
            260                 265                 270

Arg Leu Asp Val Tyr Ile Ala His Asn Pro Ala Gly Thr Ser Val Gln
        275                 280                 285
```

```
Asn Thr Leu His Trp Arg Gln Ala Val Lys Ser Gly Lys Phe Gln Ala
        290                 295                 300

Phe Asp Trp Gly Ala Pro Tyr Gln Asn Leu Met His Tyr His Gln Pro
305                 310                 315                 320

Thr Pro Pro Ile Tyr Asn Leu Thr Ala Met Asn Val Pro Ile Ala Val
                325                 330                 335

Trp Ser Ala Asp Asn Asp Leu Leu Ala Asp Pro Gln Asp Val Asp Phe
                340                 345                 350

Leu Leu Ser Lys Leu Ser Asn Leu Ile Tyr His Lys Glu Ile Pro Asn
            355                 360                 365

Tyr Asn His Leu Asp Phe Ile Trp Ala Met Asp Ala Pro Gln Glu Val
        370                 375                 380

Tyr Asn Glu Ile Val Ser Leu Met Ala Glu Asp Lys Lys
385                 390                 395
```

<210> SEQ ID NO 14
<211> LENGTH: 57
<212> TYPE: DNA
<213> ORGANISM: Artificial Sequence
<220> FEATURE:
<223> OTHER INFORMATION: DNA CPO signal sequence PGE

<400> SEQUENCE: 14

```
atgtggtggt tattggttac cgtttgtttc attcacatgt ccggtaacgc tttctgt        57
```

<210> SEQ ID NO 15
<211> LENGTH: 1137
<212> TYPE: DNA
<213> ORGANISM: Aspergillus niger

<400> SEQUENCE: 15

```
ttccttggaa agatcgccaa gaaccctgag gcttccatga acgtcagcca gatgatcagc        60
tactggggtt acccttccga gatgcacaag gtcattactg ccgatggcta catcctccag       120
gtctaccgca ttcctcacgg aaagaacaac gccaaccacc tgggtcagcg ccctgttgtt       180
ttcctgcagc acggtcttct gggctctgcc accaactgga tcagcaacct ccccaagaac       240
tccctgggtt tcctccttgc cgatgccggt tacgacgtct ggctcggtaa ctcccgcggc       300
aacacctggg ctcaggagca cctctactac tctcccgact cccccgagtt ctgggctttc       360
tccttcgacg agatggctga gtacgacctc ccctctacca ttgacttcat cctgcgtcgc       420
accggtcaga agaagctcca ctacgtcggc cacagccagg tactaccat tggtttcatt       480
gctttctcca ccagccccac cctcgctgag aagatcaagg tcttctacgc tcttgccccc       540
gttgccaccg tcaagtacac taagtccctc ttcaacaagc ttgctctgat ccctcacttc       600
ctcttcaaga tcatcttcgg tgataagatg ttctaccctc acactttcct ggagcagttc       660
ctgggtgtgg agatgtgctc tcgcgagacc ctggatgtcc tctgcaagaa cgccctcttc       720
gccatcactg gcgttgacaa caagaacttc aacatgagcc gtcttgatgt ctacatcgcc       780
cacaaccctg ctggcaccag cgtccagaac accctccact ggcgtcaggc tgtcaagtcc       840
ggaaagttcc aggctttcga ctggggcgct ccctaccaga acctgatgca ctaccaccag       900
cccactcctc ccatctacaa cctgaccgcc atgaacgtcc ccattgctgt ctggtccgcc       960
gacaacgacc tccttgccga ccctcaggat gttgacttcc tcctctccaa gctcagcaac      1020
ctgatctacc acaaggagat ccccaactac aaccacctcg acttcatctg ggccatggat      1080
gcccctcagg aggtctacaa cgagatcgtc tctctgatgg ctgaggacaa gaagtaa         1137
```

<210> SEQ ID NO 16
<211> LENGTH: 1137
<212> TYPE: DNA
<213> ORGANISM: Artificial Sequence
<220> FEATURE:
<223> OTHER INFORMATION: Mutant 1 for A.niger (PGE-9 variant of
K.lactis = PGE-10 variant of A.niger)

<400> SEQUENCE: 16

```
ttcctgggca agatcgccaa gaaccccgag gccagcatga acgtcagcca gatgatctct      60
tactggggtt accccctccga gatgcacaag gtcatcaccg ccgatggcta catcctccag    120
gtctaccgta tcccccacgg caagaacaac tccaaccacc tgggccagcg ccccgttgtt    180
ttcctgcagc acggtctgct tggctctgcc accaactgga tctccaacct ccccaacaac    240
tcgctaggat tcctccttgc cgatgctggt tacgatgtct ggctaggaaa ctcccgtggt    300
aacacctggg ctcaggagca cctctactac tctcctgact ctcctgagtt ctgggctttc    360
tccttcgacg agatggctga gtacgacctt cctagcacca ttgacttcat cctgaacaag    420
actggccaga agaagctcca ctacgtcggt cactcccagg gtactaccat cggtttcatt    480
gctttctcca cctccccccac cctggctgag aagatcaagg tgttctacgc tcttgctcct    540
gttgccactg tcaagtacac caagtccctc ttcaacaagc ttgctctgat ccccacttc     600
ctcttcaaga tcatcttcgg tgacaagatg ttctaccccc cacccttcct ggagcagttc    660
cttggtgttg agatgtgctc tcgcgaaacc ctcgatgtcc tctgcaagaa cgccctcttc    720
gccatcaccg tgttgacaa caagaacttc aacatgagcc gtctggatgt ctacattgcc    780
cacaaccctg ctggcacctc cgtccagaac accctccact ggcgccaggc cgtcaagtcc    840
ggcaagttcc aggctttcga ctggggtgct ccctaccaga acctgatgca ctacaaccag    900
agcactcctc ccatctacaa cttgactgcc atgaacgtcc ccattgccgt ctggtccgcc    960
gacaacgacc tccttgccga ccccaggat gttgacttcc tcctcagcaa gctctccaac   1020
ctgacctacc acaaggagat ccccaactac aaccacctcg acttcatctg ggccatggat   1080
gctcctcagg aagtctacaa cgaaatagta tctctgatgg ctgaggacaa gaagtaa      1137
```

<210> SEQ ID NO 17
<211> LENGTH: 1137
<212> TYPE: DNA
<213> ORGANISM: Artificial Sequence
<220> FEATURE:
<223> OTHER INFORMATION: Mutant 2 for A. niger (PGE-12 variant of K.
lactis = PGE-16 variant of A. niger)

<400> SEQUENCE: 17

```
ttcctgggca agattgccaa gaaccccgag gcctccatga acgtcagcga aatcatctct      60
tactggggtt accccctccga ggagcacgaa gtcaccactg aggatggatc catcctggag   120
gtcaaccgta tcccccacgg caagaagaac agcgaacaca ccggcaagcg ccccgttgtt   180
ttcctgcagc acggtctgct tggctctgcc accaactgga tctccaacct ccccaagaac   240
tccctgggtt tcctccttgc cgatgccggt tacgatgtct ggctaggcaa ctcccgtggt   300
aacacctggt caaggaagca caagacccctc tctcctgaca gcaaggagtt ctgggctttc   360
tccttcgacg agatggccaa gtacgacctc cccagcacca tcgacttcat cctcaagaaa   420
actggccaga agaagctcca ctacgtcggt cactcccagg gcaccaccat cggtttcatt   480
gctttctcca cctccccccga gcttgccaag aagatcaaga ccttctacgc tcttgctcct   540
gttgccactg tcaagtacac caagtccctc ttcaacaagc ttgctcacct cccgagttc    600
```

```
ctcttcaagg acctcttcgg tgacaaggag ttctaccccc acaccttcct ggagcagttc      660
ctgggtgttg agatgtgctc tcgcgaaacc ctcgatgtcc tttgcaagaa cgccctcttc      720
gccatcaccg tgttgacaa  caagaacttc aacatgagcc gtctggatgt ctacattgcc      780
cacaaccctg ctggtacttc cgtccagaac accctccact ggcgccaggc tgtcaagtcc      840
ggcaagttcc aggctttcga ctggggttct cctgaccaga acatgaagca ctaccaccag      900
agcactcctc ccgagtacaa cgtcaccgac atgaaggtcc ccactgctgt ctggtccgcc      960
gacaacgacc tccttgccga ccccaggat  gttgacttcc tgctctccaa gctctccaac     1020
ctgatctacc acaaggagat ccccactac  aaccacctcg acttcatctg gggtgaggat     1080
gctcctcagg aagtctacaa cgagatcatc cgtctgatga agaggacaa  gaagtaa       1137
```

<210> SEQ ID NO 18
<211> LENGTH: 378
<212> TYPE: PRT
<213> ORGANISM: Artificial Sequence
<220> FEATURE:
<223> OTHER INFORMATION: mature protein (1aa difference to MUTANT 4
      K.lactis)

<400> SEQUENCE: 18

```
Phe Leu Gly Lys Ile Ala Lys Asn Pro Glu Ala Ser Met Asn Val Ser
1               5                   10                  15

Glu Ile Ile Ser Tyr Trp Gly Tyr Pro Ser Glu His Glu Val Thr
            20                  25                  30

Thr Glu Asp Gly Ser Ile Leu Glu Val Asn Arg Ile Pro His Gly Lys
        35                  40                  45

Lys Asn Ser Glu His Thr Gly Lys Arg Pro Val Val Phe Leu Gln His
    50                  55                  60

Gly Leu Leu Gly Ser Ala Thr Asn Trp Ile Ser Asn Leu Pro Lys Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ser Arg Lys His Lys Thr Leu Ser Pro
            100                 105                 110

Asp Ser Lys Glu Phe Trp Ala Phe Ser Phe Asp Glu Met Ala Lys Tyr
        115                 120                 125

Asp Leu Pro Ser Thr Ile Asp Phe Ile Leu Lys Lys Thr Gly Gln Lys
    130                 135                 140

Lys Leu His Tyr Val Gly His Ser Gln Gly Thr Thr Ile Gly Phe Ile
145                 150                 155                 160

Ala Phe Ser Thr Ser Pro Glu Leu Ala Lys Lys Ile Lys Thr Phe Tyr
                165                 170                 175

Ala Leu Ala Pro Val Ala Thr Val Lys Tyr Thr Lys Ser Leu Phe Asn
            180                 185                 190

Lys Leu Ala His Leu Pro Glu Phe Leu Phe Lys Asp Leu Phe Gly Asp
        195                 200                 205

Lys Glu Phe Tyr Pro His Thr Phe Leu Glu Gln Phe Leu Gly Val Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Ile Ala His Asn Pro Ala Gly Thr Ser Val Gln Asn Thr Leu
```

```
                260                 265                 270
His Trp Arg Gln Ala Val Lys Ser Gly Lys Phe Gln Ala Phe Asp Trp
            275                 280                 285

Gly Ser Pro Asp Gln Asn Met Lys His Tyr His Gln Ser Thr Pro Pro
        290                 295                 300

Glu Tyr Asn Val Thr Asp Met Lys Val Pro Thr Ala Val Trp Ser Ala
305                 310                 315                 320

Asp Asn Asp Leu Leu Ala Asp Pro Gln Asp Val Asp Phe Leu Leu Ser
                325                 330                 335

Lys Leu Ser Asn Leu Ile Tyr His Lys Glu Ile Pro His Tyr Asn His
            340                 345                 350

Leu Asp Phe Ile Trp Gly Glu Asp Ala Pro Gln Glu Val Tyr Asn Glu
        355                 360                 365

Ile Ile Arg Leu Met Lys Glu Asp Lys Lys
        370                 375

<210> SEQ ID NO 19
<211> LENGTH: 1137
<212> TYPE: DNA
<213> ORGANISM: Artificial Sequence
<220> FEATURE:
<223> OTHER INFORMATION: Mutant 3 for A.niger (PGE-12 of A.niger)

<400> SEQUENCE: 19
ttcctgggca agattgccaa gaaccccgag gccagcatga acgtttccca gatgatctcc      60
tactggggtt acccctccga ggagtacgag gtcaccactg aggatggcta catcctggag     120
gtcaaccgta tcccccacgg caagaagaac tccgagaaca ctggccagcg tcccgttgtt     180
ttcctgcagc acggtctgct tggttccgcc accaactgga tctccaacct ccccaacaac     240
tcgctaggat tcctccttgc cgatgccggt tacgatgtct ggctaggcaa ctcccgtggt     300
aacacctggg ctcgccgcaa cctctactac tctcctgact ccgttgagtt ctgggctttc     360
tccttcgacg agatggctga gtacgacctc cccagcacca ttgacttcat cctggaaaag     420
accggccagg agcagctgca ctacgtcggt cactcccagg gtactaccat cggtttcatt     480
gctttctcca cctcccccga gcttgctgag aagatcaaga ccttctacgc tcttgctcct     540
gttgccaccg tcaagtacac caagtccctc ttcaacaagc ttgctctgat cccccagtcc     600
ctcttcaagg acctcttcgg tgacaaggag ttctaccccc acaccttcct ggagcagttc     660
ctggccactg agatgtgctc tcgcgaaacc ctcgatgtcc tctgcaagaa cgccctcttc     720
gccatcaccg tgttgacaa caagaacttc aacatgagcc gtctggatgt ctacctttct     780
cacaaccctg ctggcaccct cgtccagaac ccctccact ggcgccaggc tgtcaagtcc     840
ggcaagttcc aggcctacga ctgggggttct cctgaccaga accaggagca ctacgaccag     900
agcactcctc ccatctacaa cctcaccgac atgaacgtcc ccactgctgt ctggtctgcc     960
gacaacgacc tccttgccga ccccaggat gttgagaacc tcctcagcaa gctcagcaac    1020
ctgatctacc acaaggagat ccccaactac aaccacctcg acttcatctg ggtgaggat    1080 gctcctcagg aagtctacaa cgaaatagta tctctgatgg aagaagataa aaagtaa      1137

<210> SEQ ID NO 20
<211> LENGTH: 378
<212> TYPE: PRT
<213> ORGANISM: Artificial Sequence
<220> FEATURE:
<223> OTHER INFORMATION: mature protein
```

```
<400> SEQUENCE: 20

Phe Leu Gly Lys Ile Ala Lys Asn Pro Glu Ala Ser Met Asn Val Ser
1               5                   10                  15

Gln Met Ile Ser Tyr Trp Gly Tyr Pro Ser Glu Glu Tyr Glu Val Thr
            20                  25                  30

Thr Glu Asp Gly Tyr Ile Leu Glu Val Asn Arg Ile Pro His Gly Lys
        35                  40                  45

Lys Asn Ser Glu Asn Thr Gly Gln Arg Pro Val Val Phe Leu Gln His
    50                  55                  60

Gly Leu Gly Ser Ala Thr Asn Trp Ile Ser Asn Leu Pro Asn Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ala Arg Arg Asn Leu Tyr Tyr Ser Pro
            100                 105                 110

Asp Ser Val Glu Phe Trp Ala Phe Ser Phe Asp Glu Met Ala Glu Tyr
        115                 120                 125

Asp Leu Pro Ser Thr Ile Asp Phe Ile Leu Glu Lys Thr Gly Gln Glu
    130                 135                 140

Gln Leu His Tyr Val Gly His Ser Gln Gly Thr Thr Ile Gly Phe Ile
145                 150                 155                 160

Ala Phe Ser Thr Ser Pro Glu Leu Ala Glu Lys Ile Lys Thr Phe Tyr
                165                 170                 175

Ala Leu Ala Pro Val Ala Thr Val Lys Tyr Thr Lys Ser Leu Phe Asn
            180                 185                 190

Lys Leu Ala Leu Ile Pro Gln Ser Leu Phe Lys Asp Leu Phe Gly Asp
        195                 200                 205

Lys Glu Phe Tyr Pro His Thr Phe Leu Glu Gln Phe Leu Ala Thr Glu
    210                 215                 220

Met Cys Ser Arg Glu Thr Leu Asp Val Leu Cys Lys Asn Ala Leu Phe
225                 230                 235                 240

Ala Ile Thr Gly Val Asp Asn Lys Asn Phe Asn Met Ser Arg Leu Asp
                245                 250                 255

Val Tyr Leu Ser His Asn Pro Ala Gly Thr Ser Val Gln Asn Thr Leu
            260                 265                 270

His Trp Arg Gln Ala Val Lys Ser Gly Lys Phe Gln Ala Tyr Asp Trp
        275                 280                 285

Gly Ser Pro Asp Gln Asn Gln Glu His Tyr Asp Gln Ser Thr Pro Pro
    290                 295                 300

Ile Tyr Asn Leu Thr Asp Met Asn Val Pro Thr Ala Val Trp Ser Ala
305                 310                 315                 320

Asp Asn Asp Leu Leu Ala Asp Pro Gln Asp Val Glu Asn Leu Leu Ser
                325                 330                 335

Lys Leu Ser Asn Leu Ile Tyr His Lys Glu Ile Pro Asn Tyr Asn His
            340                 345                 350

Leu Asp Phe Ile Trp Gly Glu Asp Ala Pro Gln Glu Val Tyr Asn Glu
        355                 360                 365

Ile Val Ser Leu Met Glu Glu Asp Lys Lys
    370                 375

<210> SEQ ID NO 21
<211> LENGTH: 1137
<212> TYPE: DNA
<213> ORGANISM: Artificial Sequence
```

<220> FEATURE:
<223> OTHER INFORMATION: Mutant 4 for A.niger (PGE-13 of A.niger)

<400> SEQUENCE: 21

```
ctcttcggca agctccaccc caaccccgag gccaacatga acatctccca gatcatctcc      60
tactggggtt acccctccga ggagtacgag gttgtcaccg aggatggcta catcctcgag     120
gtcaaccgta tccccacgg caagaacaac gccaacaaca ctggccagcg tcccgttgtt      180
ttcctgcagc acggtctgct tggctctgcc agcaactgga tctccaacct ccccaacaac    240
tctcttggtt tcctccttgc cgatgctggt tacgatgtct ggctaggcaa ctcccgtggt    300
aacacctggt cccgcaagca aagaccctc agccctgaca cgttgagtt ctgggctttc      360
tccttcgacg agatggccaa gtacgacctc cccgccacca ttgacttcat cctggaaaag   420
accggccagg agcagctcta ctacgtcggt cactcccagg gtactaccat tggttttcatt 480
gctttctcca ccaaccccga gcttgctgag aagatcaaga ccttctacgc ccttgctcct    540
gttgccaccg tcaagtacac caagtccctc ttcaacaagc tggctctgat ccccgactcc    600
ctcttcaagg tcctcttcgg tgacaaggag ttctaccccc acaccttcct ggagcagttc    660
ctggccactg agatgtgctc tcgcgaaacc ctcgacctcc tttgctccaa cgccctcttc    720
gccatcaccg gtgttgacaa caagaacttc aacatgagcc gtctggatgt ctacctctcc    780
cacaaccctg ctggtacttc cgtccagaac ccctccact ggcgccaggc tgtcaagtcc     840
ggcaagttcc aggctttcga ctggggttct cctgaccaga accaggagca ctacaaccag   900
agcactcctc ctctgtacaa cctgaccgac atgaacgtcc ccactgctgt ctggtccggt   960
ggtcaggatc ttctggccga ccccaggat gttgacctcc tcctcccaa gatcaccaac    1020
ctgatctacc acaaggagat ccccaactac aaccacctcg acttcatctg ggccatggat 1080
gctcctcagg aagtctacaa cgaaatagta tctctgatgg aagaggacaa gaagtaa    1137
```

<210> SEQ ID NO 22
<211> LENGTH: 378
<212> TYPE: PRT
<213> ORGANISM: Artificial Sequence
<220> FEATURE:
<223> OTHER INFORMATION: mature protein

<400> SEQUENCE: 22

```
Leu Phe Gly Lys Leu His Pro Asn Pro Glu Ala Asn Met Asn Ile Ser
1               5                   10                  15

Gln Ile Ile Ser Tyr Trp Gly Tyr Pro Ser Glu Glu Tyr Glu Val Val
            20                  25                  30

Thr Glu Asp Gly Tyr Ile Leu Glu Val Asn Arg Ile Pro His Gly Lys
        35                  40                  45

Asn Asn Ala Asn Asn Thr Gly Gln Arg Pro Val Val Phe Leu Gln His
    50                  55                  60

Gly Leu Leu Gly Ser Ala Ser Asn Trp Ile Ser Asn Leu Pro Asn Asn
65                  70                  75                  80

Ser Leu Gly Phe Leu Leu Ala Asp Ala Gly Tyr Asp Val Trp Leu Gly
                85                  90                  95

Asn Ser Arg Gly Asn Thr Trp Ser Arg Lys His Lys Thr Leu Ser Pro
            100                 105                 110

Asp Ser Val Glu Phe Trp Ala Phe Ser Phe Asp Glu Met Ala Lys Tyr
        115                 120                 125

Asp Leu Pro Ala Thr Ile Asp Phe Ile Leu Glu Lys Thr Gly Gln Glu
    130                 135                 140
```

```
Gln Leu Tyr Tyr Val Gly His Ser Gln Gly Thr Thr Ile Gly Phe Ile
145                 150                 155                 160

Ala Phe Ser Thr Asn Pro Glu Leu Ala Glu Lys Ile Lys Thr Phe Tyr
                165                 170                 175

Ala Leu Ala Pro Val Ala Thr Val Lys Tyr Thr Lys Ser Leu Phe Asn
                180                 185                 190

Lys Leu Ala Leu Ile Pro Asp Ser Leu Phe Lys Val Leu Phe Gly Asp
            195                 200                 205

Lys Glu Phe Tyr Pro His Thr Phe Leu Glu Gln Phe Leu Ala Thr Glu
        210                 215                 220

Met Cys Ser Arg Glu Thr Leu Asp Leu Leu Cys Ser Asn Ala Leu Phe
225                 230                 235                 240

Ala Ile Thr Gly Val Asp Asn Lys Asn Phe Asn Met Ser Arg Leu Asp
                245                 250                 255

Val Tyr Leu Ser His Asn Pro Ala Gly Thr Ser Val Gln Asn Thr Leu
            260                 265                 270

His Trp Arg Gln Ala Val Lys Ser Gly Lys Phe Gln Ala Phe Asp Trp
        275                 280                 285

Gly Ser Pro Asp Gln Asn Gln Glu His Tyr Asn Gln Ser Thr Pro Pro
    290                 295                 300

Leu Tyr Asn Leu Thr Asp Met Asn Val Pro Thr Ala Val Trp Ser Gly
305                 310                 315                 320

Gly Gln Asp Leu Leu Ala Asp Pro Gln Asp Val Asp Leu Leu Leu Pro
                325                 330                 335

Lys Ile Thr Asn Leu Ile Tyr His Lys Glu Ile Pro Asn Tyr Asn His
                340                 345                 350

Leu Asp Phe Ile Trp Ala Met Asp Ala Pro Gln Glu Val Tyr Asn Glu
            355                 360                 365

Ile Val Ser Leu Met Glu Glu Asp Lys Lys
    370                 375

<210> SEQ ID NO 23
<211> LENGTH: 57
<212> TYPE: DNA
<213> ORGANISM: Bos taurus

<400> SEQUENCE: 23
atgtggtggc tacttgtaac agtgtgtttc atccacatgt ctggaaatgc attttgt          57
```